(12) United States Patent
Brinkman et al.

(10) Patent No.: US 7,947,692 B2
(45) Date of Patent: May 24, 2011

(54) SUBSTITUTED THIAZOLO[5,4-D]PYRIMIDINE UREA DERIVATIVES

(75) Inventors: John A. Brinkman, West Caldwell, NJ (US); Adrian Wai-Hing Cheung, Glen Rock, NJ (US); Fariborz Firooznia, Florham Park, NJ (US); Kevin Richard Guertin, Verona, NJ (US); Nicholas Marcopulos, North Caldwell, NJ (US); Lida Qi, Leonia, NJ (US); Jagdish Kumar Racha, Iselin, NJ (US); Ramakanth Sarabu, Towaco, NJ (US); Jenny Tan, New Providence, NJ (US); Jefferson Wright Tilley, North Caldwell, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 713 days.

(21) Appl. No.: 11/801,972

(22) Filed: May 11, 2007

(65) Prior Publication Data

US 2007/0270433 A1    Nov. 22, 2007

Related U.S. Application Data

(60) Provisional application No. 60/801,481, filed on May 18, 2006.

(51) Int. Cl.
| | | |
|---|---|---|
| C07D 487/04 | (2006.01) | |
| C07D 513/04 | (2006.01) | |
| A61K 31/519 | (2006.01) | |
| A61P 3/10 | (2006.01) | |
| A61P 11/06 | (2006.01) | |
| A61K 31/4353 | (2006.01) | |
| A61K 31/496 | (2006.01) | |
| A61K 31/5355 | (2006.01) | |
| A61K 31/45 | (2006.01) | |

(52) U.S. Cl. ............... 514/260.1; 514/278; 514/301; 514/252.16; 514/234.2; 544/255; 544/117; 544/121; 546/114; 546/16; 546/18

(58) Field of Classification Search ............... 544/255; 514/260.1
See application file for complete search history.

(56) References Cited

U.S. PATENT DOCUMENTS 6,060,481 A    5/2000    LaNoue et al.

FOREIGN PATENT DOCUMENTS

| EP | 1 388 341 A1 | 2/2004 |
| WO | WO 03/053946 A1 | 7/2003 |
| WO | WO 2005/070926 | 8/2005 |
| WO | WO 2005/100353 | 10/2005 |
| WO | WO 2006/013054 | 2/2006 |

*Primary Examiner* — Susanna Moore
(74) *Attorney, Agent, or Firm* — George W. Johnston; Dennis P. Tramaloni

(57) ABSTRACT

There are presented compounds of the formula

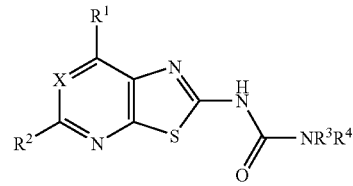

I or a pharmaceutically acceptable salt thereof, which are active adenosine A2B receptor antagonists and useful in the treatment of diabetes, diabetic retinopathy, asthma and diarrhea.

41 Claims, No Drawings

SUBSTITUTED THIAZOLO[5,4-D]PYRIMIDINE UREA DERIVATIVES

This application claims the benefit of U.S. Provisional Application No. 60/801,481, filed May 18, 2006, which is hereby incorporated by reference in its entirety.

BACKGROUND OF THE INVENTION

Adenosine is an autocoid produced in many tissues to mediate various functions through four receptor subtypes, A1, A2A, A2B and A3. All four receptors belong to the class of G-protein coupled receptors (GPCRs), which contain seven helical hydrophobic domains that span plasma membrane, connected by hydrophilic extracellular and intracellular loops. A1 and A3 receptors couple to Gi and Go proteins, while A2A and A2B receptors are coupled to Gs proteins. Because of these differences, adenosine signals an increase in intracellular cAMP levels via its action through A2A and A2B receptors, and a decrease through A1 and A3 receptors. In addition, adenosine increases intracellular calcium ion levels via A2B receptor, because of its coupling to Gq proteins.

The compounds of formula I have potent adenosine human A2B receptor antagonist activity as measured in CHO-A2B-cAMP assay.

The study of role of A2B receptor's functional activity on various cell types was complicated by the absence of selective A2B agonists and antagonists vs other three receptors. Typically, the functional activity of A2B receptor is deduced by the absence of effects of the selective agonists and antagonists at other three adenosine receptors, while eliciting response with NECA, a potent and non-selective adenosine receptor agonist. Usually, the role of A2B receptor on a given cell type, is identified when the following unique order of agonist potency is observed; NECA (non-selective)>PIA (A1-selective agonist)>IB-MECA (A3-selective agonist)>CGS-21680 (A2A-selective agonist).

Adenosine's relative agonist potency against the four receptors was determined to be, A1 ($EC_{50}$-0.31 uM)>A3 ($EC_{50}$-0.29 uM)>A2A ($EC_{50}$-0.7)>A2B ($EC_{50}$-24 uM), suggesting a unique role for A2B receptor during chronic, high oxidative stress conditions, including but not limited to hyperglycemia, mast-cell activation, and gastrointestinal tract inflammation. In spite of low agonist potency of adenosine to the A2B receptor, numerous compounds with high A2B receptor antagonist potency have been reported.

Using specific agonists and antagonists, Eisai researchers demonstrated the key role of A2B receptor antagonism in inhibiting hepatic glucose production, and a potent A2B receptor antagonist and an inhibitor of glucose production in rat primary hepatocytes was also shown to lower fasting and fed glucose levels in KK-Ay mice, a well recognized model of type 2 diabetes. Thus, compounds of present invention have utility in preventing and/or treating type 2 diabetes.

A2B receptors are also present in the plasma membranes of endothelial cells and have been found to stimulate their growth. Since this will lead to growth of new blood vessels (angiogenesis). An object of this invention is to prevent and/or treat diseases characterized by abnormal blood vessel growth, such as diabetic retinopathy.

Using immuno-fluorescence techniques with a specific anti-human A2B-antibody indicated the presence of A2B receptors in human lung mast cells obtained from asthmatics by bronchoalveolar lavage cells. Thus, the compound of formula I provide a method of preventing and/or treating asthma, bronchospastic and allergic diseases as well as other obstructive airway-type diseases.

A2B receptors are found in the colon in the basolateral domains of intestinal epithelial cells, and increases chloride ion secretion in reaction to the gastrointestinal tract inflammation in diseases such as, diarrhea. Thus, the compounds of formula I provide a method to treat inflammatory gastrointestinal tract disorders including diarrhea.

SUMMARY OF THE INVENTION

The present invention comprises compounds of formula I:

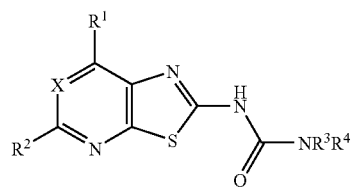

I and the pharmaceutically acceptable salts and esters thereof.

These compounds are believed to act primarily as adenosine A2B receptor antagonists and therefore to have potential for the treatment of diabetes, diabetic retinopathy, asthma, diarrhea and other pathological inflammatory conditions. The present invention comprises the compounds of formula I and their pharmaceutically acceptable salts and esters, their preparation and the preparation of medicaments containing them as well as methods for using the above mentioned compounds in the control or prevention of the above mentioned illnesses, especially asthma and diabetes.

DETAILED DESCRIPTION OF THE INVENTION

The present invention relates to compounds of the formula

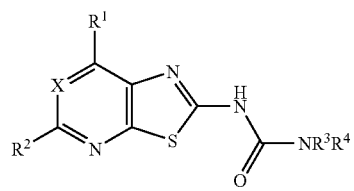

I wherein
X is C or N,
R1 is $C_{1-4}$ alkoxy,
R2 is hydrogen, hydroxy, $C_{1-2}$ alkoxy or $C_{1-2}$ alkylthio,
R3 is hydrogen or $C_{1-3}$ alkyl,
R4 is $C_{1-4}$ alkyl substituted with aryl, aroyl, aryloxy, arylsulfonyl, aralkylamino, or aroylamino,
or
R3 and R4 together with the urea nitrogen to which they are attached form a 5 to 6 membered heterocyclic ring of the formula

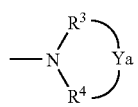

wherein R3 and R4 are both $CH_2$ or one is $CH_2$ and the other is mono-substituted with lower alkyl, Ya is a saturated or partially unsaturated alkyl segment of 2 to 3 ring carbons which is substituted with an aromatic substituent selected from the group consisting of aryl, aralkyl, aroyl, aryloxy, arylsulfonyl, aralkylamino, aryloxyalkyl, aryloxyalkylamino and aroylamino, and Ya may additionally have 0, 1 or 2 non-aromatic substituents selected from hydroxy, amino, lower alkylamino, lower alkanoylamino, cyano, carboxy, hydroxyalkylamino, carbamoyl and lower alkylcarbamoyl, or R3 and R4 together with the urea nitrogen to which they are attached form a 5 to 6 membered heterocyclic ring of the formula

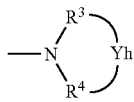

wherein R3 and R4 are both $CH_2$ or one is $CH_2$ and the other is mono-substituted with lower alkyl, Yh is a saturated heteroalkyl segment of 2 to 3 ring atoms one of which is a heteroatom, and Yh is substituted with one aromatic group which in the case of a carbon ring atom is selected from the group consisting of aryl, aralkyl, aralkyloxy, aroyl, aryloxy, arylsulfonyl, aralkylamino, aryloxyalkyl, aryloxyalkylamino and aroylamino or, in the case of nitrogen, is selected from the group consisting of aryl, aralkyl, aroyl, arylhydroxymethylalkyl, arylcarboxymethylalkyl, arylalkoxymethylalkyl, arylsulfonyl and aryloxyalkyl, or R3 and R4 together with the urea nitrogen to which they are attached form a piperidinyl or pyrrolidinyl which is benz-fused to unsubstituted or mono- di- or tri-substituted phenyl, or R3 and R4 together with the urea nitrogen to which they are attached form a piperidinyl which is spiro-fused to a 5 to 6 membered saturated heterocyclic ring containing from 1 or 2 heteroatoms which heterocyclic ring is bound or benz-fused to an unsubstituted or mono- di- or tri-substituted phenyl, and said heterocyclic ring may additionally have 0,1 or 2 non-aromatic substituents selected from lower alkyl, acyl and loweralkylsulfonyl;

or

R3 and R4 together with the urea nitrogen to which they are attached form a 5-substituted 2,5-diaza-[2.2.1]-bicyclo-heptane or 5-substituted 2,5-diaza-[3.3.0]-bicyclooctane wherein the 5-substituent is selected from the group consisting of aryl, aralkyl, aroyl, arylsulfonyl, aryloxyalkyl, and arylhydroxymethylalkyl, arylcarboxymethylalkyl, arylalkoxymethylalkyl, or the pharmaceutically acceptable salts and esters of the foregoing compounds.

Preferred compounds of formula I are:

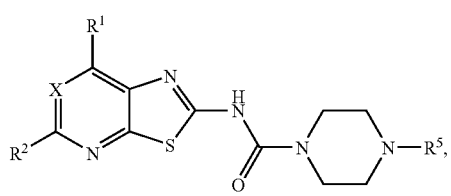

II wherein R5 is aryl, aralkyl, aroyl, aryloxyalkyl, arylsulfonyl, arylaminoalkyl or aroylaminoalkyl,

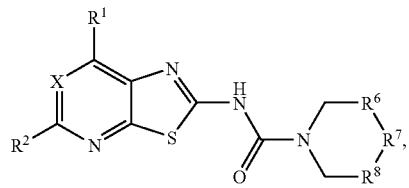

III wherein one of R6-R8 is $CH_2$, one of R6-R8 is $CH_2$ or CH(OH) and one of R6-R8 is substituted with one aromatic substituent or is disubstituted with one aromatic substituent and one non-aromatic substituent, wherein said aromatic substituent is selected from aryl, aralkyl, aralkyloxy, aroyl, aryloxy, arylsulfonyl, aralkylamino, aryloxyalkyl, aryloxyalkylamino and aroylamino, and said non-aromatic substituent is selected from hydroxy, cyano, amino, lower alkylamino, lower alkanoylamino, carboxy, hydroxyalkylamino, carbamoyl and lower alkylcarbamoyl,

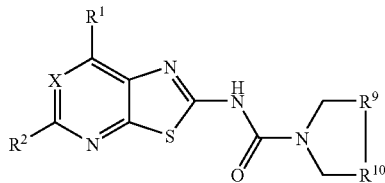

IV wherein one of R9 and R10 is $CH_2$ and the other is substituted with one aromatic substituent or is disubstituted with one aromatic substituent and one non-aromatic substituent, wherein said aromatic substituent is selected from aryl, aralkyl, aralkyloxy, aroyl, aryloxy, arylsulfonyl, aralkylamino, aryloxyalkyl, aryloxyalkylamino and aroylamino, and said non-aromatic substituent is selected from hydroxy, cyano, amino, alkylamino, carboxy, hydroxyalkylamino, carbamoyl and lower alkylcarbamoyl, and

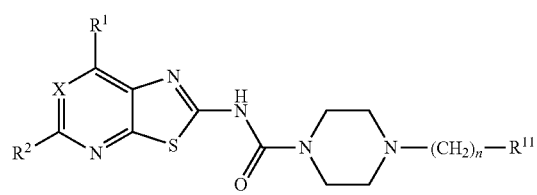

V wherein

R11 is aryl, aroyl, aryloxy or arylsulfonyl and n is 1-4.

Preferred compounds of Formula I having a spiro-fused piperidinyl group are:

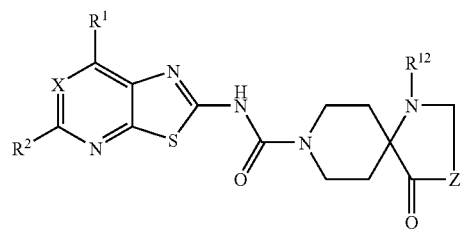

VI wherein Z is carbon or nitrogen, and R12 is unsubstituted or mono-, di- or tri-substituted phenyl,

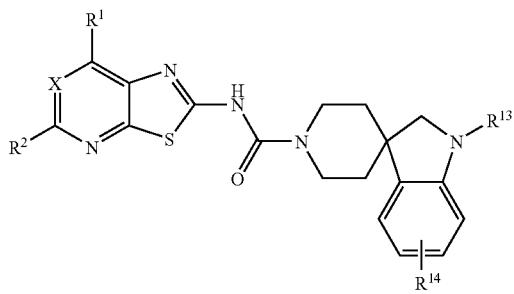

VII wherein R13 is hydrogen, lower alkyl or lower alkylsulfonyl, and R14 is hydrogen, halo, lower alkyl or lower alkylsulfonyl,

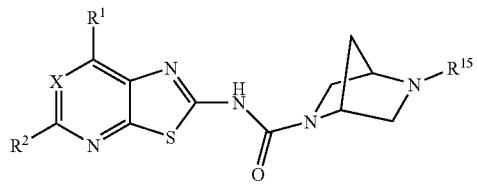

VIII wherein R15 is selected from the group consisting of aryl, aralkyl, aroyl, aryloxy, arylsulfonyl, aralkylamino, aryloxyalkyl, aryloxyalkylamino, aroylamino, and arylhydroxymethylalkyl, arylcarboxymethylalkyl and arylalkoxymethylalkyl, and

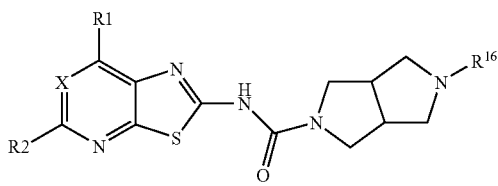

IX wherein R16 is selected from the group consisting of aryl, aralkyl, aroyl, aryloxy, arylsulfonyl, aralkylamino, aryloxyalkyl, aryloxyalkylamino, aroylamino, arylhydroxymethylalkyl, arylcarboxymethylalkyl and arylalkoxymethylalkyl.

For the compounds of Formulae I-IX, R1=methoxy or ethoxy is preferred, with methoxy most preferred. R2 is preferably hydrogen or hydroxy.

In this specification "alkyl" denotes a straight-chained, branched or wholly or partially cyclic aliphatic hydrocarbon.

The term "lower alkyl", alone or in combination (for example, as part of "lower alkoxy," "lower alkanoyl," "lower alkylamino," etc. defined below), means an alkyl group containing a maximum of six carbon atoms. "Haloalkyl" and "hydroxyalkyl" refer to the substituted lower alkyl.

The term "acyl" denotes —C(O)-lower alkyl.

The term "heteroatom" means N, O or S.

The term "heterocycle" or "heterocyclic ring" means a saturated or partially unsaturated mixed carbon and heteroatomic moncyclic or bicyclic ring. Preferred heterocyclic rings are 5 to 6 membered monocyclic or 7 to 8 membered bicyclic rings containing 1-3 heteroatoms.

The term "aryl" means a substituted or unsubstituted 5 to 6 membered monocyclic aromatic ring which may be entirely carbocyclic or may contain one, two, or three ring heteroatoms. Aryl can be substituted with one, two, three or four substituents. Preferably each substituent is independently hydroxy, carboxy, nitro, nitrile, lower alkyl, lower alkoxy, halogen, haloalkyl, haloalkoxy, hydroxyalkyl, amino, or lower alkylamino. Examples of aryl moieties include, but are not limited to, optionally substituted phenyl, optionally substituted thiazolyl, optionally substituted pyrazinyl, optionally substituted pyrrolyl, optionally substituted pyrazinyl, optionally substituted pyridinyl, optionally substituted pyrimdinyl, and the like.

The term "cycloalkyl" means a substituted or unsubstituted 5 to 6 membered monocyclic aliphatic ring which may be entirely carbocyclic or may contain one, two, or three ring heteroatoms. Substituents of cycloalkyl are preferably lower alkyl, oxo, or substituted or unsubstituted phenyl.

The term "aralkyl", signifies a lower alkyl or cycloalkyl group as previously defined in which one hydrogen atom has been replaced by an aryl group as previously defined, or additionally in the case of cycloalkyl, where two adjacent carbons are benz-fused to substituted or unsubstituted phenyl to form a bicyclic radical.

The term "aryloxy" means an aryl group which is bound to the rest of the molecule via an oxygen atom. The preferred aryloxy group is phenoxy. "Aryloxyalkyl" means a lower alkyl substituent in which one hydrogen atom has been replaced by an aryloxy group.

The term "aralkyloxy" means an aralkyl group as defined which is bound to the rest of the molecule via an oxygen atom.

The term "arylhydroxymethylalkyl" means a lower alkyl substituent one carbon of which has been substituted with both an aryl and a hydroxymethyl group.

The term "arylcarboxyalkyl" means a lower alkyl substituent one carbon of which has been substituted with both an aryl and a carboxymethyl group.

The term "arylalkoxyalkyl" means a lower alkyl substituent one carbon of which has been substituted with both an aryl and a alkoxymethyl group.

The term "aroyl" means an aryl group as defined bound to the rest of the molecule via a carbonyl group. Examples of aroyl groups are benzoyl, 3-cyanobenzoyl, and the like.

The term "arylsulfonyl" means an aryl group bound to the rest of the molecule through the sulfur atom of a sulfonyl group.

The term "aralkylamino" means an aralkyl group bound to the rest of the molecule through the nitrogen atom of an amino group.

The term "aroylamino" means an aroyl group bound to the rest of the molecule through the nitrogen atom of an amino group.

The term "lower alkoxy" means a lower alkyl group bound through an oxygen atom. Examples of unsubstituted lower alkoxy groups are methoxy, ethoxy, n-propoxy, isopropoxy, n-butoxy, tert-butoxy and the like. "Haloalkoxy" is lower alkoxy substituted with halogen.

The term "carbamoyl" means the carboxamide subsitituent —C(O)—NH$_2$. The term "lower alkylcarbamoyl" means that one or both hydrogen atoms of the amide are independently substituted with lower alkyl.

The term "lower alkanoyl" means lower alkyl groups bonded to the rest of the molecule via a carbonyl group and embraces in the sense of the foregoing definition groups such as formyl (methanoyl), acetyl, propionyl and the like. "Lower alkanoylamino" means a lower alkanoyl group bonded to the rest of the molecule via an amino group. "Lower alkylamino" means a lower alkyl group bonded to the rest of the molecule via an amino group.

The term "halogen" means an atom selected from chlorine, fluorine and bromine.

"$IC_{50}$" refers to the concentration of a particular compound required to inhibit 50% of a specific measured activity. $IC_{50}$ can be measured, inter alia, as is described subsequently.

"Pharmaceutically acceptable ester" refers to a conventionally esterified compound of formula I having a carboxy group, which esters retain the biological effectiveness and properties of the compounds of formula I and are cleaved in vivo (in the organism) to the corresponding active carboxylic acid. Thus, wherever carboxy is denoted herein, it is understood that the compounds of Formula I also embrace the corresponding pharmaceutically acceptable esters thereof.

Information concerning esters and the use of esters for the delivery of pharmaceutical compounds is available in Design of Prodrugs. Bundgaard H ed. (Elsevier, 1985). See also, H. Ansel et. al., Pharmaceutical Dosage Forms and Drug Delivery Systems (6th Ed. 1995) at pp. 108-109; Krogsgaard-Larsen, et. al., Textbook of Drug Design and Development (2d Ed. 1996) at pp. 152-191.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456-1457.

Compounds of formula (I) can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained by methods that are well known in the art for example by resolution of the racemates, by asymmetric synthesis or asymmetric chromatography (chromatography with a chiral adsorbent or eluant). The invention embraces all of these forms.

The compounds of formula (I) can be manufactured by the methods given below, by the methods given in the examples or by analogous methods. Appropriate reaction conditions for the individual reaction steps are known to the person skilled in the art. Starting materials are either commercially available or can be prepared by methods analogous to the methods given below or in the examples or by methods known in the art.

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula (I) and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives. Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile the compound could be administered with one or several daily dosage units, e.g. in 1 to 4 dosage units to provide a therapeutically effective amount thereof.

The following reaction scheme and narrative therewith sets forth the general methodology for making the novel compounds of the present invention.

The ureas of formula I, wherein X=N or C can be prepared via the coupling of the corresponding thiazolo pyrimidine/pyridine amine 2 with various amines using standard methods. For example, the pyrimidine/pyridine amine 2 can be converted in situ to the corresponding carbamoyl derivative using triphosgene or phosgene, which can then react with the amine of interest. In addition, phenyl carbamate derivatives corresponding to thiaozolo pyrimidine/pyridine amines, 3 can also be used to couple to variously substituted amines (Scheme 1).

Scheme 1

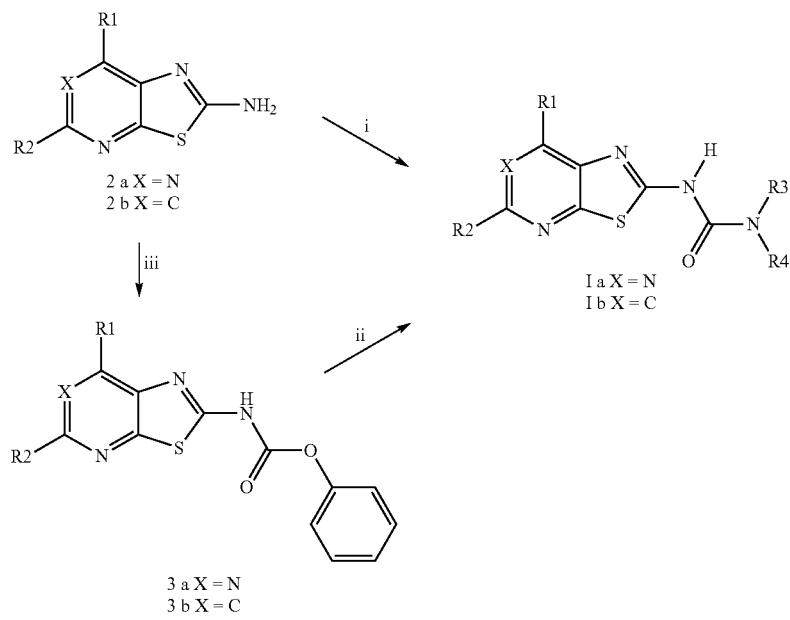

i) Triphosgene/phosgene, (R3)(R4)NH;
ii) (R3)(R4)NH, Acetonitrile reflux,
iii) Phenoxy carbonyl chloride The synthesis amine precursors, 2 that can be used to prepare the compounds of formula I are shown in Schemes 2-6. The Scheme 2 illustrates the synthesis of thiazolopyrimidine amines 2a, wherein R2 is H. These compouds are readily accessible starting from commercially available 4,6-dichloro-5-amino pyridine in three simple chemical reactions involving condensation with benzoyl isocyanate, a base-catalyzed hydrolysis of benzoyl group and a chlorine displacement reaction with lower alkyl alkoxides corresponding R1.

Chem. 2004, 41(4), 581-585), which can be nitrated under standard conditions. The nitrated pyrimidine derivative can then be chlorinated using reagents such as phosphorous penta chloride. The thiocyanate group and various lower alkyl alkoxides can then be introduced via the displacement of chlorines, in a sequential manner. The target molecules of the formula 2a, can then be obtained via the standard thiazole forming reaction, i.e, the reduction of nitro to amino group, which undergoes ready cyclization to form the thiazole ring.

Scheme 2

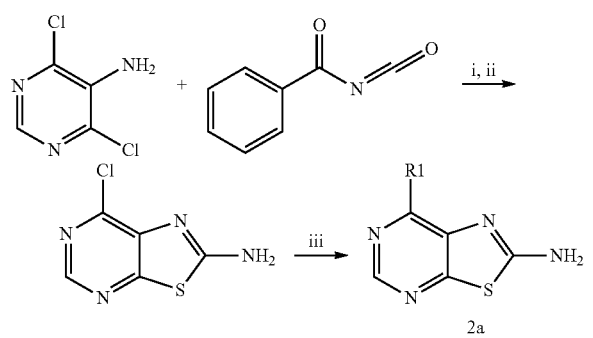

i) Condensation,
ii) Hydrolysis,
iii) Alkoxide displacement

Compunds of formula 2a, wherein R2 is lower alkyl thio ether can be prepared as shown in Scheme 3. The sequence begins with the nitration of 2-lower alkyl thienyl-4,6-dihydroxy-pyrimidine. The appropriately substituted lower alkyl thio substiuted pyrimidines are readily accessible from the litreature methods (see for eg., J. Med. Chem, 1984, 27(12), 1621-9; PCT Int. Appl. 2001092263, 06 Dec. 2001; J. Het.

Scheme 3

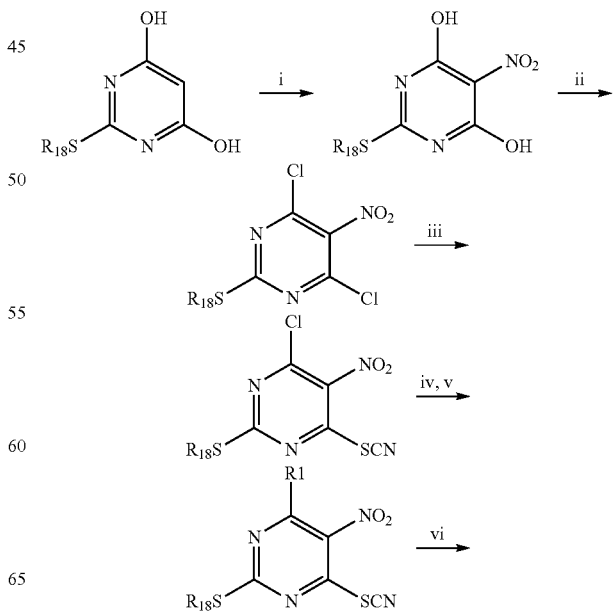

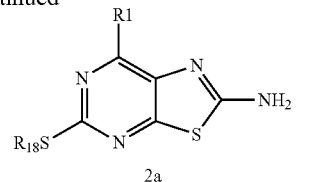

R18 = Lower alkyl
i) Nitration,
ii) Chlorination,
iii) Displacement with thiocyante,
iv) Dispacement with lower alkyl alcohol
v) Reduction of nitro group,
vi) cyclization Compunds of formula 2a, wherein R2 is lower alkyl ether or a hydoxy group can be prepared as shown in Scheme 4. The sequence begins with protection of the 2-amino group of the compound of formula 2a, wherein R2 group is a lower alkyl thio ether. The 2-amino-protected pyrimidino-thiazole compound can then be oxidized using standard methods of thio ether oxidation to the corresponding alkyl sulfone derivative. The alkyl sulfone can then be displaced with lower alkyl alkoxide or the hydroxide, and the deprotection of the amine would lead to the target molecules of the formula 2a wherein the R2 group is lower alkyl ether or a hydroxide (see for e.g, Bioorganic & Medicinal Chemistry Letters, 2002, 12(1), 81-84; Tetrahedron 2000, 56(27), 4739-4745).

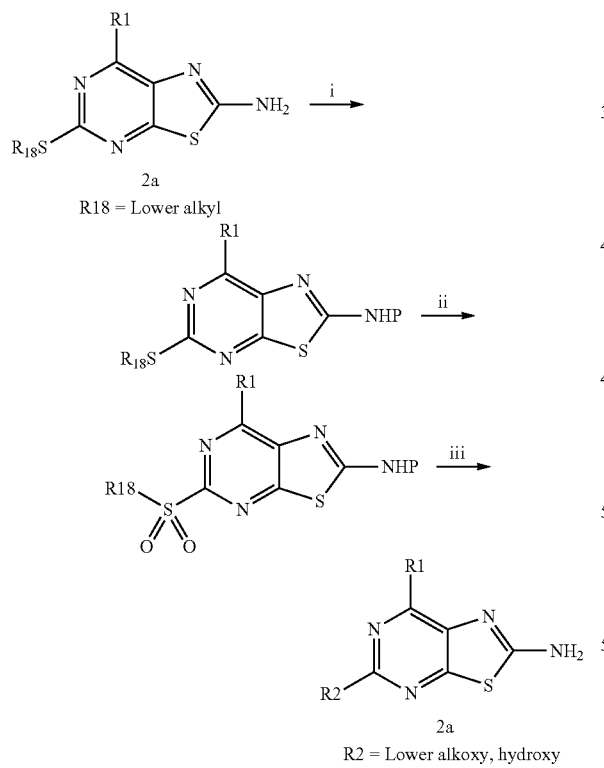

i) Protection of the amine,
ii) Oxidation of alkyl thio group,
iii) Displacement with lower alkyl alkoxides, or hydrox Compunds of formula 2b, (X=C) wherein R2 is H as shown in Scheme 5. The sequence begins with the displacement of bromine in 4-bromo-3-nitropyridine with lower alkyl alkoxides, and the resulting pyridine derivative can then be reduced and chlorinated using standard conditions. The 4-alkoxy-3-amino-2-chloropyridine can be heated to reflux in a suitable solvent in the presence of ammonium thiocyanate to yield the compounds of formula 2b, where R2 is H.

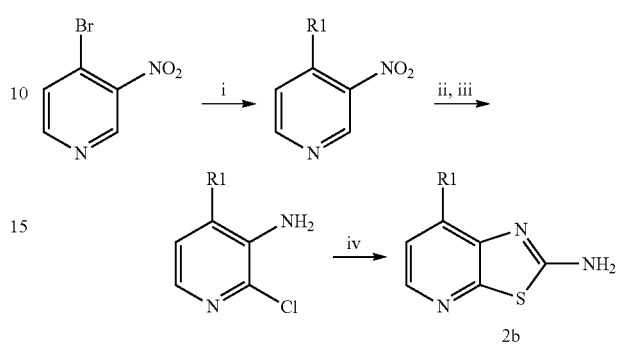

i) Displacement with Lower alkyl alkoxide,
ii) Reduction (Nitro to amino),
iii) Chlorination,
iv) Ammonium thiocyanate condensation and cyclization Compunds of formula 2b, wherein R2 is lower alkyl thio ether, lower alkyloxy or hydroxy group can be prepared as shown in Scheme 6. The sequence begins with the simultaneous etherification and esterifcation of chelidamic acid with appropriate lower alkyl alcohol under acidic conditions, similar to those reported by Inouye et al (J. Amer. Chem. Soc, 1995, 117, 12416-12425). The resulting ether/diester pyridine can then be converted to the corresponding 2,6-dibromopyridine derivative via the sequential hydrolysis followed by the Barton-modified Hunsdieker reaction (Barton et al, Tetrahedron, 1985, 41, 3901-3924). The dibromo pyridine derivative can be nitrated under standard nitration conditions to yield the corresponding nitro pyridine derivative, from which following similar reaction sequence described earlier in Schemes 3 and 4, the compound of formula 2b wherein R2 is lower alkyl thio ether, lower alkyl sulfone, lower alkyloxy, or hydroxy can be prepared.

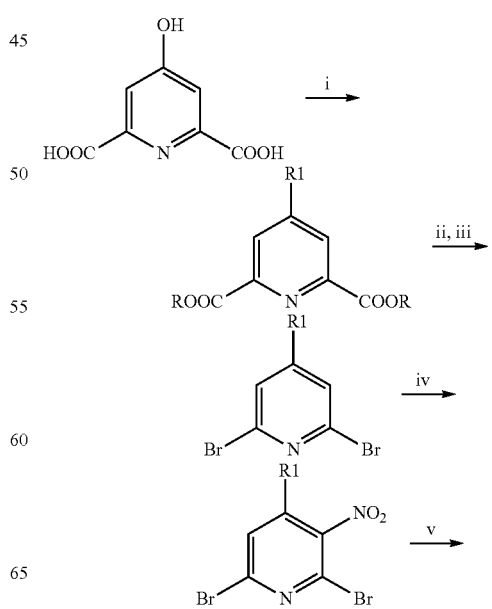

-continued

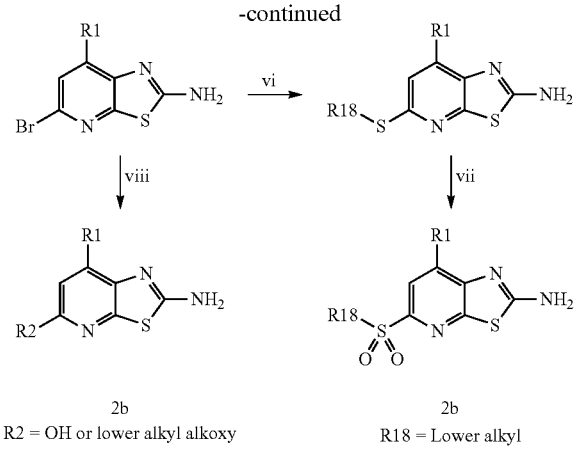

2b
R2 = OH or lower alkyl alkoxy

2b
R18 = Lower alkyl i) Esterification and etherification with lower alkyl alcohol/s,
ii) Hydrolysis of esters,
iii) Barton modified Hunsdiecker reaction,
iv) nitration,
v) Ammonium isothiocyanate condensation,
vi) Displacement with lower alkyl thiolate,
vii) oxidation of thio ether,
viii) Displacement with lower alkyl aloxide or hydroxide The compounds of formula I wherein R3 and R4 groups can be joined to form variously substituted 5 or 6 membered rings. For 6 membered amines that includes a nitrogen atom can be a piperizine ring. The piperizine ring containing compounds of formula I can be prepared following the reactions shown in Scheme 7 via the intermediate 4.

Compounds of formula 6, where R19 is H or a lower alkyl group or substituted alkyl can be prepared using reductive amination procedures, wherein the appropriately substituted aryl or heteroaryl aldehyde or ketone is reacted with intermediates 4, and the in situ reduction of the piperazine, with a reducing agent, for example sodium cyanoborohydride. The intermediate compounds of formula 4 are readily accessible via the reaction sequence shown in Scheme 1. Compounds of formula 7, where the position 4 nitrogen of piperizine is substituted with various acyl and sulfonyl groups, can be readily prepared by coupling of acyl or sulfonyl halides with the piperizine ureas, 4. In addition, compunds of formula 6 can also be prepared by the following the reactions shown Scheme 8, wherein appropriately substituted piperazines can be converted to the target comounds directly coupling with thiozole pyrimidine/pyridine amines 2 using the reaction sequence shown in Scheme 1.

Scheme 8

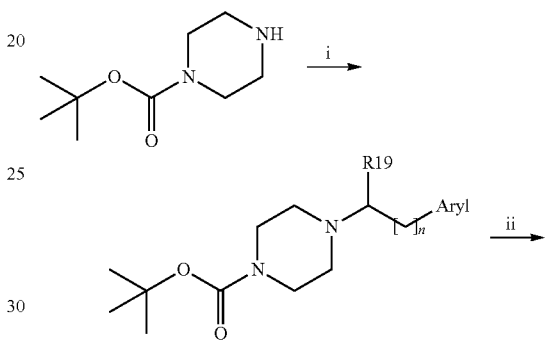

Scheme 7

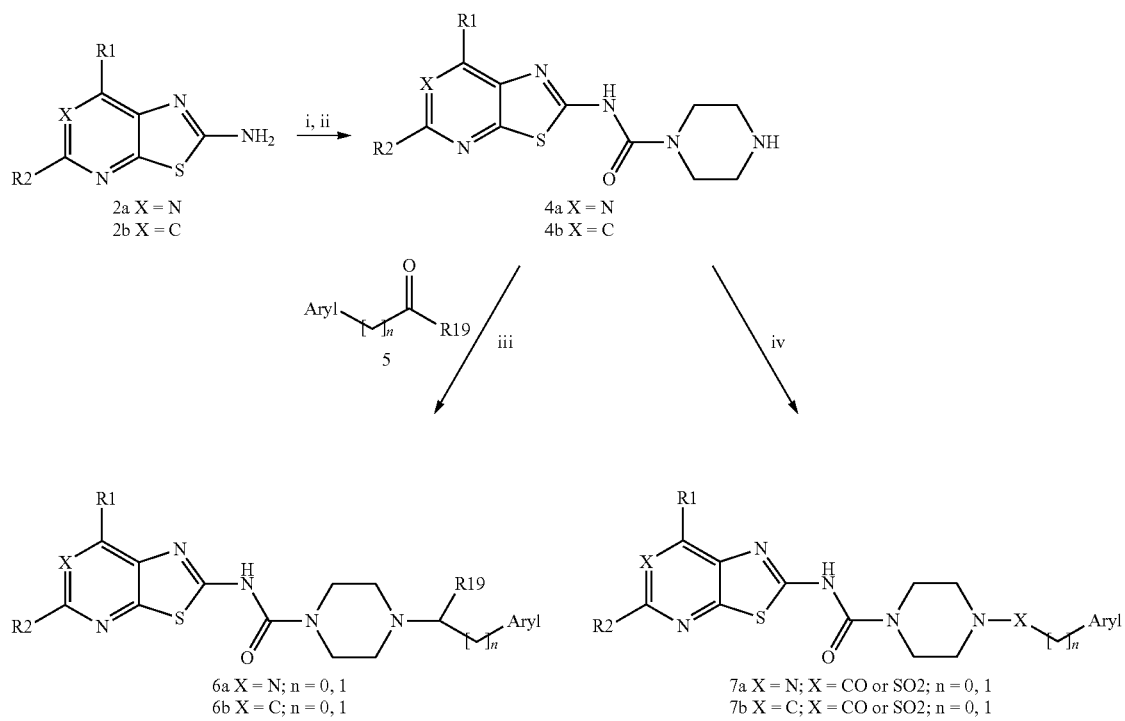

2a X = N
2b X = C

4a X = N
4b X = C

6a X = N; n = 0, 1
6b X = C; n = 0, 1

7a X = N; X = CO or SO2; n = 0, 1
7b X = C; X = CO or SO2; n = 0, 1 i) Coupling (see Scheme 1) with Boc-piperizine,
ii) TFA or HCl,
iii) Reductive amination with 5 (R19 = H, lower alkyl, or caboxyalkyl, hydroxy alkyl),
iv) Codensation with aryl akyl sulfonyl chloride -continued

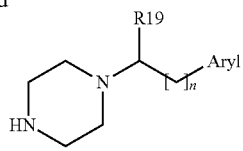

i) Reductive amination,
ii) HCl or TFA

The compounds of formula I wherein R3 and R4 groups can be joined to form a piperizine ring which is substituted at the distal nitrogen with a alpha-branched aralkyl groups. These groups can be an ester, or hydroxy methyl, or lower alkoxy methyl (compouds 9, 10, and 11 respectively). These compounds can be prepared according the scheme 9, as shown, following well precedented reactions.

piperidinone and its reaction with aryl Grignard reagents (Scheme 10).

Scheme 10

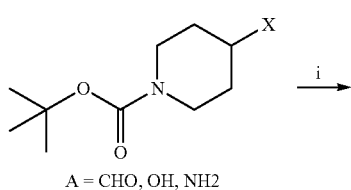

A = CHO, OH, NH2

Scheme 9

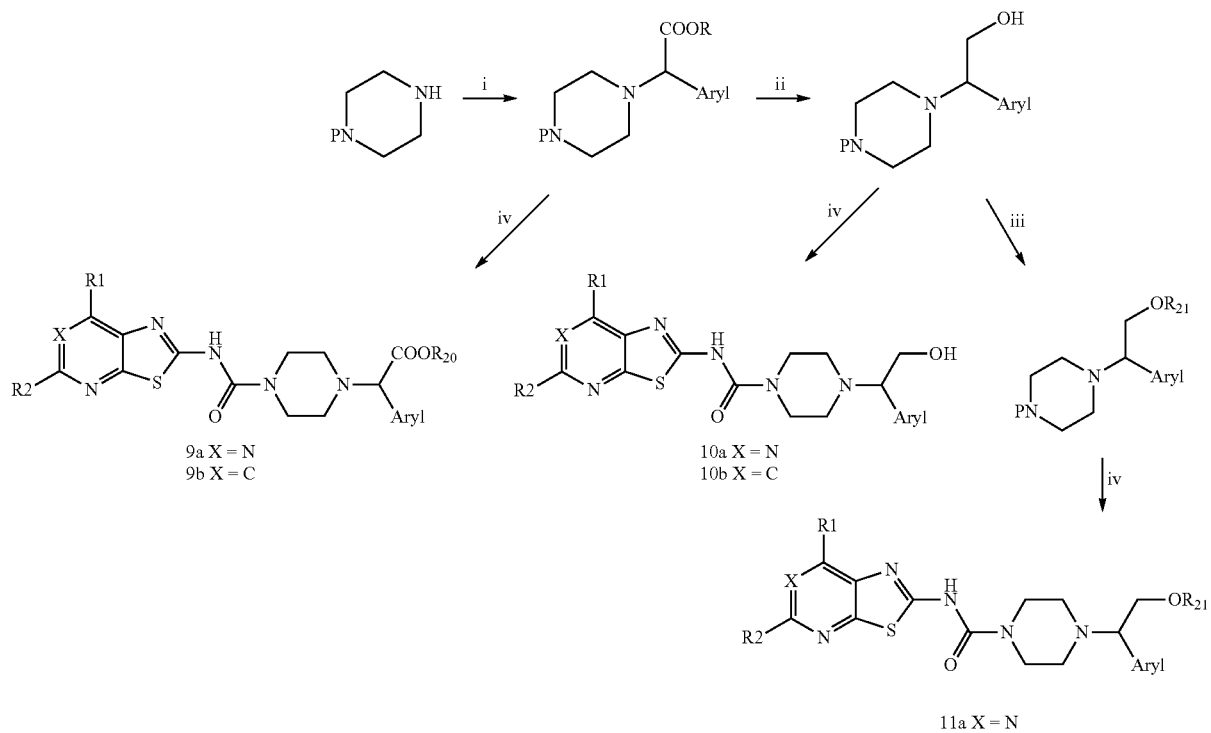

i) Alkylation with a-bromoarylacetic acid ester (R20 = lower alkyl),
ii) Reduction,
iii) O-alkylation (R21 = lower alkyl) iv) See Scheme 1

Compounds of formula I wherein R3 and R4 are joined to form 6 membered piperidine ring 12, can be prepared from the readily available reagents. Appropriately substituted piperidines can be prepared from literature methods, for example, the amides and amino-alkyl derivatives can be prepared from the readily available 4-amino-piperidine via condensation with appropriate aryl carboxylic acid and reductive amination reactions, respectively. Similarly, the the ether and sulfonyl linked piperidines can also be prepared from the 4-hydroxy-piperidine, via the substitution reaction with an aryl alkoxide, or aryl thioalkoxide, followed by its oxidation to sulfone, respectively. The carbon-linked piperidines are availble through organometallic chemistry using 4-benzyl- -continued

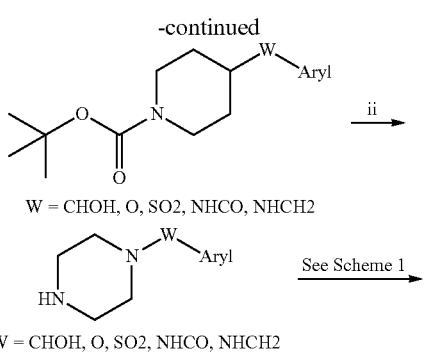

W = CHOH, O, SO2, NHCO, NHCH2

W = CHOH, O, SO2, NHCO, NHCH2

See Scheme 1

-continued

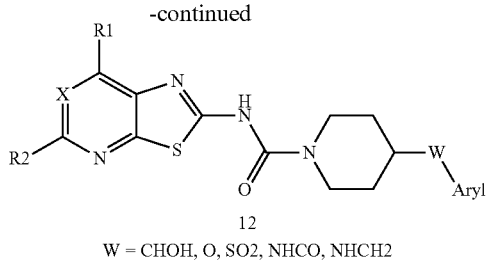

12
W = CHOH, O, SO2, NHCO, NHCH2 i) a) Aryl Grignard reaction, when A = CHO or b) Mitsnobu reaction with hydroxy aryl compounds, when A = OH; or c) reductive amination with aryl methyl amines when A = NH2; d) Amide coupling with aryl caboxylic acids, when A = NH2, e) When A = OH convert it to OMs, then react it with aryl alkyl thiols, and oxidize the thio ethers to sulfones
ii) HCl or TFA Compounds of formula I wherein R3 and R4 groups are joined to form a piperidine ring, which is substituted at 4 position with benzofused cyclic ureas and carbamates, 14 can be prepared from the general methods described before (see Scheme 1) using the appropriate piperidine derivatives. The piperidines with 4-benzofused cyclic urea or carbamates 13 can be prepared by Mitsnobu reaction (J. Med. Chem., 47(27), 6921, 2004) between the appropriately substituted benzofused cyclic ureas or carbamates and 4-hydroxy piperdine. These compounds can also be prepared from an appropriately protected 4-amino piperidine derivative, via the nucleophilic displacement of o-nitro-halo benzenes, which can then be reduced and cyclized as shown in Scheme 11 (J. Med. Chem, 57(6), 814, 1987; Tetrahedron, 57(6), 981, 2001). The benzofused cyclic ureas from 1,2-diaminobenzenes and benzofused cyclic carbamates from o-hydroxy-2-amino-benzenes, can be prepared using literature methods (Farmaco, 60(2), 127, 2005; Nuclear Medicine Communications, 25(8), 845, 2004; J. Amer. Chem. Soc, 77, 5757, 1955; Green Chemistry, 6(2), 78, 2004; J. Amer. Chem. Soc, 71, 1265, 1949).

Scheme 11

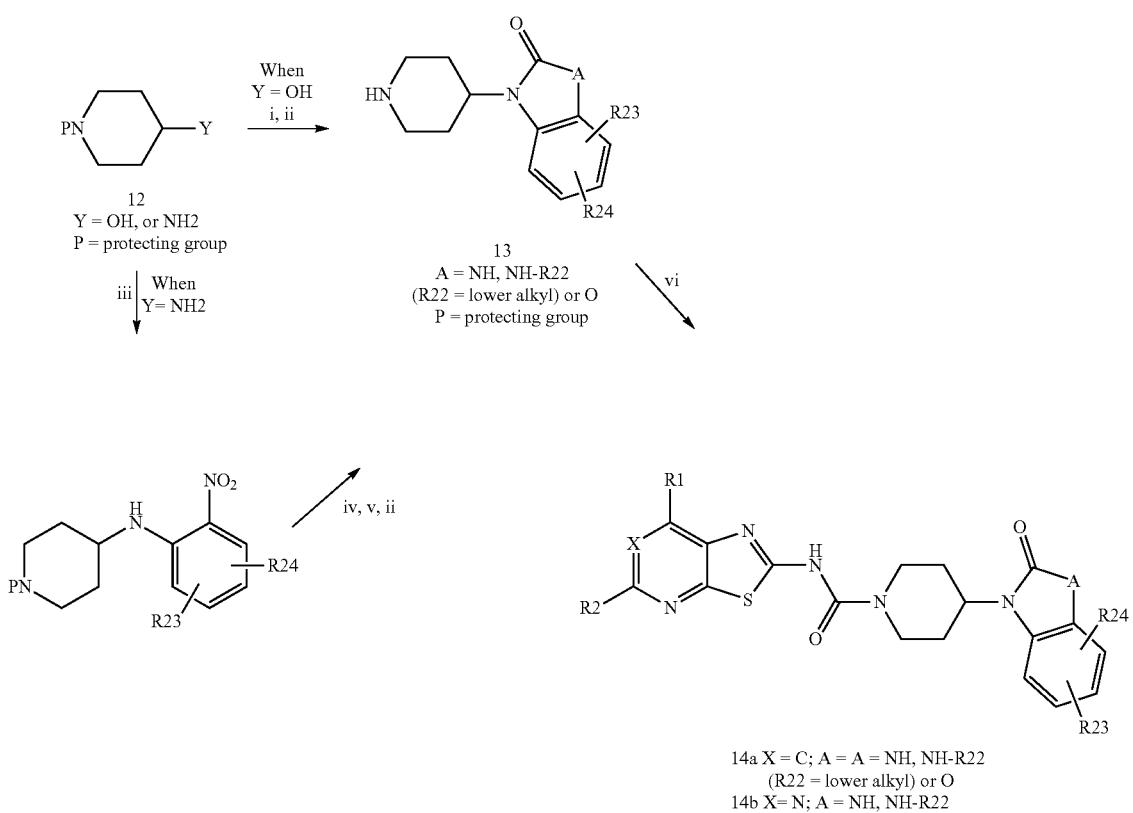

i) Benzofused cyclic urea (R23 = R24 = independently H, or lower alkyl, lower alkoxy or halogen) Mitsnobu reaction,
ii) Deprotection,
iii) Substitution reaction with o-halo-nitro-benzenze,
iv) Reduction with Raney Ni,
v) Phosgene,
vi) See Scheme 1

Compounds of formula I wherein R3 and R4 groups are joined to form a piperidine ring, which is substituted at 4 position with cyclic or acyclic amines, 15 can be prepared from the 4-piperidinone intermediate, 16 using standard reductive amination procedures (Scheme 12).

Scheme 12

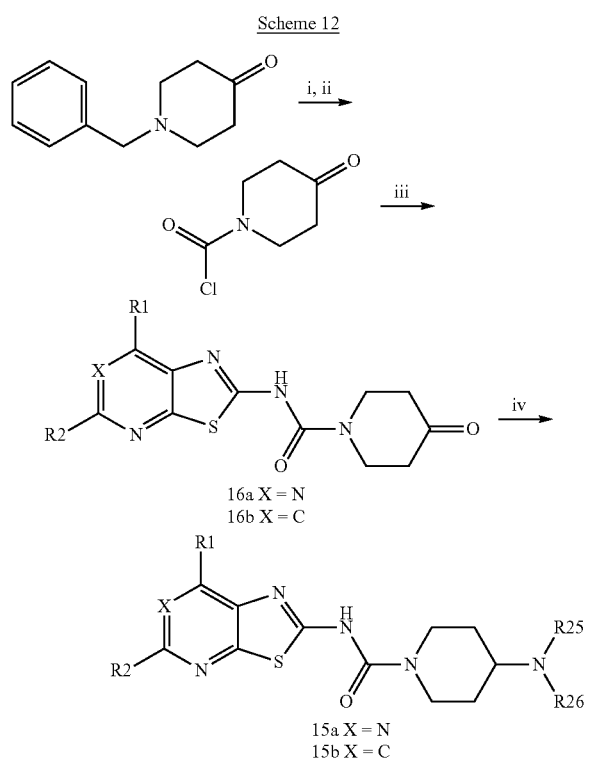

i) Pd-C/H2,
ii) Triphosgene,
iii) Coupling with 2,
iv) Reductive amination with HN(R25)(R26)

Compounds of formula I wherein R3 and R4 groups are joined to form a piperidine ring, which is substituted at 4 position with a carbinol and an aryl group 17 can either be prepared from the intermediates 16 or starting from a protected 4-piperidone derivative via Grignard addition, as shown in Scheme 13 (see for example, Eur. J. Med. Chem, 40(12), 1197, 2005; Bioorg. Med. Chem. Lett, 15(7), 1891, 2005; Eur. J. Med. Chem, 10(2), 178, 1975).

Scheme 13

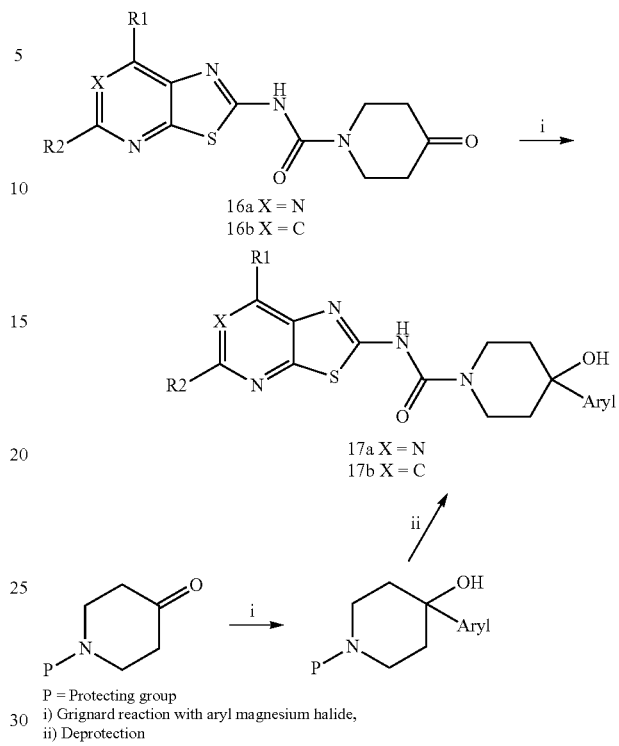

P = Protecting group
i) Grignard reaction with aryl magnesium halide,
ii) Deprotection Compounds of formula I wherein R3 and R4 groups are joined to form a piperidine ring, which is substituted at 4 position with an aryl group and various carbon linked functional groups, such as cyano 18, hydroxy methyl 19, ester 20, carboxylic acid 21, or amide derivatives 22 can be prepared starting from a protected 4-cyano-4-arylpiperidine derivative following well known reactions, as shown in Scheme 14. The 4-cyano-4-arylpiperidine derivatives are readily available following the litereature reported methods (for examples, see, J. Med. Chem, 48(5), 1336, 2005; Bioorg. Med. Chem. Lett. 14(1), 207, 2004; Bioorg. Med, Chem, 12(19), 5063, 2004; Tetrahedron, 60(22), 4875, 2004; Bioorg. Med. Chem. Lett, 11(14), 1959, 2001; Eur. Pat. Appl. 924196, 23 Jun. 1999; Org. Prep. And Proc. Int. 28(4), 478, 1996; J. Heterocycl. Chem. 23(1), 73, 1986).

Scheme 14

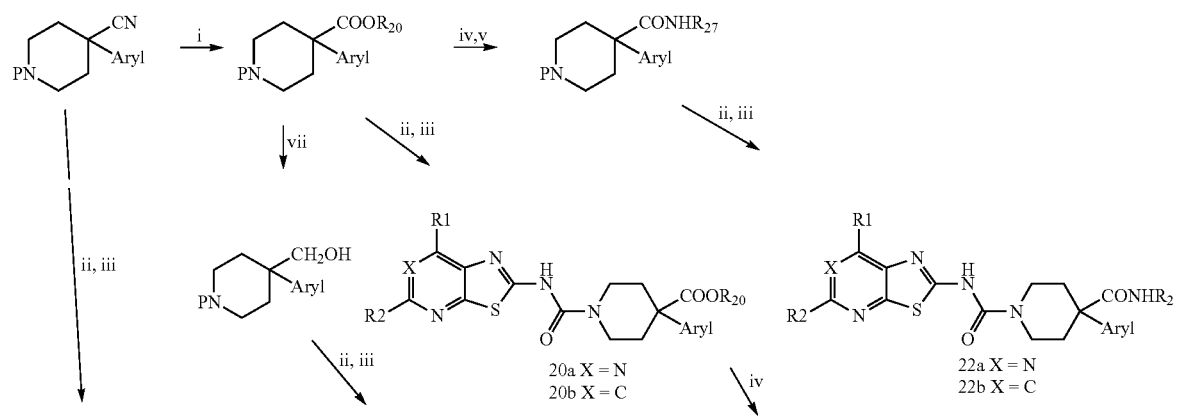

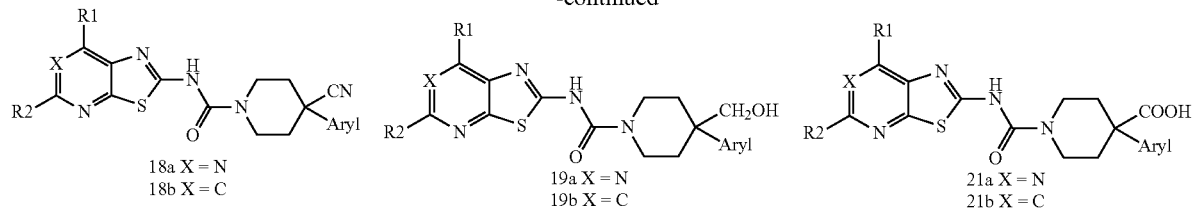

18a X = N
18b X = C

19a X = N
19b X = C

21a X = N
21b X = C i) Lower alkyl alcoholysis, acid (R20 = lower alkyl);
ii) Deprotection,
iii) See Scheme I,
iv) Hydrolyis,
v) amide coupling (R27 = lower alkyl)

Compounds of formula I wherein R3 and R4 groups are joined to form a piperidine ring, which becomes part of the spiroindoline ring, 23 can be prepared starting from the appropriate spiroindoline piperidines using the similar reaction scheme described earlier (see Scheme 1). The spiroindoline piperidines can be prepared using literature methods, for example starting from aryl hydrazines and 4-formyl-piperidines (see WO9633189; U.S. Pat. No. 5,723,616, 1998; Tetrahedron Lett, 38(9), 1497, 1997) (Scheme 15).

23a X = N
23b X = C i) Toluene reflux, (R28 = R29 = independently H, or lower alkyl, lower alkoxy or halogen (hydrazone formation)
ii) CF3COOH (Fischer Indole synthesis),
iii) NaBH4 (Reduction of the imine),
iv) Alkylation (R22 = lower a deprotection,
vi) see Scheme 1

Scheme 15

Compounds of formula I wherein R3 and R4 groups are joined to form a piperidine or a 3,6-dihydro-2H-pyridine ring, which is substituted with 4-aryl group 24 and 25 respectively, can be prepared from the intermediates 17 which can be dehydrated using an acid catalyst to yield compounds of formula 24. The compounds of formula 24 can be hydrogentated using Pd-catalyzed hydrogenation methods to yield compounds of formula 25, as shown in Scheme 16.

Compounds of formula I wherein R3 and R4 groups are joined to form a piperidine ring that is bis-hydroxylated and has a 4-aryl substitution, 21 can be conveniently prepared from the the compounds of formula 24 via a bis-hydroxylation reaction, as shown in Scheme 16

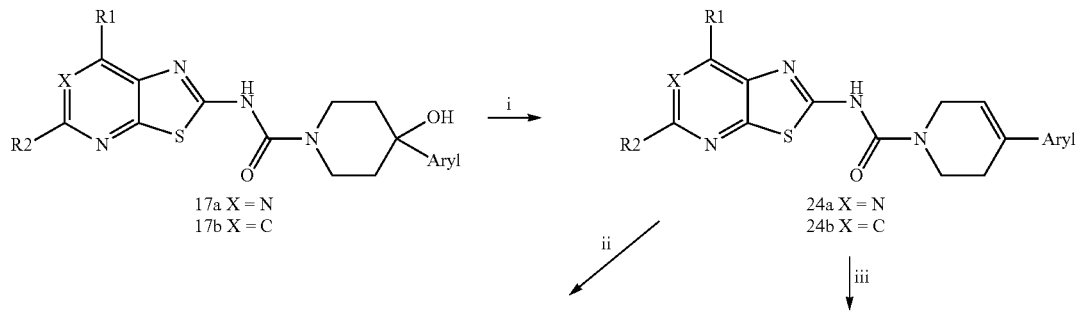

17a X = N
17b X = C

24a X = N
24b X = C

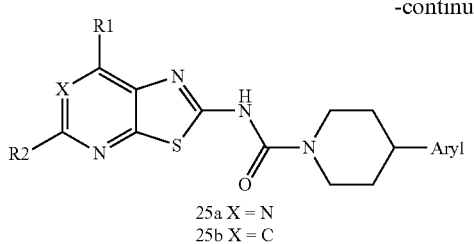

25a X = N
25b X = C

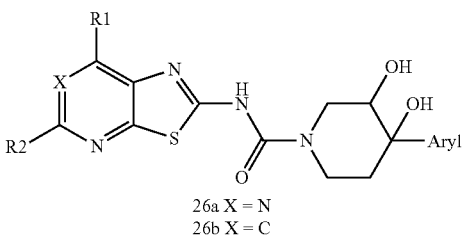

26a X = N
26b X = C i) Dehydration,
ii) Hydrogenation,
iii) Bis-hydroxylation (OsO4/NaIO4 or Epoxidation followed by base-catalyzed ring opening)

Compounds of formula I wherein R3 and R4 groups are joined to form a 3-benzyl piperidine, 27 can be prepared from the reactions shown in Scheme 17. The necessary 3-benzyl-piperidines can be readily prepared starting from pyridine-3-carboxaldehyde and aryl Grignard reagents. The resulting carbinols can be deoxygenated and pyridine ring can be saturated using catalytic hydrogenation, as reported by B. Agai et al (Tetrahedron, 59 (2003), 7897-7900). The 3-benzyl-piperidines can readily be coupled with pyrimidine/pyrimidine amines 2, as before (see Scheme 1) to yield compounds of formula I.

-continued

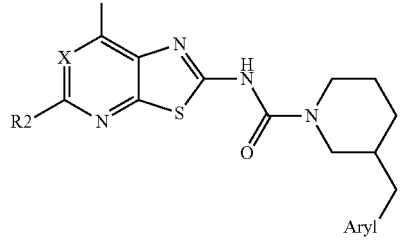

27a X = N
27b X = C i) Aryl-Mg-halide,
ii) Hydrogenation,
iii) See scheme 1

Scheme 17

Compounds of formula I wherein R3 and R4 groups are joined to form a piperidine ring which is substituted with 4-N-acetyl-4-aryl group 28 can be prepared from the compounds of formula 17 using an acid catalyzed addition of acetonitrile, the adduct of which is hydrolyzed to form compounds of formula 28 (Scheme 18). Analogous reaction with chloro acetonitrile yields the intermediate 29, which can be converted to the corresponding amine derivative 30. Thus, the compounds of the formula 30 wherein the amine can be lower alkyl alkylated 33 or lower alkyl acylated 32 or lower alkyloxy carbonylated 31 as shown in Scheme 18.

Scheme 18

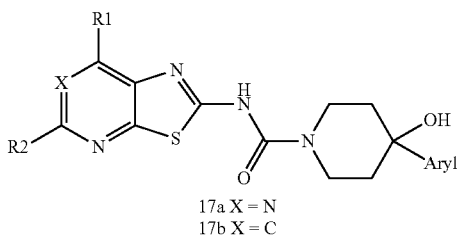

17a X = N
17b X = C

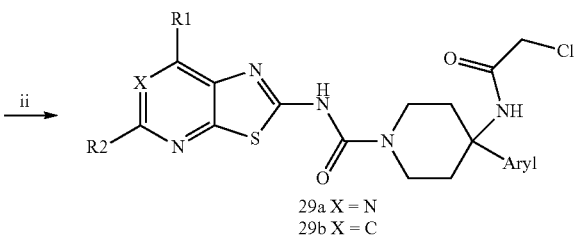

29a X = N
29b X = C

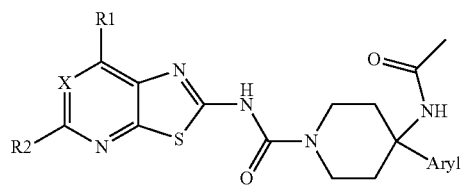

28a X = N
28b X = C

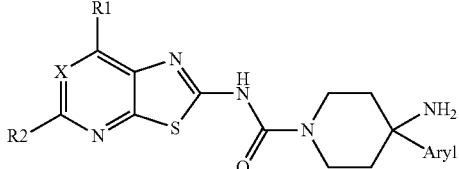

30a X = N
30b X = C

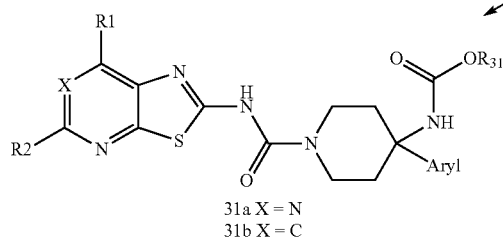

31a X = N
31b X = C

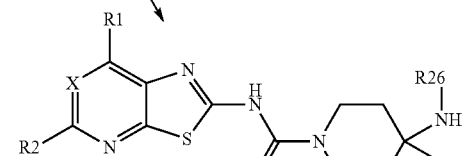

33a X = N
33b X = C

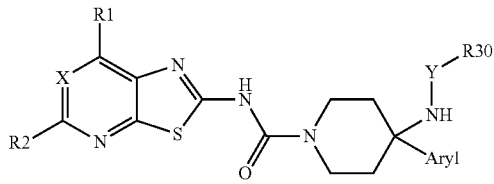

32a X = N; Y = CO or SO2
32b X = C; Y = CO or SO2 i) CH3CN/H2SO4/AcOH,
ii) ClCH2CN/H2SO4/AcOH,
iii) Thiourea/EtOH/AcOH/HCl,
iv) Reductive alkylation with R26—CHO (R26 = lower alkyl),
v) Acylation with R30—CO—Cl or R30—SO2—Cl (R30 = lower alkyl)
vi) R30—OCO—Cl, base (R31 = lower alkyl)

Compounds of formula I wherein R3 and R4 groups are joined to form a 1,3,8-triaza-spiro[4,5]decan-4-one ring system resulting in compounds of formula 34 and 35 can readily prepared from the Strecker type synthesis starting from protected 4-piperidinone, as shown in Scheme 19, according to litereature report (WO2005/040166; J. Med, Chem, 28(12), 1811, 1985; U.S. Pat. No. 199,142, 1982).

Scheme 19

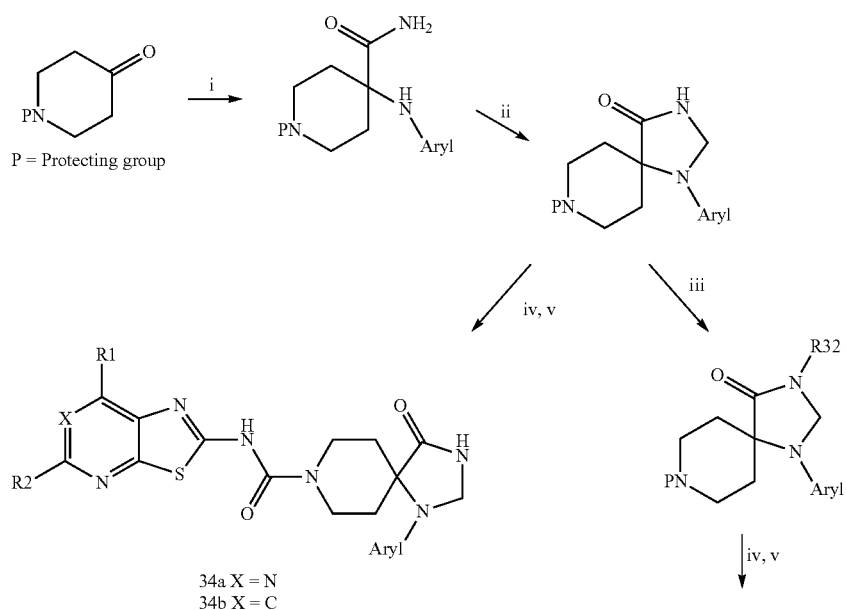

34a X = N
34b X = C

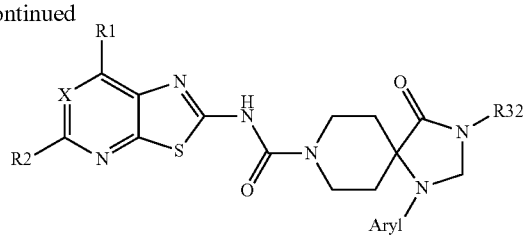

35a X = N
35b X = C i) Strecker synthesis,
ii) Triethyl ortho-formate,
iii) Alkylation (R32 - lower alkyl group),
iv) Deprotection,
v) See Scheme 1.

Compounds of formula I wherein R3 and R4 groups are joined to form a 3-benzyl pyrrolidines 36 can be prepared from phenylglycinol derived lactam (Meyers, A. I, et al J. Org. Chem, 1989, 54, 4243), as shown in Scheme 20, according to the synthetic method reported by Westrum and Meyers (Tetrahedron Lett, 1994, 973-976).

Scheme 20

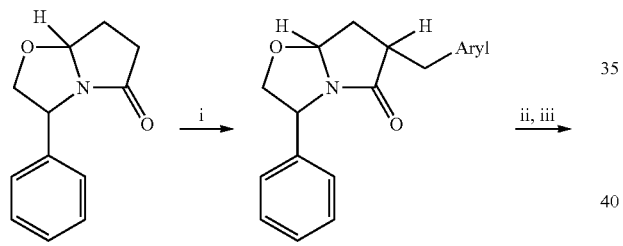

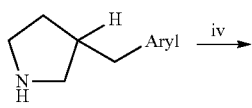

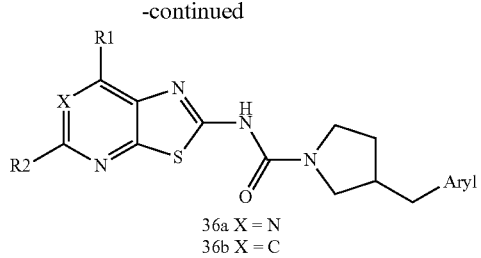

36a X = N
36b X = C i) LiHMDS, alkylation aryl-CH2-halide,
ii) Reduction with LAH,
iii) Hydrogenation,
iv) See Scheme 1

Similarly, compounds of formula I wherein R3 and R4 groups are joined to form a 3-amino, 3-amido or 3-sulfonamido-pyrrolidines 37-39, can be readily prepared from the commercially available derivatives of 3-amino pyrrolidine (Scheme 21).

Scheme 21

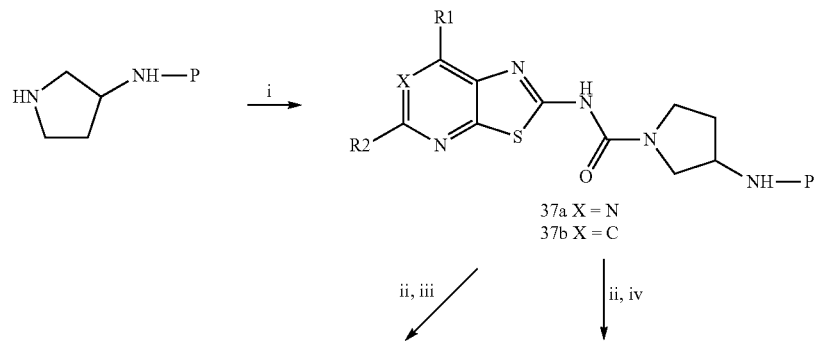

37a X = N
37b X = C

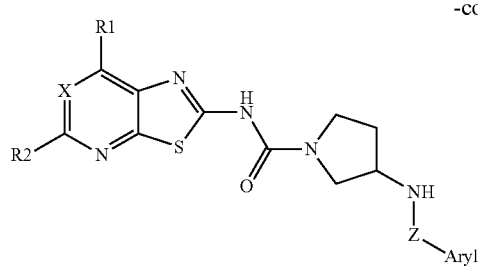
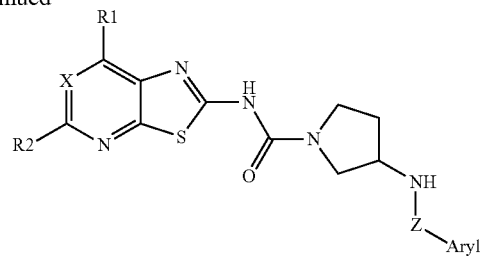

38a X = N; Z = CO, or SO₂
38b X = C; Z = CO or SO₂

39a X = N; Z = CH₂ or (CH₂)₂₋₃—O—
39b X = C; Z = CH₂ or (CH₂)₂₋₃—O—

P - Protecting group
i) See Scheme 1,
ii) Deprotection,
iii) Acyllation or sulfonylation,
iv) alkylation Compounds of formula I wherein R3 is lower alkyl or a hydrogen, and R4 is a lower alkyl substituted with aryl, aralkyl, aroyl, aryloxy, arylsulfonyl, aralkylamino, or aroylamino group 40, can be made from the appropriately substituted amines using the reaction sequence shown in scheme 1. These differentially substituted secondary amines can be made using standard synthetic methods.

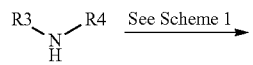

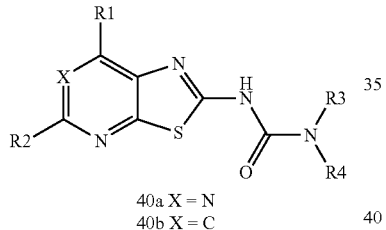

40a X = N
40b X = C

Compounds of formula I wherein R3 and R4 groups are joined to form a 3-aryl substituted morpholine ring 41, can be prepared starting from the appropriately substituted 3-aryl-morpholines, which can be prepared using literature reported methods. For example, a sequence of reactions starting from readily availabe aryl epoxides, reported by Epifani, E et al (J. Med. Chem, 1983, 26, 254-259), can be used to prepare appropriately substituted 3-aryl morpholines (Scheme 22).

Scheme 22

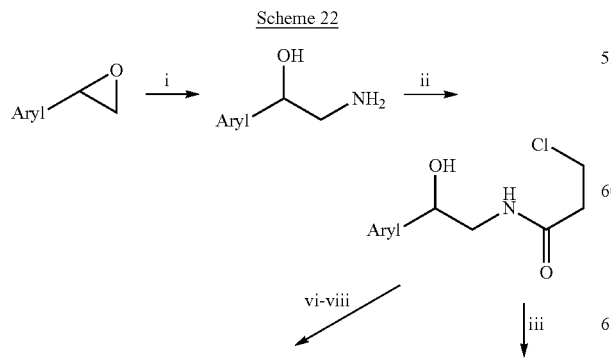

-continued

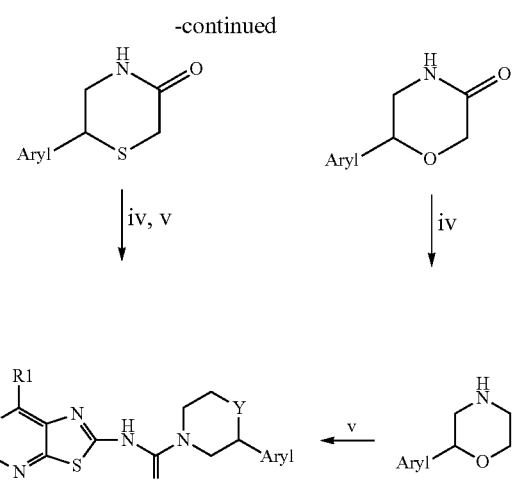

41a X = N; Y = O, S
41b X = C; Y = O, S i) ammonia,
ii) N-acylation,
iii) cyclization,
iv) reduction,
v) See Scheme 1,
vi) methane sulfonyl chloride, base,
vii) Displacement with potassium thioaceate,
viii) Base catalyzed hydrolyis of thioacetate and cyclization Compounds of formula I wherein R3 and R4 groups are joined to form a 5-substituted 2,5-diaza-[2.2.1]-bicycloheptane ring derivatives 42, 43 and 44, can be prepared starting from the appropriately 5-substituted 2,5-diaza-[2.2.1]-bicycloheptanes and 5-substituted 2,5-diaza-[3.3.0]-bicyclooctanes which can be readily prepared from commercially available reagents, using the methods described earlier (see Scheme 1).

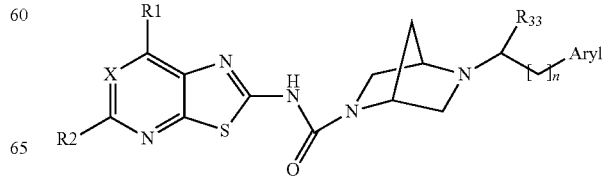

-continued

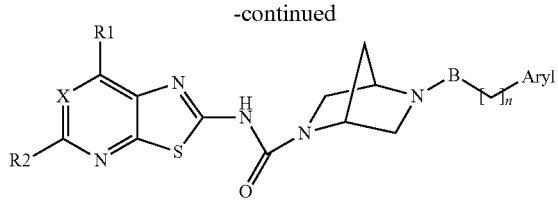

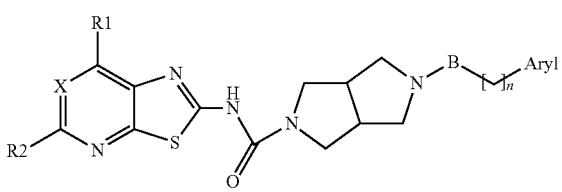

Compounds of formula I wherein R3 and R4 groups are joined to form a substituted-4-arylpiperizine ring derivative 45 can be prepared starting from the corresponding 4-arylpiperazines, using the reaction sequence shown in scheme 1. The N-arylpiperizines are readily available via several different routes including, for example, from the protected or unprotected piperazine and a halogen containing aromatic compound, see Brenner E et al (Tetrahedron, 2002, 58, 6913) and Wan Y et al (Synthesis, 2002, 1597).

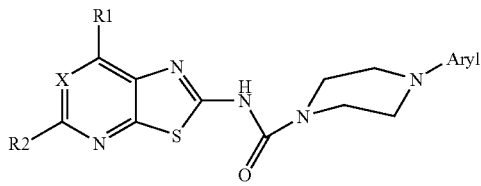

Compounds of formula I wherein R3 and R4 groups are joined to form a substituted-3-benzyl-3-carboalkoxy piperidine derivative 45 can be prepared starting from the corresponding 3-benzyl-3-carboalkoxy piperidines, using the reaction sequence shown in Scheme 1. The 3-benzyl-3-carboalkoxy piperidines can be made following the procedures reported by Maligress, P. E et al, (J. Org. Chem, 1998, 63, 9548).

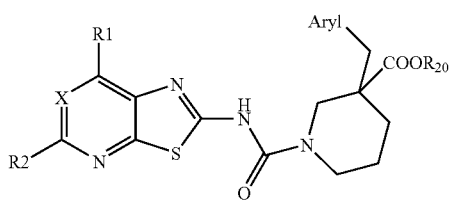

Compounds of formula I wherein R1 and R2 groups are joined to form a 1-aryl-3,8-diazaspiro[4,5]dicane-4-one derivatives 47 can be prepared starting from the corresponding 1-aryl-3,8-diazaspiro[4,5]dicane-4-ones, using the reaction sequence shown in Scheme 1. The 1-aryl-3,8-diazaspiro[4,5]dicane-4-ones can be made following the procedures reported by Van Parys, M et al, (Bull des Soc Chimiques Belges, 1981, 90, 757) or Galley, G et al (WO 01/94346 A1, 2001). Similarly, compounds of formula 48 can also be prepared from the appropriate piperidine compounds (see Tetrahedron Lett, 43(38), 6865, 2002; Helv. Chimica. Acta, 83(6), 1247, 2000; Eur. Pat. Appl. 636609, 1995).

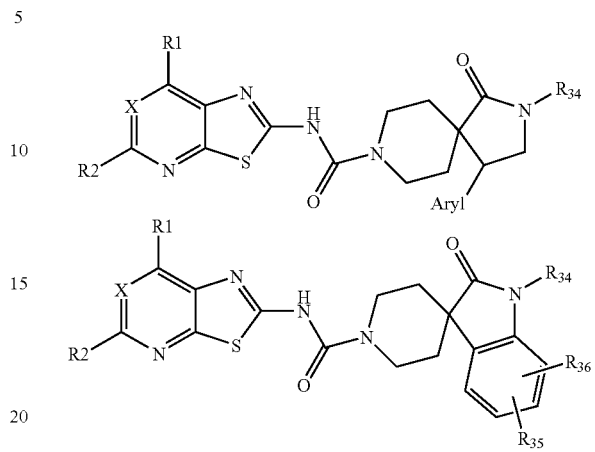

Compounds of formula I wherein R3 and R4 groups are joined to form a 3-substituted pyrrolidine derivatives 49 can be prepared starting from the corresponding 3-substituted pyrrolidines, using the reaction sequence shown in scheme 1. The 3-substituted pyrrolidine derivatives are readily available from the protected 3-hydroxy-pyrrolidine, using methods known in the art (see, e.g., Alanine, A et al., WO01/81303A1 (2001) and Sternfeld et al. J. Med. Chem., 42, 677-690 (1999)).

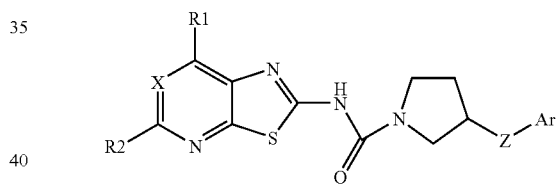

The following examples shall illustrate preferred embodiments of the present invention but are not intended to limit the scope of the invention.

EXAMPLE 1

Synthesis of 4-(3-trifluoromethyl-benzyl)-piperazine-1-carboxylic acid (7-methoxy-thiazolo[5,4-d]pyrimidin-2-yl)-amide.

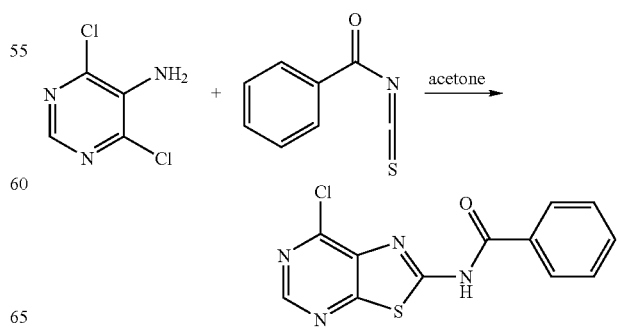

Step 1: A mixture of 5-amino-4,6-dichloro-pyrimidine (5.0 g, 30.49 mmol) in acetone (30 mL) at 25° C. was treated with benzoyl isothiocyanate (5.5 g, 33.54 mmol). The mixture was stirred at reflux for 6 h and then was cooled to 25° C. The resulting solids were collected by filtration, washed with acetone and petroleum ether and dried in vacuo to afford N-(7-chloro-thiazolo[5,4-d]pyrimidin-2-yl)-benzamide (7.87 g, 79%) as an off-white solid. The NMR spectrum obtained on the sample is compatible with its structure.

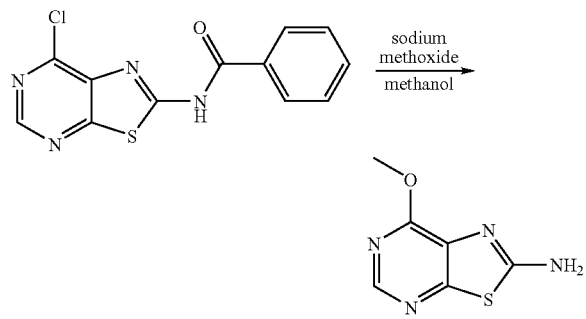

Step 2: A mixture of N-(7-chloro-thiazolo[5,4-d]pyrimidin-2-yl)-benzamide (1.0 g, 3.06 mmol) in methanol (25 mL) at 25° C. was treated with sodium methoxide (1.65 g, 30.60 mmol). The mixture was stirred at reflux for 3 d. At this time, the reaction was concentrated in vacuo. The resulting solid was dissolved in ethyl acetate, washed with water and a saturated aqueous sodium chloride solution, dried over magnesium sulfate, filtered and concentrated in vacuo to afford 7-methoxy-thiazole[5,4-d]pyrimidin-2-ylamine (385 mg, 70%) as a light yellow solid. The NMR spectrum obtained on the sample is compatible with its structure.

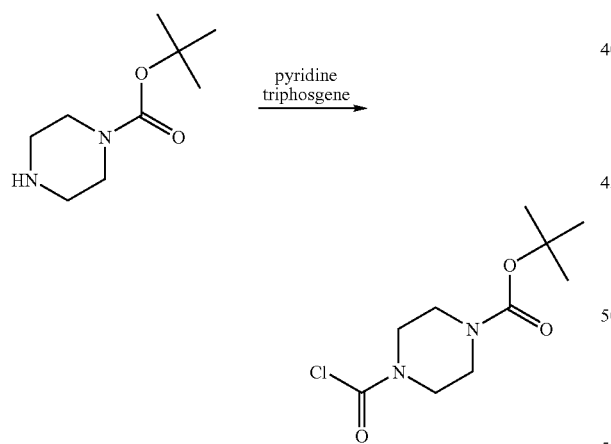

Step 3: A solution of piperazine-1-carboxylic acid tert-butyl ester (4.0 g, 22 mmol) in methylene chloride (40 mL) at 0° C. was treated with pyridine (2.65 ml, 33 mmol) and triphosgene (3.2 g, 10.8 mmol). The resulting yellow solution was stirred at 25° C. for 1 h. At this time, the reaction mixture was partitioned between methylene chloride (200 mL) and a 1N aqueous hydrochloric acid solution (75 mL). The organics were dried over magnesium sulfate and concentrated in vacuo to afford 4-chlorocarbonyl-piperazine-1-carboxylic acid tert-butyl ester (4.73 g, 89%) as a yellow solid. This material was used in the next step without further purification

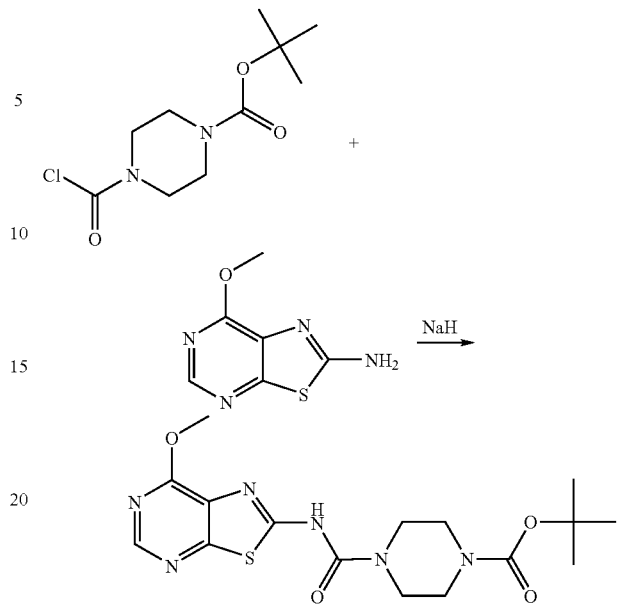

Step 4: A solution of 7-methoxy-thiazolo[5,4-d]pyrimidin-2-ylamine (3.5 g, 19.2 mmol) in tetrahydrofuran (100 mL) was treated with sodium hydride (60% in mineral oil, 2.3 g, 57 mmol) at 25° C. A slight evolution of gas was observed. The resulting purple slurry was warmed to 50° C. for 1 h. At this time, the reaction was cooled to 25° C. and was treated with N,N-diisopropylethylamine (10 mL, 57 mmol). The resulting mixture was stirred at 25° C. for 30 min. The mixture was then treated with a solution of 4-chlorocarbonyl-piperazine-1-carboxylic acid tert-butyl ester (4.73 g, 19 mmol) in tetrahydrofuran (20 mL) over a 10 min period. The reaction was stirred at 50° C. overnight. At this time, the reaction was concentrated in vacuo, diluted with methanol (100 mL) and absorbed onto silica gel (6 g). The silica gel was divided into two equal lots. ISCO chromatography (330 g, Silica, gradient elution 5/95 methanol/methylene chloride) afforded 4-(7-methoxy-thiazolo[5,4-d]pyrimidin-2-ylcarbamoyl)-piperazine-1-carboxylic acid tert-butyl ester (5.58 g, 74%) as an off-white solid; LRMS for $C_{16}H_{22}N_6O_4S$ $(M+H)^+$ at m/z=395. The NMR spectrum obtained on the sample is compatible with its structure.

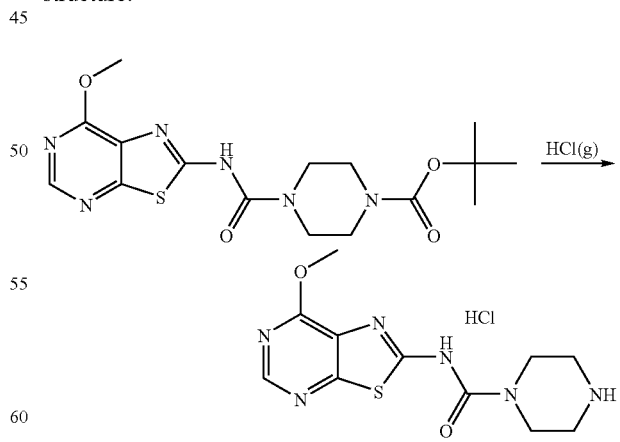

Step 5: Hydrogen chloride gas was bubbled through a solution of 4-(7-methoxy-thiazolo[5,4-d]pyrimidin-2-ylcarbamoyl)-piperazine-1-carboxylic acid tert-butyl ester (5.20 g, 13 mmol) in methylene chloride (70 mL) for 10 min at 0° C. A white precipitate formed. The resulting slurry was stirred at 25° C. for 2 h. At this time, the mixture was concentrated in vacuo and dried under high vacuum to afford piperazine-1-carboxylic acid (7-methoxy-thiazolo[5,4-d]pyrimidin-2-yl)-amide hydrochloride (4.61 g) as a white solid; LRMS for $C_{11}H_{14}N_6O_2S$ (M+H)$^+$ at m/z=295. This solid was used in the next step without further purification.

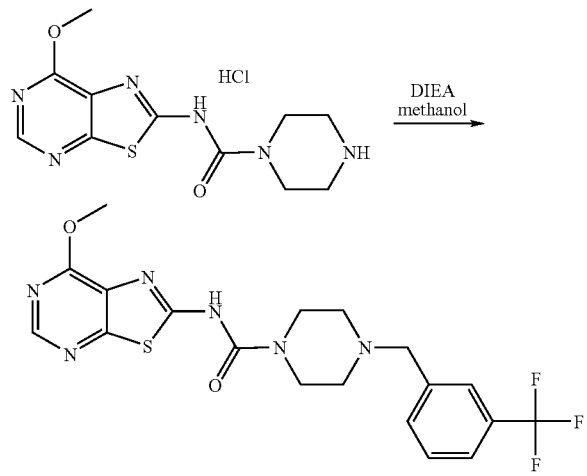

Step 6: A solution of piperazine-1-carboxylic acid (7-methoxy-thiazolo[5,4-d]pyrimidin-2-yl)-amide hydrochloride (2 g, 6.0 mmol) in methanol (200 mL) was treated with N,N-diisopropylethylamine (2.2 mL, 12.6 mmol). The mixture was stirred at 25° C. for 10 min until a clear solution formed. At this time, the reaction was treated with acetic acid (1.75 mL, 30.6 mmol), 3-trifluoromethy-benzaldehyde (2.4 mL, 17.9 mmol) and sodium cyanoborohydride (1.1 g, 17.7 mmol). This mixture was stirred at 25° C. overnight. The reaction was then concentrated in vacuo and partitioned between methylene chloride and an aqueous phosphate buffer (pH=7). The organics were washed with a saturated aqueous sodium chloride solution, dried over magnesium sulfate, filtered and concentrated in vacuo to give a solid. This solid was dissolved in methanol and absorbed onto silica gel (4 g). ISCO chromatography (330 g, Silica, gradient elution 5/95 methanol/methylene chloride) afforded 4-(3-trifluoromethyl-benzyl)-piperazine-1-carboxylic acid (7-methoxy-thiazolo[5,4-d]pyrimidin-2-yl)-amide (1.56 g, 58%) as a white solid; LRMS for $C_{19}H_{19}F_3N_6O_2S$ (M+H)$^+$ at m/z=453. The NMR spectrum obtained on the sample is compatible with its structure.

In an analogous manner, the compounds of Examples 2-28 were obtained as follows:

EXAMPLE 2

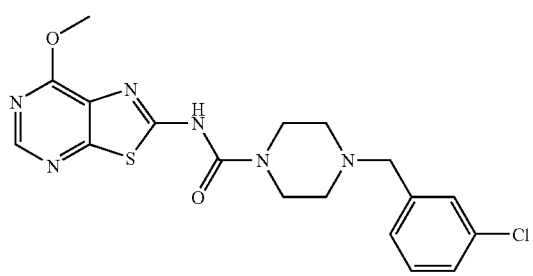

From piperazine-1-carboxylic acid (7-methoxy-thiazolo [5,4-d]pyrimidin-2-yl)-amide hydrochloride and 3-chloro-benzaldehyde: 4-(3-Chloro-benzyl)-piperazine-1-carboxylic acid (7-methoxy-thiazolo[5,4-d]pyrimidin-2-yl)-amide as a white solid; LRMS for $C_{18}H_{19}ClN_6O_2S$ (M+H)$^+$ at m/z=419. The NMR spectrum obtained on the sample is compatible with its structure.

EXAMPLE 3

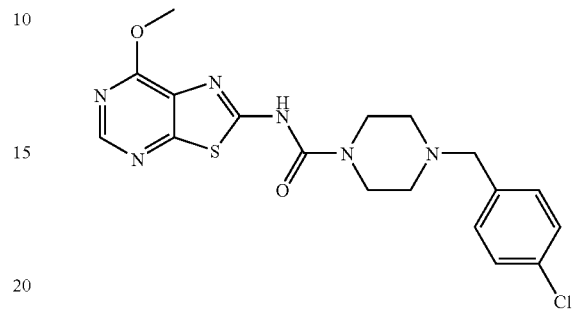

From piperazine-1-carboxylic acid (7-methoxy-thiazolo [5,4-d]pyrimidin-2-yl)-amide hydrochloride and 4-chloro-benzaldehyde: 4-(4-Chloro-benzyl)-piperazine-1-carboxylic acid (7-methoxy-thiazolo[5,4-d]pyrimidin-2-yl)-amide as a white solid; LRMS for $C_{18}H_{19}ClN_6O_2S$ (M+H)$^+$ at m/z=419. The NMR spectrum obtained on the sample is compatible with its structure.

EXAMPLE 4

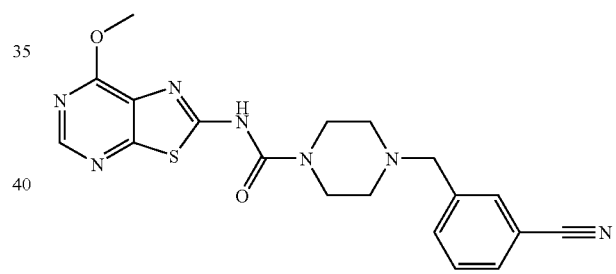

From piperazine-1-carboxylic acid (7-methoxy-thiazolo [5,4-d]pyrimidin-2-yl)-amide hydrochloride and 3-cyano-benzaldehyde: 4-(3-Cyano-benzyl)-piperazine-1-carboxylic acid (7-methoxy-thiazolo[5,4-d]pyrimidin-2-yl)-amide as a white solid; LRMS for $C_{19}H_{19}N_7O_2S$ (M+H)$^+$ at m/z=410. The NMR spectrum obtained on the sample is compatible with its structure.

EXAMPLE 5

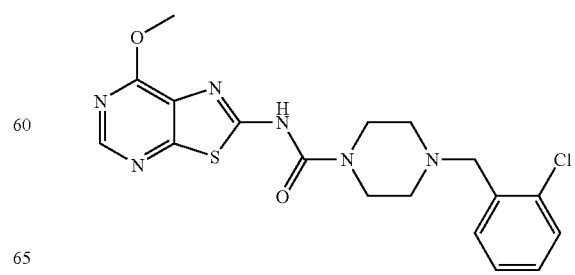

From piperazine-1-carboxylic acid (7-methoxy-thiazolo[5,4-d]pyrimidin-2-yl)-amide hydrochloride and 2-chloro-benzaldehyde: 4-(2-Chloro-benzyl)-piperazine-1-carboxylic acid (7-methoxy-thiazolo[5,4-d]pyrimidin-2-yl)-amide as a white solid; LRMS for $C_{18}H_{19}ClN_6O_2S$ (M+H)$^+$ at m/z=419. The NMR spectrum obtained on the sample is compatible with its structure.

EXAMPLE 6

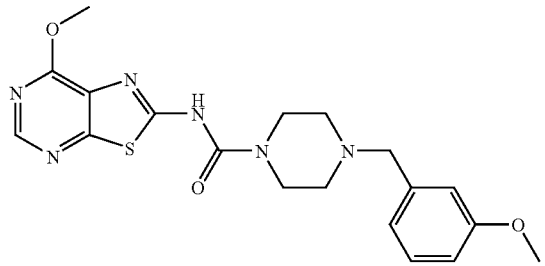

From piperazine-1-carboxylic acid (7-methoxy-thiazolo[5,4-d]pyrimidin-2-yl)-amide hydrochloride and 3-methoxy-benzaldehyde: 4-(3-Methoxy-benzyl)-piperazine-1-carboxylic acid (7-methoxy-thiazolo[5,4-d]pyrimidin-2-yl)-amide as a white solid; LRMS for $C_{19}H_{22}N_6O_3S$ (M+H)$^+$ at m/z=415. The NMR spectrum obtained on the sample is compatible with its structure.

EXAMPLE 7

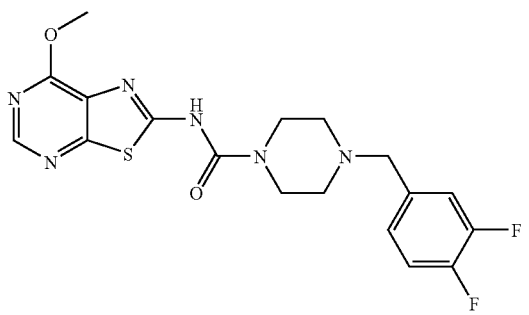

From piperazine-1-carboxylic acid (7-methoxy-thiazolo[5,4-d]pyrimidin-2-yl)-amide hydrochloride and 3,4-difluoro-benzaldehyde: 4-(3,4-Difluoro-benzyl)-piperazine-1-carboxylic acid (7-methoxy-thiazolo[5,4-d]pyrimidin-2-yl)amide as white solid; LRMS for $C_{18}H_{18}F_2N_6O_2S$ (M+H)$^+$ at m/z=421. The NMR spectrum obtained on the sample is compatible with its structure.

EXAMPLE 8

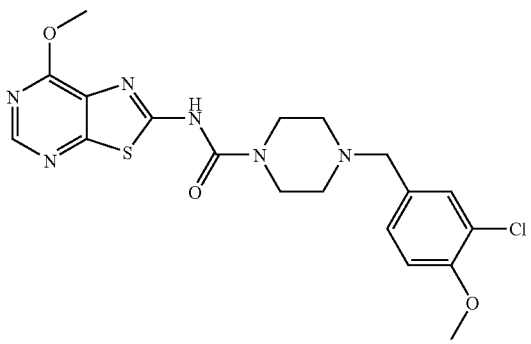

From piperazine-1-carboxylic acid (7-methoxy-thiazolo[5,4-d]pyrimdiin-2-yl)-amide hydrochloride and 3-chloro-4-methoxy-benzaldehyde: 4-(3-Chloro-4-methoxy-benzyl)-piperazine-1-carboxylic acid (7-methoxy-thiazolo[5,4-d]pyrimidin-2-yl)-amide as a white powder; LRMS for $C_{19}H_{21}ClN_6O_3S$ (M+H)$^+$ at m/z=449. The NMR spectrum obtained on the sample is compatible with its structure.

EXAMPLE 9

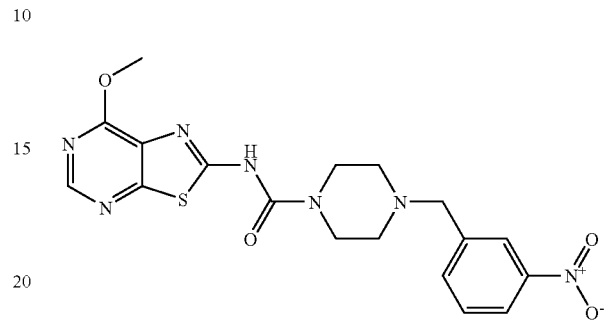

From piperazine-1-carboxylic acid (7-methoxy-thiazolo[5,4-d]pyrimidin-2-yl)-amide hydrochloride and 3-nitro-benzaldehyde: 4-(3-Nitro-benzyl)-piperazine-1-carboxylic acid (7-methoxy-thiazolo[5,4-d]pyrimidin-2-yl)-amide as a white powder; LRMS for $C_{18}H_{19}N_7O_4S$ (M+H)$^+$ at m/z=430. The NMR spectrum obtained on the sample is compatible with its structure.

EXAMPLE 10

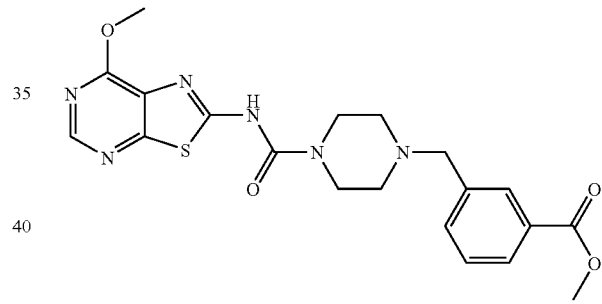

From piperazine-1-carboxylic acid (7-methoxy-thiazolo[5,4-d]pyrimidin-2-yl)-amide hydrochloride and 3-formyl-benzoic acid methyl ester: 3-[4-(7-Methoxy-thiazolo[5,4-d]pyrimidin-2-ylcarbamoyl)-piperazin-1-ylmethyl]-benzoic acid methyl ester as a white solid; LRMS for $C_{20}H_{22}N_6O_4S$ (M+H)$^+$ at m/z=443. The NMR spectrum obtained on the sample is compatible with its structure.

EXAMPLE 11

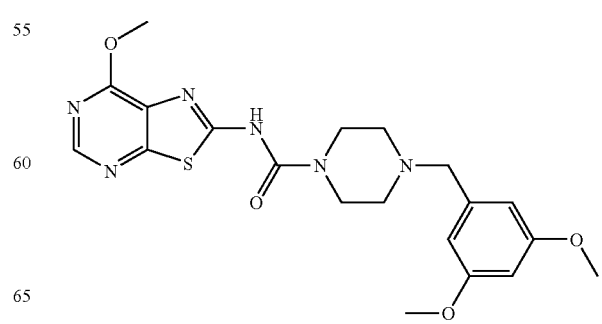

From piperazine-1-carboxylic acid (7-methoxy-thiazolo[5,4-d]pyrimidin-2-yl)-amide hydrochloride and 3,5-dimethoxy-benzaldehyde: 4-(3,5-Dimethoxy-benzyl)piperazine-1-carboxylic acid (7-methoxy-thiazolo[5,4-d]pyrimidin-2-yl)-amide as a white solid; LRMS for $C_{20}H_{24}N_6O_4S$ (M+H)$^+$ at m/z=445. The NMR spectrum obtained on the sample is compatible with its structure.

EXAMPLE 12

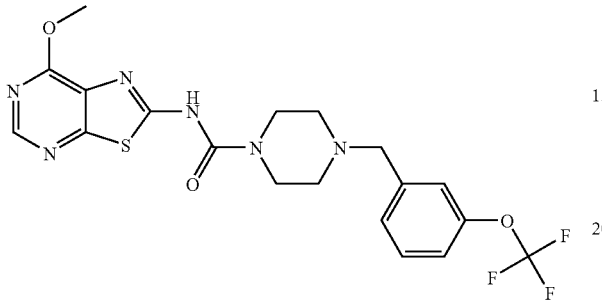

From piperazine-1-carboxylic acid (7-methoxy-thiazolo[5,4-d]pyrimidin-2-yl)-amide hydrochloride and 3-trifluoromethoxy-benzaldehyde: 4-(3-Trifluoromethoxy-benzyl)-piperazine-1-carboxylic acid (7-methoxy-thiazolo[5,4-d]pyrimidin-2-yl)-amide as a white solid; LRMS for $C_{19}H_{19}F_3N_6O_3S$ (M+H)$^+$ at m/z=469. The NMR spectrum obtained on the sample is compatible with its structure.

EXAMPLE 13

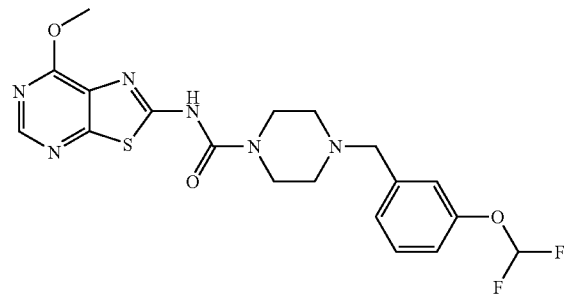

From piperazine-1-carboxylic acid (7-methoxy-thiazolo[5,4-d]pyrimidin-2-yl)-amide hydrochloride and 3-difluoromethoxy-benzaldehyde: 4-(3-Difluoromethoxy-benzyl)-piperazine-1-carboxylic acid (7-methoxy-thiazolo[5,4-d]pyrimidin-2-yl)-amide as a white solid; LRMS for $C_{19}H_{20}F_2N_6O_3S$ (M+H)$^+$ at m/z=451. The NMR spectrum obtained on the sample is compatible with its structure.

EXAMPLE 14

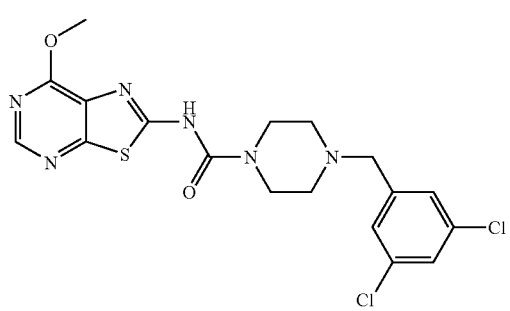

From piperazine-1-carboxylic acid (7-methoxy-thiazolo[5,4-d]pyrimidin-2-yl)-amide hydrochloride and 3,5-dichloro-benzaldehyde: 4-(3,5-Dichloro-benzyl)-piperazine-1-carboxylic acid (7-methoxy-thiazolo[5,4-d]pyrimidin-2-yl)-amide as a white solid; LRMS for $C_{18}H_{18}Cl_2N_6O_2S$ (M+H)$^+$ at m/z=454. The NMR spectrum obtained on the sample is compatible with its structure.

EXAMPLE 15

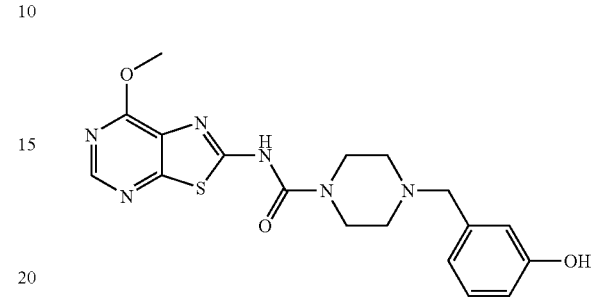

From piperazine-1-carboxylic acid (7-methoxy-thiazolo[5,4-d]pyrimidin-2-yl)-amide hydrochloride and 3-hydroxy-benzaldehyde: 4-(3-Hydroxy-benzyl)-piperazine-1-carboxylic acid (7-methoxy-thiazolo[5,4-d]pyrimidin-2-yl)-amide as an off-white solid; LRMS for $C_{18}H_{20}N_6O_3S$ (M+H)$^+$ at m/z=401. The NMR spectrum obtained on the sample is compatible with its structure.

EXAMPLE 16

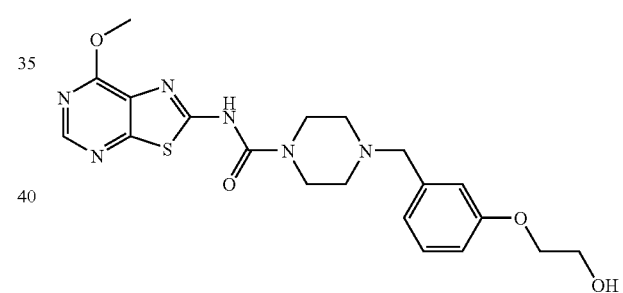

From piperazine-1-carboxylic acid (7-methoxy-thiazolo[5,4-d]pyrimidin-2-yl)-amide hydrochloride and 3-(2-hydroxy-ethoxy)-benzaldehyde: 4-[3-(2-Hydroxy-ethoxy)-benzyl]-piperazine-1-carboxylic acid (7-methoxy-thiazolo[5,4-d]pyrimidin-2-yl)-amide as a off-white solid; LRMS for $C_{20}H_{24}N_6O_4S$ (M+H)$^+$ at m/z=445. The NMR spectrum obtained on the sample is compatible with its structure.

EXAMPLE 17

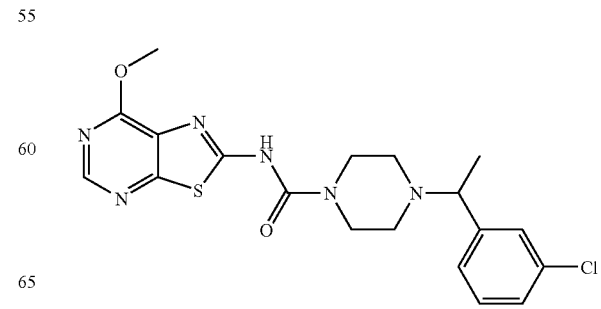

From piperazine-1-carboxylic acid (7-methoxy-thiazolo[5,4-d]pyrimidin-2-yl)-amide hydrochloride and 1-(3-chloro-phenyl)-ethanone: 4-[1-(3-Chloro-phenyl)-ethyl]-piperazine-1-carboxylic acid (7-methoxy-thiazolo[5,4-d]pyrimidin-2-yl)-amide as an off-white solid; LRMS for $C_{19}H_{21}ClN_6O_2S$ (M+H)$^+$ at m/z=433. The NMR spectrum obtained on the sample is compatible with its structure.

EXAMPLE 18

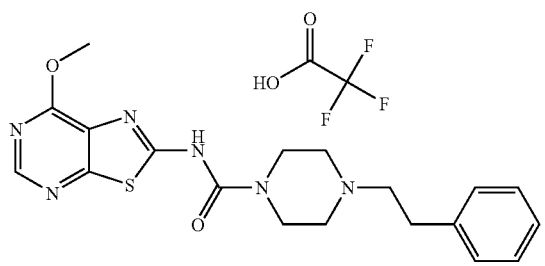

From piperazine-1-carboxylic acid (7-methoxy-thiazolo[5,4-d]pyrimidin-2-yl)-amide hydrochloride and phenyl-acetaldehyde: 4-Phenethyl-piperazine-1-carboxylic acid (7-methoxy-thiazolo[5,4-d]pyrimidin-2-yl)-amide trifluoroacetate as an off-white solid; LRMS for $C_{19}H_{22}N_6O_2S$ (M+H)$^+$ at m/z=399.

EXAMPLE 19

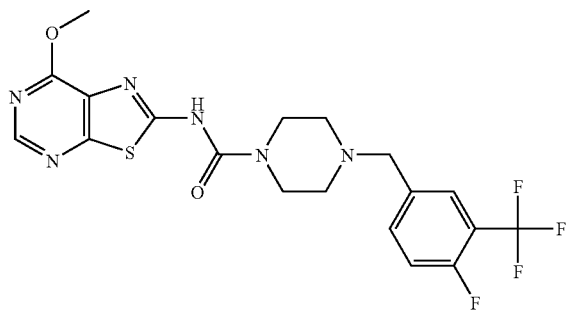

From piperazine-1-carboxylic acid (7-methoxy-thiazolo[5,4-d]pyrimidin-2-yl)-amide hydrochloride and 4-fluoro-3-(trifluoromethyl) benzaldehyde: 4-(4-Fluoro-3-trifluoromethyl-benzyl)-piperazine-1-carboxylic acid (7-methoxy-thiazolo[5,4-d]pyrimidin-2-yl)-amide as a white solid; ES-HRMS m/e calcd for $C_{19}H_{18}F_4N_6O_2S$ (M+H)$^+$ 471.1221, found 471.1220.

EXAMPLE 20

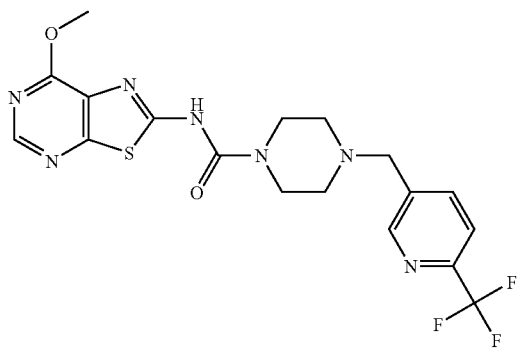

From piperazine-1-carboxylic acid (7-methoxy-thiazolo[5,4-d]pyrimidin-2-yl)-amide hydrochloride and 6-trifluoromethyl-pyridine-3-carbaldehyde: 4-(6-Trifluoromethyl-pyridin-3-ylmethyl)-piperazine-1-carboxylic acid (7-methoxy-thiazolo[5,4-d]pyrimidin-2-yl)-amide as a white solid; ES-HRMS m/e calcd for $C_{18}H_{18}F_3N_7O_2S$ (M+H)$^+$ 454.1268, found 454.1272.

EXAMPLE 21

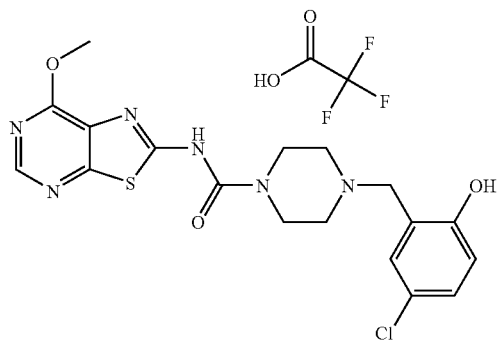

From piperazine-1-carboxylic acid (7-methoxy-thiazolo[5,4-d]pyrimidin-2-yl)-amide hydrochloride and 5-chloro-salicaldehyde: 4-(5-Chloro-2-hydroxy-benzyl)-piperazine-1-carboxylic acid (7-methoxy-thiazolo[5,4-d]pyrimidin-2-yl)-amide trifluoroacetate salt as a white solid; ES-HRMS m/e calcd. for $C_{18}H_{20}N_6O_3SCl$ (M+H)$^+$ 435.1001, found 435.1002.

EXAMPLE 22

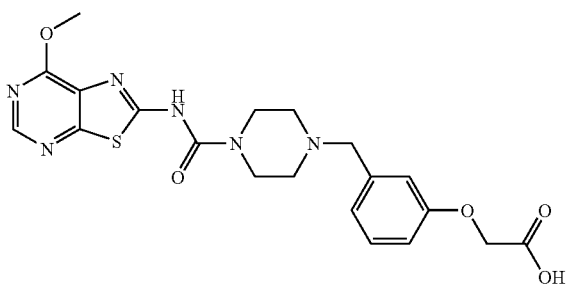

From piperazine-1-carboxylic acid (7-methoxy-thiazolo[5,4-d]pyrimidin-2-yl)-amide hydrochloride and 3-formylphenoxyacetic acid: {3-[4-(7-Methoxy-thiazolo[5,4-d]pyrimidin-2-ylcarbamoyl)-piperazin-1-ylmethyl]-phenoxy}-acetic acid trifluoroacetate salt as a white solid; ES-HRMS m/e calcd. for $C_{20}H_{23}N_6O_5S$ (M+H)$^+$ 459.1445, found 459.1446.

EXAMPLE 23

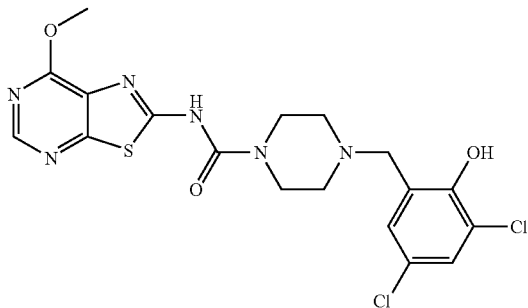

From piperazine-1-carboxylic acid (7-methoxy-thiazolo[5,4-d]pyrimidin-2-yl)-amide hydrochloride and 3,5-dichlorosalicylaldehyde: 4-(3,5-Dichloro-2-hydroxy-benzyl)-piperazine-1-carboxylic acid (7-methoxythiazolo[5,4-d]pyrimidin-2-yl)-amide trifluoroacetate salt as a white solid; ES-HRMS m/e calcd. for $C_{18}H_{19}N_6O_3SCl_2$ $(M+H)^+$ 469.0611, found 469.0613.

EXAMPLE 24

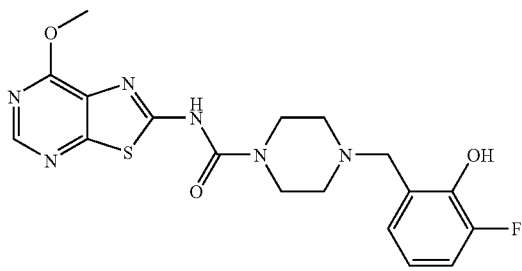

From piperazine-1-carboxylic acid (7-methoxy-thiazolo[5,4-d]pyrimidin-2-yl)-amide hydrochloride and 3-fluoro-salicylaldehyde: 4-(3-Fluoro-2-hydroxy-benzyl)-piperazine-1-carboxylic acid (7-methoxy-thiazolo[5,4-d]pyrimidin-2-yl)-amide trifluoroacetate salt as a white solid; ES-HRMS m/e calcd. for $C_{18}H_{20}N_6O_3SF$ $(M+H)^+$ 419.1296, found 419.1298.

EXAMPLE 25

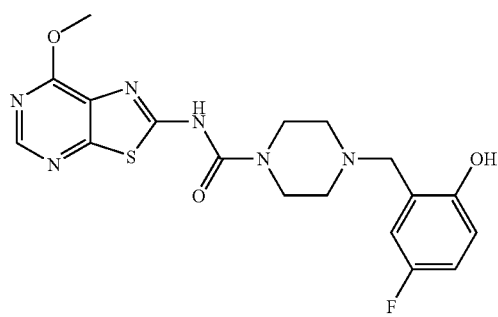

From piperazine-1-carboxylic acid (7-methoxy-thiazolo[5,4-d]pyrimidin-2-yl)-amide hydrochloride and 5-fluoro-salicylaldehyde: 4-(5-Fluoro-2-hydroxy-benzyl)-piperazine-1-carboxylic acid (7-methoxy-thiazolo[5,4-d]pyrimidin-2-yl)-amide trifluoroacetate salt as a white solid; ES-HRMS m/e calcd. for $C_{18}H_{20}N_6O_3SF$ $(M+H)^+$ 419.1296, found 419.1298.

EXAMPLE 26

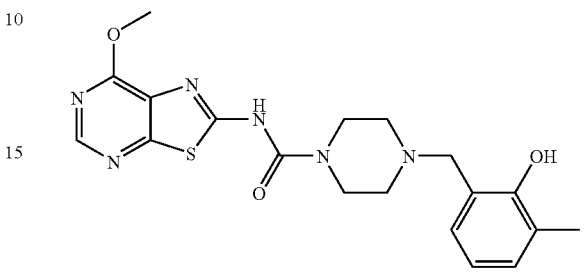

From piperazine-1-carboxylic acid (7-methoxy-thiazolo[5,4-d]pyrimidin-2-yl)-amide hydrochloride and 3-methyl-salicylaldehyde: 4-(2-Hydroxy-3-methyl-benzyl)-piperazine-1-carboxylic acid (7-methoxy-thiazolo[5,4-d]pyrimidin-2-yl)-amide trifluoroacetate salt as a white solid; ES-HRMS m/e calcd. for $C_{19}H_{23}N_6O_3S$ $(M+H)^+$ 415.1547, found 415.1547.

EXAMPLE 27

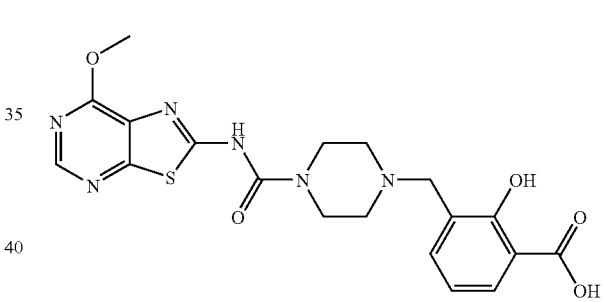

From piperazine-1-carboxylic acid (7-methoxy-thiazolo[5,4-d]pyrimidin-2-yl)-amide hydrochloride and 3-formyl-salicylic acid: 2-Hydroxy-3-[4-(7-methoxy-thiazolo[5,4-d]pyrimidin-2-ylcarbamoyl)-piperazin-1-ylmethyl]-benzoic acid trifluoroacetate salt as a white solid; ES-HRMS m/e calcd. for $C_{19}H_{21}N_6O_5S$ $(M+H)^+$ 445.1289, found 445.1291.

EXAMPLE 28

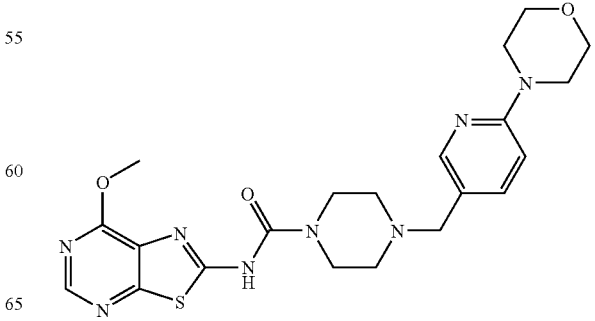

From piperazine-1-carboxylic acid (7-methoxy-thiazolo[5,4-d]pyrimidin-2-yl)-amide hydrochloride and 6-morpholino-nicotinaldehyde: 4-(6-Morpholin-4-yl-pyridin-3-yl methyl)-piperazine-1-carboxylic acid (7-methoxy-thiazolo[5,4-d]pyrimidin-2-yl)-amide as a white solid; LRMS for $C_{21}H_{26}N_6O_3S$ (M+H)$^+$ at m/z=470. The NMR spectrum obtained on the sample is compatible with its structure.

EXAMPLE 29

Synthesis of 4-pyridin-2-ylmethyl-piperazine-1-carboxylic acid (7-methoxy-thiazolo[5,4-d]pyrimidin-2-yl)-amide

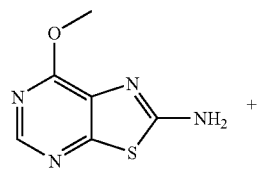

+

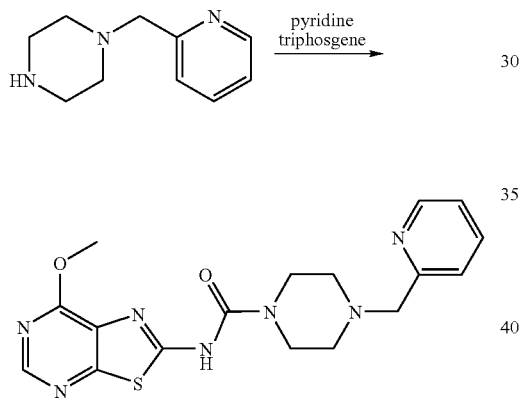

A mixture of triphosgene (165 mg, 0.55 mmol) in tetrahydrofuran (10 mL) was slowly treated with pyridine (260 mg, 3.30 mmol) followed by the portionwise addition of 7-methoxy-thiazole[5,4-d]pyrimidin-2-ylamine (200 mg, 1.10 mmol). The mixture was allowed to stir at 25° C. for 2 h. At this time, the reaction was treated with 1-[(2-pyridyl)methyl]piperazine (390 mg, 2.20 mmol). The mixture continued to stir at 25° C. for an additional 2 h. At this time, the reaction was quenched by the slow addition of water. The aqueous layer was extracted with ethyl acetate. The organics were then washed with a saturated aqueous sodium chloride solution, dried over magnesium sulfate, filtered, and concentrated in vacuo. Flash chromatography (Merck Silica gel 60, 230-400 mesh, 98/2 methylene chloride/ methanol) afforded 4-pyridin-2-ylmethyl-piperazine-1-carboxylic acid (7-methoxy-thiazolo[5,4-d]pyrimidin-2-yl)-amide (43 mg, 10%) as a light yellow oil; LRMS for $C_{17}H_{19}N_7O_2S$ (M+H)$^+$ at m/z=385. The NMR spectrum obtained on the sample is compatible with its structure.

In an analogous manner, the compounds of Examples 30-36 were obtained as follows:

EXAMPLE 30

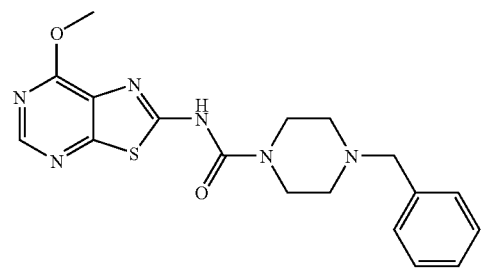

From (7-methoxy-thiazolo[5,4-d]pyrimidin-2-yl)-methylamine and 1-benzylpiperazine: 4-Benzyl-piperazine-1-carboxylic acid (7-methoxy-thiazolo[5,4-d]pyrimidin-2-yl)-amide as a yellow solid; ES-HRMS m/e calcd. for $C_{18}H_{21}N_6O_2S$ (M+H)$^+$ 385.1441, found 385.1441.

Example 31

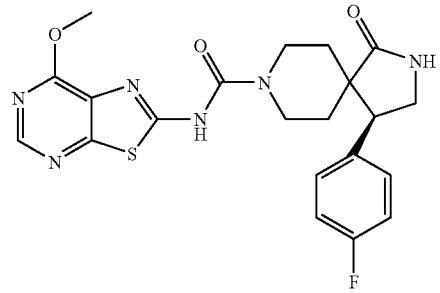

From (7-methoxy-thiazolo[5,4-d]pyrimidin-2-yl)-methylamine and 4-(4-Fluoro-phenyl)-2,8-diaza-spiro[4.5]decan-1-one: 4-(4-Fluoro-phenyl)-1-oxo-2,8-diazaspiro[4,5]decane-8-carboxylic acid(7-methoxy-thiazolo[5,4-d]pyrimidin-2-yl)-amide (59 mg, 24%) was obtained as a white solid; LRMS for $C_{21}H_{21}FN_6O_3S$ (M+H)$^+$ at m/z=456. The NMR spectrum obtained on the sample is compatible with its structure.

EXAMPLE 32

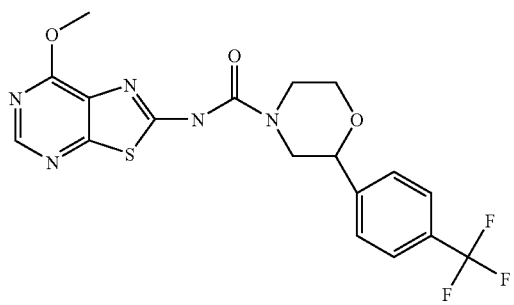

From 7-methoxy-thiazolo[5,4-d]pyrimidin-2-ylamine and 2-(4-trifluoromethyl-phenyl)-morpholine: 2-(4-Trifluoromethyl-phenyl)-morpholine-4-carboxylic acid (7-methoxy-thiazolo[5,4-d]pyrimidin-2-yl)-amide (140 mg, 58%) was obtained as a white solid; LRMS for $C_{18}H_{16}F_3N_5O_3S$ (M+H)$^+$ at m/z=439. The NMR spectrum obtained on the sample is compatible with its structure.

EXAMPLE 33

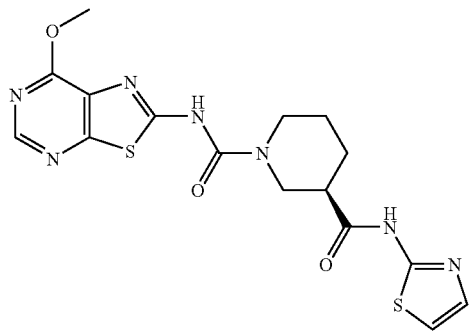

From 7-methoxy-thiazolo[5,4-d]pyrimidin-2-ylamine and piperidine-3-carboxylic acid thiazol-2-ylamide hydrochloride: Piperidine-1,3-dicarboxylic acid 1-[(7-methoxy-thiazolo[5,4-d]pyrimidin-2-yl)-amide]3-thiazol-2-ylamide (11 mg, 5.4%) as white solid; ES-HRMS m/e calcd for $C_{16}H_{17}N_7O_3S_2$ (M+Na)$^+$ 442.0726, found 442.0729.

EXAMPLE 34

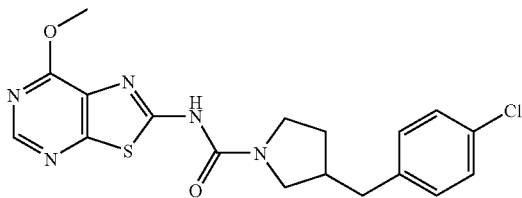

From 7-methoxy-thiazolo[5,4-d]pyrimidin-2-ylamine and 3-(4-chlorobenzyl)pyrrolidine oxalate: 3-(4-Chloro-benzyl)-pyrrolidine-1-carboxylic acid (7-methoxy-thiazolo[5,4-d]pyrimidin-2-yl)-amide (21 mg, 9.3%) as white solid; ES-HRMS m/e calcd for $C_{18}H_{18}ClN_5O_2S$ (M+H)$^+$ 404.0943, found 404.0944.

EXAMPLE 35

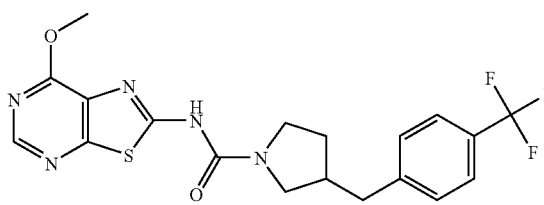

From 7-methoxy-thiazolo[5,4-d]pyrimidin-2-ylamine and 3-[4-(trifluoromethyl)benzyl]pyrrolidine oxalate: 3-(4-Trifluoromethyl-benzyl)-pyrrolidine-1-carboxylic acid (7-methoxy-thiazolo[5,4-d]pyrimidin-2-yl)-amide (12 mg, 5%) as white solid;. ES-HRMS m/e calcd for $C_{19}H_{18}F_3N_5O_2S$ (M+H)$^+$ 438.1206, found 438.1207.

EXAMPLE 36

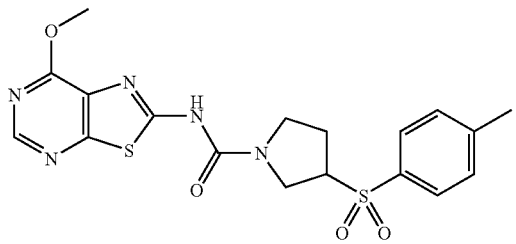

From 7-methoxy-thiazolo[5,4-d]pyrimidin-2-ylamine and 3-(4-methylphenylsulfonyl)pyrrolidine hydrochloride: 3-(Toluene-4-sulfonyl)-pyrrolidine-1-carboxylic acid (7-methoxy-thiazolo[5,4-d]pyrimidin-2-yl)-amide (78 mg, 32.8%) as white solid; ES-HRMS m/e calcd for $C_{18}H_{19}N_5O_4S_2$ (M+H)$^+$ 434.0951, found 434.0951.

EXAMPLE 37

Synthesis of 4-(4-Chloro-2-methanesulfonyl-benzyl)-piperazine-1-carboxylic acid (7-methoxy-thiazolo[5,4-d]pyrimidin-2-yl)-amide

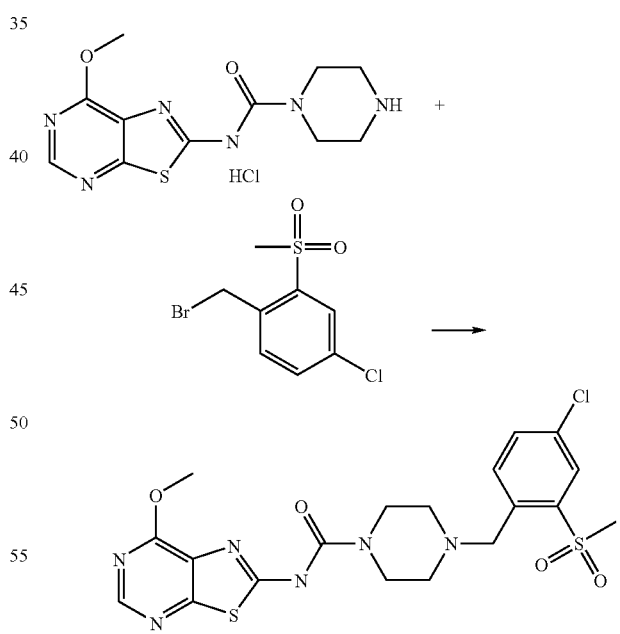

A mixture of piperazine-1-carboxylic acid (7-methoxy-thiazolo[5,4-d]pyrimidin-2-yl)-amide hydrochloride (as prepared in Example 1, 625 mg, 1.70 mmol) in N,N-dimethylformamide (5 mL) was treated with N,N-diisopropylethylamine (660 mg, 5.10 mmol) followed by 1-(bromomethyl)-4-chloro-2-(methylsulfonyl)-benzene (530 mg, 1.87 mmol). The reaction mixture was allowed to stir at 80° C. for 3 h. At this time, the reaction was poured into water. The aqueous layer was extracted with ethyl acetate. The organics were washed with a saturated aqueous sodium chloride solution, dried over magnesium sulfate, filtered, and concentrated in vacuo. Flash chromatography (Merck Silica gel 60, 230-400 mesh, 80/20 hexanes/ethyl acetate) afforded 4-(4-chloro-2-methanesulfonyl-benzyl)-piperazine-1-carboxylic acid (7-methoxy-thiazolo[5,4-d]pyrimidin-2-yl)-amide (580 mg, 69%) as an off-white solid; LRMS for $C_{19}H_{21}ClN_6O_4S_2$ (M+H)$^+$ at m/z=496. The NMR spectrum obtained on the sample is compatible with its structure.

In an analogous manner, the compounds of Examples 38-42 were obtained as follows:

EXAMPLE 38

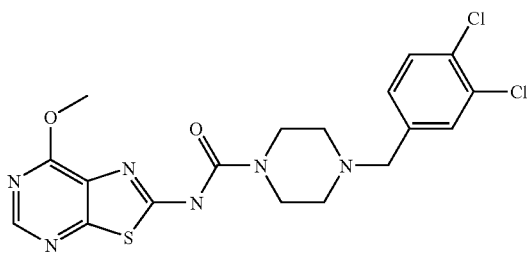

From piperazine-1-carboxylic acid (7-methoxy-thiazolo[5,4-d]pyrimidin-2-yl)-amide hydrochloride and 3,4-dichlorobenzyl bromide: 4-(3,4-Dichloro-benzyl)-piperazine-1-carboxylic acid (7-methoxy-thiazolo[5,4-d]pyrimidin-2-yl)-amide (64 mg, 26%) was obtained as a white solid; LRMS for $C_{18}H_{18}Cl_2N_6O_2S$ (M+H)$^+$ at m/z=453. The NMR spectrum obtained on the sample is compatible with its structure.

EXAMPLE 39

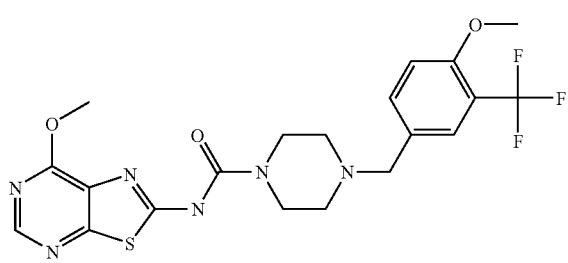

From piperazine-1-carboxylic acid (7-methoxy-thiazolo[5,4-d]pyrimidin-2-yl)-amide hydrochloride and 4-methoxy-3-(trifluoromethyl)benzyl bromide: 4-(4-Methoxy-3-trifluoromethyl-benzyl)-piperazine-1-carboxylic acid (7-methoxy-thiazolo[5,4-d]pyrimidin-2-yl)-amide (90 mg, 34%) was obtained as a light brown solid; LRMS for $C_{20}H_{21}F_3N_6O_3S$ (M+H)$^+$ at m/z=482. The NMR spectrum obtained on the sample is compatible with its structure.

EXAMPLE 40

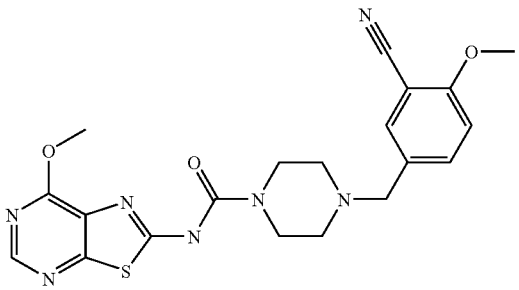

From piperazine-1-carboxylic acid (7-methoxy-thiazolo[5,4-d]pyrimidin-2-yl)-amide hydrochloride and 5-bromomethyl-2-methoxy-benzonitrile: 4-(3-Cyano-4-methoxy-benzyl)-piperazine-1-carboxylic acid (7-methoxy-thiazolo[5,4-d]pyrimidin-2-yl)-amide (25 mg, 6%) was obtained as a light brown solid; LRMS for $C_{20}H_{21}N_7O_3S$ (M+H)$^+$ at m/z=439. The NMR spectrum obtained on the sample is compatible with its structure.

EXAMPLE 41

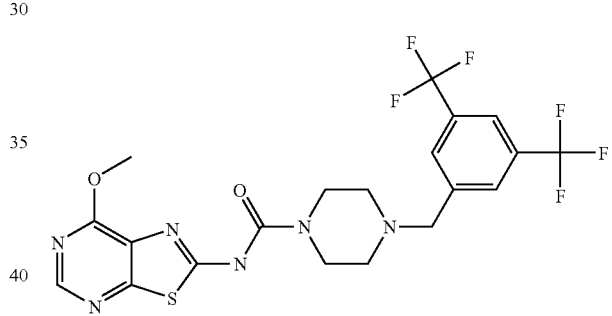

From piperazine-1-carboxylic acid (7-methoxy-thiazolo[5,4-d]pyrimidin-2-yl)-amide hydrochloride and 3,5-bis(trifluoromethyl)benzyl bromide: 4-(3,5-Bis-trifluoromethyl-benzyl)-piperazine-1-carboxylic acid (7-methoxy-thiazolo[5,4-d]pyrimidin-2-yl)-amide (130 mg, 28%) was obtained as an off-white solid; LRMS for $C_{20}H_{18}F_6N_6O_2S$ (M+H)$^+$ at m/z=520. The NMR spectrum obtained on the sample is compatible with its structure.

EXAMPLE 42

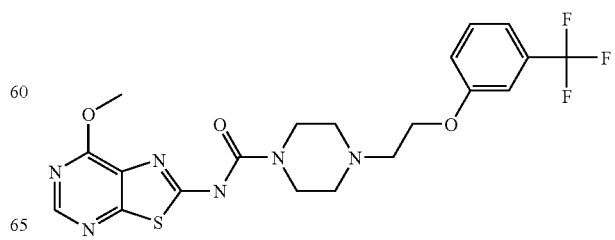

(e) From piperazine-1-carboxylic acid (7-methoxy-thiazolo[5,4-d]pyrimidin-2-yl)-amide hydrochloride and 1-(2-bromoethoxy)-3-(trifluoromethyl) benzene: 4-[2-(3-Trifluoromethyl-phenoxy)-ethyl]-piperazine-1-carboxylic acid (7-methoxy-thiazolo[5,4-d]pyrimidin-2-yl)-amide (39 mg, 9%) was obtained as a brown solid; LRMS for $C_{20}H_{21}F_3N_6O_3S$ (M+H)$^+$ at m/z=482. The NMR spectrum obtained on the sample is compatible with its structure.

EXAMPLE 43

Synthesis of 4-(4-Fluoro-3-trifluoromethyl-benzoyl) piperazine-1-carboxylic acid (7-methoxy-thiazolo[5,4-d]pyrimidin-2-yl)-amide

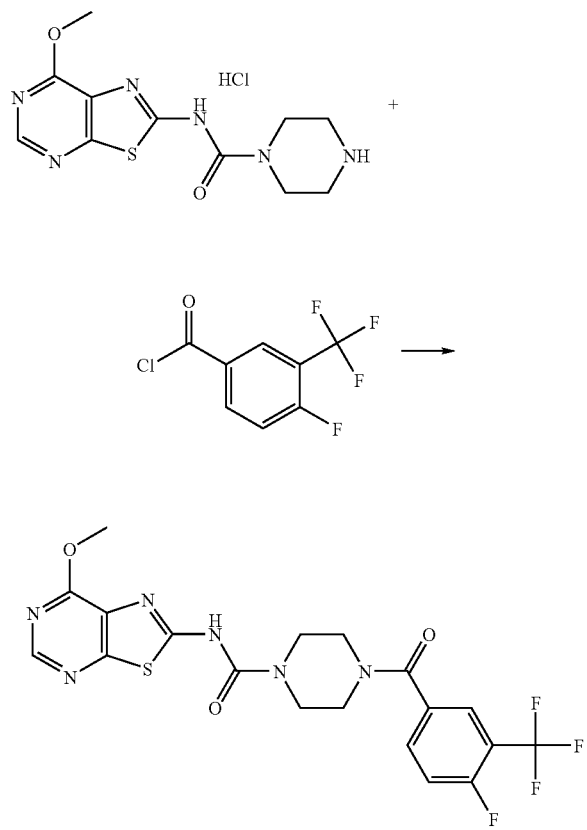

A solution of piperazine-1-carboxylic acid (7-methoxy-thiazolo[5,4-d]pyrimidin-2-yl)-amide hydrochloride (as prepared in Example 1, 300 mg, 0.91 mmol), 4-fluoro-3-(trifluoromethyl)benzyl chloride (140 mL, 0.92 mmol) and triethylamine (3.4 mL, 2.27 mmol) in methylene chloride (15 mL) was stirred overnight at 25° C. At this time, the reaction was poured into water and was extracted into ethyl acetate. The combined organics were washed with a saturated aqueous sodium bicarbonate solution, dried over sodium sulfate, filtered and concentrated in vacuo. The resulting solids were recrystallized twice from 2:1:1 methanol/dimethylsulfoxide/dioxane to afford 4-(4-fluoro-3-trifluoromethyl-benzoyl)-piperazine-1-carboxylic acid (7-methoxy-thiazolo[5,4-d]pyrimidin-2-yl)-amide (134 mg, 30.5%) as white solid; ES-HRMS m/e calcd for $C_{19}H_{16}F_4N_6O_3S$ (M+H)$^+$ 485.1014, found 485.1014.

In an analogous manner, the compounds of Examples 44-46 were obtained as follows:

EXAMPLE 44

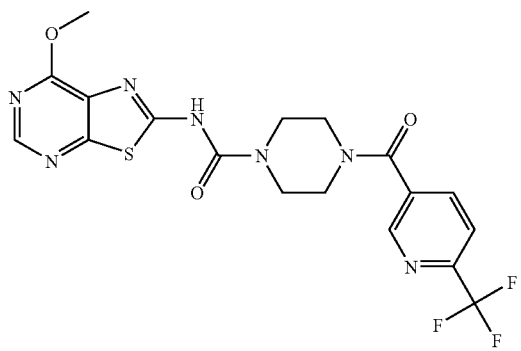

From piperazine-1-carboxylic acid (7-methoxy-thiazolo[5,4-d]pyrimidin-2-yl)-amide hydrochloride and 6-trifluoromethyl-nicotinoyl chloride: 4-(6-Trifluoromethyl-pyridine-3-carbonyl)-piperazine-1-carboxylic acid (7-methoxy-thiazolo[5,4-d]pyrimidin-2-yl)-amide as a white solid; ES-HRMS m/e calcd for $C_{18}H_{16}F_3N_7O_3S$ (M+H)$^+$ 468.1060, found 468.1058.

EXAMPLE 45

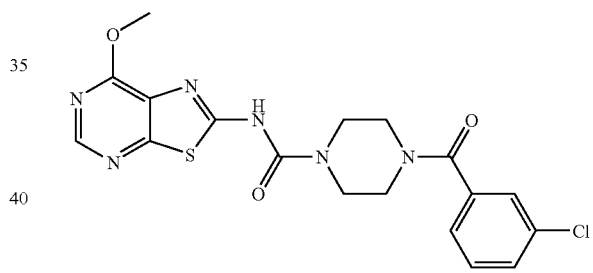

From piperazine-1-carboxylic acid (7-methoxy-thiazolo[5,4-d]pyrimidin-2-yl)-amide hydrochloride and 3-chlorobenzoyl chloride: 4-(3-Chloro-benzoyl)-piperazine-1-carboxylic acid (7-methoxy-thiazolo[5,4-d]pyrimidin-2-yl)-amide as a white solid; LRMS for $C_{18}H_{17}ClN_6O_3S$ (M+H)$^+$ at m/z=433. The NMR spectrum obtained on the sample is compatible with its structure.

EXAMPLE 46

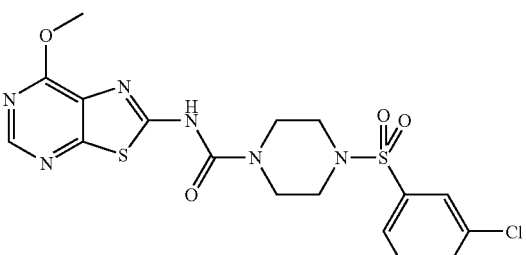

From piperazine-1-carboxylic acid (7-methoxy-thiazolo[5,4-d]pyrimidin-2-yl)-amide hydrochloride and 3-chloro-benzenesulfonyl chloride: 4-(3-Chloro-benzenesulfonyl)-piperazine-1-carboxylic acid (7-methoxy-thiazolo[5,4-d]pyrimidin-2-yl)-amide as an off-white solid; LRMS for $C_{17}H_{17}ClN_6O_4S_2$ (M+H)$^+$ at m/z=469. The NMR spectrum obtained on the sample is compatible with its structure

EXAMPLE 47

Synthesis of 4-[3-(trifluoromethy)phenyl]piperazine-1-carboxylic acid (7-methoxy-thiazolo[5,4-d]pyrimidin-2-yl)-amide

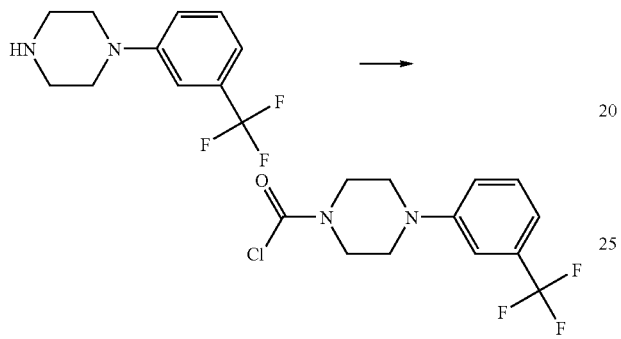

Step 1: A mixture of triphosgene (3.2 g, 10.85 mmol) in tetrahydrofuran (10 mL) was slowly treated with pyridine (1.72 g, 21.72 mmol) via syringe. The resulting white suspension was then treated portionwise with 1-[3-(trifluoromethyl)phenyl]piperazine (500 mg, 2.17 mmol). The reaction mixture was allowed to stir at 25° C. for 18 h. At this time, the reaction was slowly quenched by the addition of water. The aqueous layer was extracted with methylene chloride. The organics were washed with a saturated aqueous sodium chloride solution, dried over magnesium sulfate, filtered and concentrated in vacuo to afford 4-(3-trifluoromethyl-phenyl)piperazine-1-carbonyl chloride (500 mg, 79%). The NMR spectrum obtained on the sample is compatible with its structure.

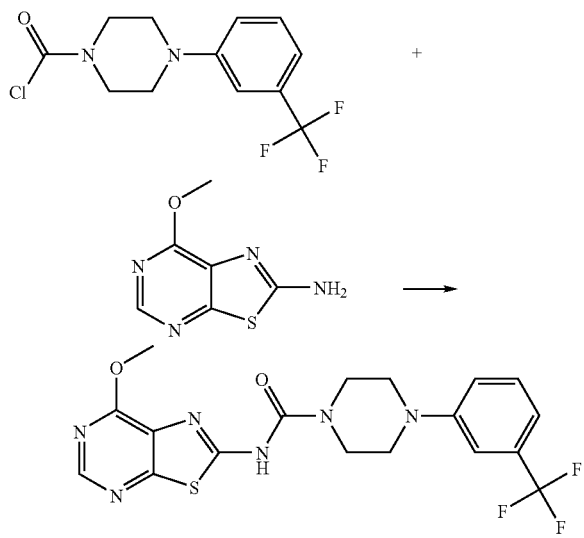

Step 2: A mixture of 7-methoxy-thiazole[5,4-d]pyrimidin-2-ylamine (100 mg, 0.55 mmol) in tetrahydrofuran (10 mL) under a nitrogen atmosphere at 25° C. was treated with sodium hydride (60% suspension in mineral oil, 30 mg, 0.66 mmol). The reaction mixture was stirred at 50° C. for 30 min. At this time, the reaction was treated with N,N-diisopropyl-ethylamine (215 mg, 1.65 mmol) and 4-[3-(trifluoromethyl)phenyl]piperazine-1-carbonyl chloride (180 mg, 0.60 mmol). This mixture was stirred at 50° C. for 3 d. At this time, the reaction was concentrated in vacuo, poured into water and extracted with ethyl acetate. The organics were washed with a 2N aqueous hydrochloric acid solution and a saturated aqueous sodium chloride solution, dried over magnesium sulfate, filtered and concentrated in vacuo. Flash chromatography (Merck Silica gel 60, 230-400 mesh, 80/20 hexanes/ethyl acetate) afforded 4-[3-(trifluoromethy)phenyl]piperazine-1-carboxylic acid (7-methoxy-thiazolo[5,4-d]pyrimidin-2-yl)-amide (70 mg, 29%) as a light brown solid; LRMS for $C_{18}H_{17}F_3N_6O_2S$ (M+H)$^+$ at m/z=438. The NMR spectrum obtained on the sample is compatible with its structure.

In an analogous manner, the compounds of Examples 48-58 were obtained as follows:

EXAMPLE 48

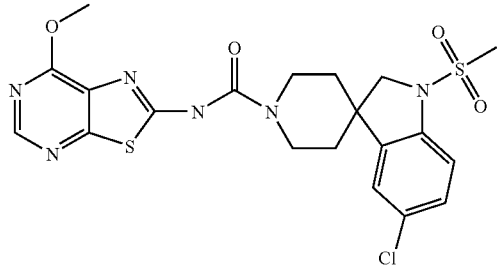

From 7-methoxy-thiazole[5,4-d]pyrimidin-2-ylamine and 5-Chloro-1,2-dihydro-1-(methylsulfonyl)spiro[3H-indole-3,4'-piperidine] hydrochloride: 5-Chloro-1,2-dihydro-N-(7-methoxythiazole[5,4-d]pyrimidin-2-yl)-1-(methylsulfonyl)spiro[3H-indole-3,4'-piperidine]-1'-carboxamide (214 mg, 77%) was obtained as a light brown solid; LRMS for $C_{20}H_{21}ClN_6O_4S_2$ (M+H)$^+$ at m/z=508. The NMR spectrum obtained on the sample is compatible with its structure.

EXAMPLE 49

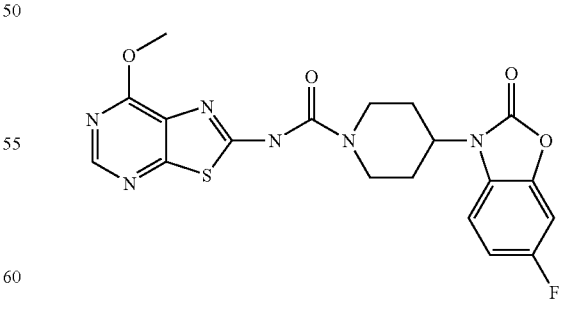

From 7-methoxy-thiazolo[5,4-d]pyrimidin-2-ylamine and 4-(6-Fluoro-2-oxo-benzooxazol-3-yl)-piperidine-1-carbonyl chloride: 4-(6-Fluoro-2-oxo-benzooxazol-3-yl)-piperidine-1-carboxylic acid (7-methoxy-thiazolo[5,4-d]pyrimidin-2-yl)-amide (184 mg, 75%) was obtained as a light brown solid; LRMS for $C_{19}H_{17}FN_6O_4S$ (M+H)$^+$ at m/z=444. The NMR spectrum obtained on the sample is compatible with its structure.

EXAMPLE 50

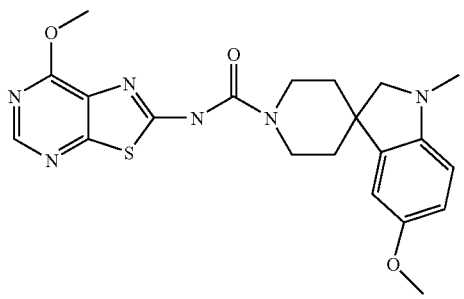

From 7-Methoxy-thiazolo[5,4-d]pyrimidin-2-ylamine and 5-Methoxy-1,2-Dihydro-1-methylspiro-[3H-indole-3,4'-piperidine]: 1,2-Dihydro-5-methoxy-N-(7-methoxythiazole[5,4-d]pyrimidin-2-yl)-1-methylspiro[3H-indole-3,4'-piperidine]-1'-carboxamide was obtained as a yellow solid; LRMS for $C_{21}H_{24}N_6O_3S$ (M+H)$^+$ at m/z=440. The NMR spectrum obtained on the sample is compatible with its structure.

EXAMPLE 51

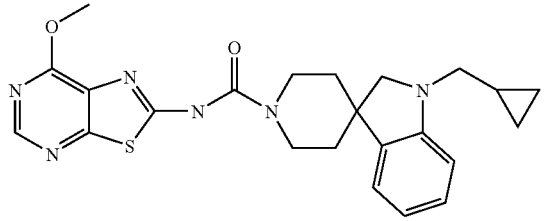

From 7-Methoxy-thiazolo[5,4-d]pyrimidin-2-ylamine and 1-(Cyclopropylmethyl)-1,2-dihydro-spiro[3H-indole-3,4'-piperidine] hydrochloride: 1-(Cyclopropylmethyl)-1,2-dihydro-N-(7-methoxythiazole[5,4-d]pyrimidin-2-yl)spiro[3H-indole-3,4'-piperidine]-1'-carboxamide was obtained as a yellow solid; LRMS for $C_{23}H_{26}N_6O_2S$ (M+H)$^+$ at m/z=450. The NMR spectrum obtained on the sample is compatible with its structure.

EXAMPLE 52

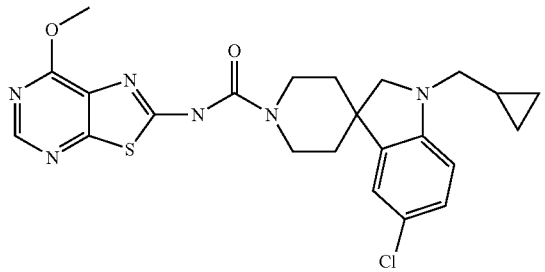

From 7-Methoxy-thiazolo[5,4-d]pyrimidin-2-ylamine and 5-Choro-1-(cyclopropylmethyl)-1,2-dihydro-spiro[3H-indole-3,4'-piperidine] hydrochloride: 1-(Cyclopropylmethyl)-1,2-dihydro-5-chloro-N-(7-methoxythiazole[5,4-d]pyrimidin-2-yl)spiro[3H-indole-3,4'-piperidine]-1-carboxamide was obtained as a yellow solid; LRMS for $C_{23}H_{25}ClN_6O_2S$ (M+H)$^+$ at m/z=484. The NMR spectrum obtained on the sample is compatible with its structure.

EXAMPLE 53

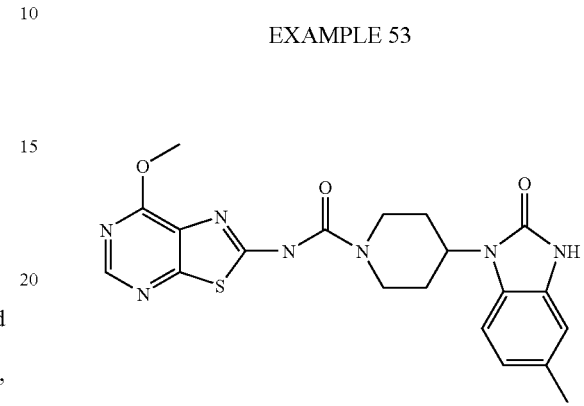

From 7-Methoxy-thiazolo[5,4-d]pyrimidin-2-ylamine and 5-Methyl-1-piperidin-4-yl-1,3-dihydro-benzoimidazol-2-one: 4-(5-Methyl-2-oxo-2,3-dihydro-benzoimidazol-1-yl)-piperidine-1-carboxylic acid (7-methoxy-thiazolo[5,4-d]pyrimidin-2-yl)amide was obtained as a light yellow solid; LRMS for $C_{20}H_{21}N_7O_3S$ (M+H)$^+$ at m/z=439. The NMR spectrum obtained on the sample is compatible with its structure.

EXAMPLE 54

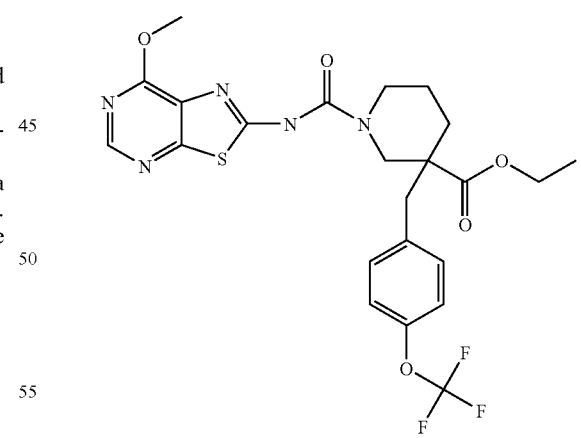

From 7-Methoxy-thiazolo[5,4-d]pyrimidin-2-ylamine and 3-(4-Trifluoromethoxy-benzyl)-piperidine-3-carboxylic acid ethyl ester: 1-(7-Methoxy-thiazolo[5,4-d]pyrimidin-2-ylcarbamoyl)-3-(4-trifluoromethoxy-benzyl)-piperidine-3-carboxylic acid ethyl ester was obtained as a yellow solid; LRMS for $C_{23}H_{24}F_3N_5O_5S$ (M+H)$^+$ at m/z=539. The NMR spectrum obtained on the sample is compatible with its structure.

EXAMPLE 55

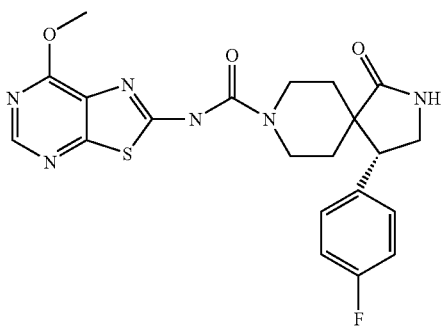

From 7-Methoxy-thiazolo[5,4-d]pyrimidin-2-ylamine and 4-(4-Fluoro-phenyl)-2,8-diaza-spiro[4.5]decan-1-one: 4-(4-Fluoro-phenyl)-1-oxo-2,8-diaza-spiro[4.5]decane-8-carboxylic acid (7-methoxy-thiazolo[5,4-d]pyrimidin-2-yl)-amide was obtained as a light brown solid; LRMS for $C_{21}H_{21}FN_6O_3S$ (M+H)$^+$ at m/z=456. The NMR spectrum obtained on the sample is compatible with its structure.

EXAMPLE 56

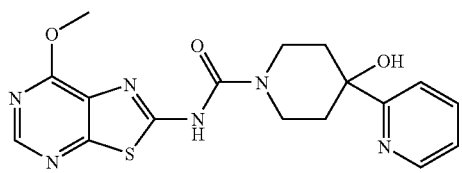

From 7-methoxy-thiazole[5,4-d]pyrimidin-2-ylamine and 4'-hydroxy-3',4',5',6'-tetrahydro-2'H-[2,4']bipyridinyl-1'-carbonyl chloride: 4'-Hydroxy-3',4',5',6'-tetrahydro-2H-[2,4']bipyridinyl-1'-carboxylic acid (7-methoxy-thiazolo[5,4-d]pyrimidin-2-yl)-amide was obtained as an off-white solid; LRMS for $C_{17}H_{18}N_6O_3S$ (M+H)$^+$ at m/z=386. The NMR spectrum obtained on the sample is compatible with its structure.

EXAMPLE 57

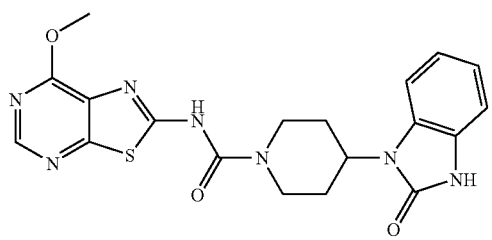

From 7-methoxy-thiazole[5,4-d]pyrimidin-2-ylamine and 4-(2-oxo-2,3-dihydro-benzoimidazol-1-yl)-piperidine-1-carbonyl chloride: 4-(2-Oxo-2,3-dihydro-benzoimidazol-1-yl)-piperidine-1-carboxylic acid (7-methoxy-thiazolo[5,4-d]pyrimidin-2-yl)-amide; ES-HRMS m/e calcd. for $C_{18}H_{20}N_7O_3S$ (M+H)$^+$ 426.1343, found 426.1344.

EXAMPLE 58

3,4-Dihydroxy-4-(3-trifluoromethyl-phenyl)-piperidine-1-carboxylic acid (7-methoxy-thiazolo[5,4-d]pyrimidin-2-yl)-amide

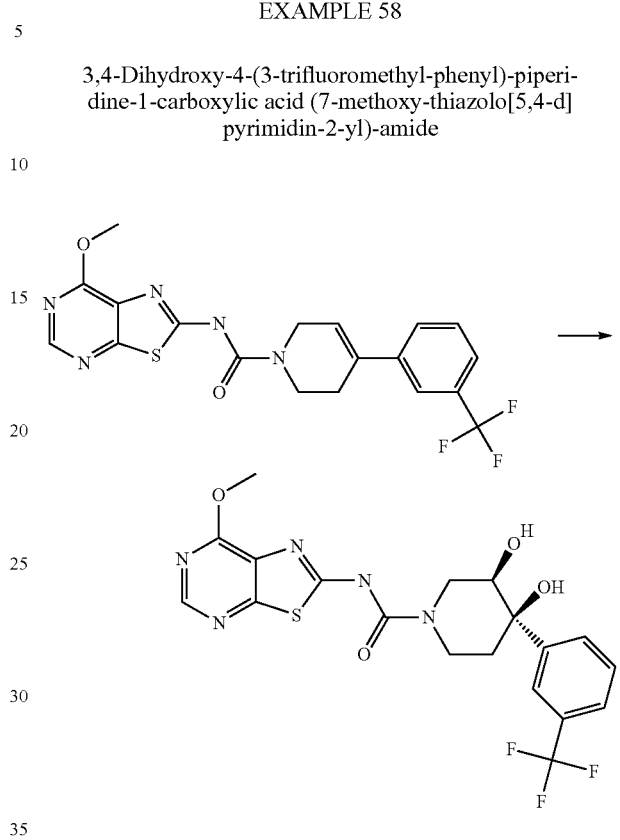

A mixture of 4-(3-Trifluoromethyl-phenyl)-3,6-dihydro-2H-pyridine-1-carboxylic acid (7-methoxy-thiazolo[5,4-d]pyrimidin-2-yl)-amide (from Example 67) (100 mg, 0.23 mmol), N-methylmorpholine N-oxide (60 mg, 0.51 mmol) and osmium tetroxide (4 wt. % in water, 13 μL, 0.053 mmol) in acetone (9 mL) and water (1 mL) was stirred at room temperature overnight. The reaction mixture was quenched with sodium hydrogen sulfate and stirred at room temperature for 10 minutes. The mixture was filtered and the filtrate was diluted with methanol and absorbed onto silica gel. Column chromatography (6→10% methanol/methylene chloride) gave 3,4-Dihydroxy-4-(3-trifluoromethyl-phenyl)-piperidine-1-carboxylic acid (7-methoxy-thiazolo[5,4-d]pyrimidin-2-yl)-amide (25 mg, 23% yield) as a light brown powder; LRMS for $C_{19}H_{18}F_3N_5O_4S$ (M+H)$^+$ at m/z=470. The NMR spectrum obtained on the sample is compatible with its structure.

EXAMPLE 59

Synthesis of 4-(3,4-dihydro-1H-isoquinolin-2-yl)-piperidine-1-carboxylic acid (7-methoxy-thiazolo[5,4-d]pyrimidin-2-yl)-amide trifluoroacetate

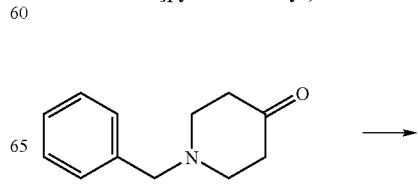

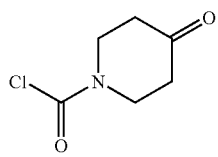

Step 1: A solution of triphosgene (2.84 g, 9.6 mmol) in methylene chloride (100 mL) at 0° C. was treated with a solution of 1-benzyl-piperidin-4-one (6.0 g, 31.7 mmol) in methylene chloride (100 mL). The reaction mixture was allowed to warm to 25° C. and was stirred at 25° C. overnight. At this time, the mixture was concentrated in vacuo. Flash chromatography (Merck Silica gel 60, 230-400 mesh, gradient elution 60/40 ethyl acetate/hexanes) afforded 4-oxo-piperidine-1-carbonyl chloride (3.9 g, 76%) as a brown oil. The NMR spectrum obtained on the sample is compatible with its structure.

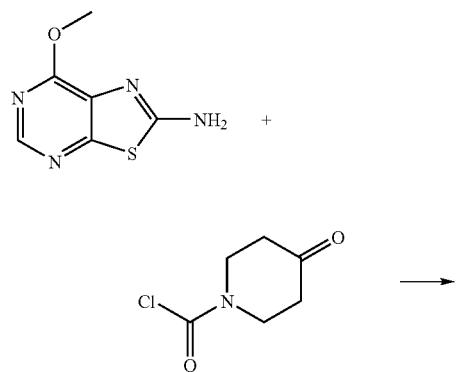

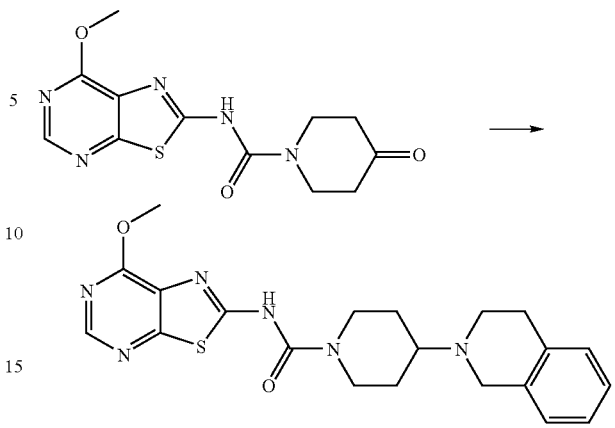

Step 3: A solution of 4-oxo-piperidine-1-carboxylic acid (7-methoxy-thiazolo[5,4-d]pyrimidin-2-yl)-amide (50 mg, 0.16 mmol) in methanol (5 mL) at 25° C. was treated with 1,2,3,4-tetrahydro-isoquinoline (22 mg, 0.16 mmol), acetic acid (28 mL, 0.49 mmol) and sodium cyanoborohydride (30 mg, 0.48 mmol). The reaction mixture was stirred at 25° C. overnight. At this time, the reaction was concentrated in vacuo. High pressure liquid chromatography (acetonitrile/0.1% trifluroacetic acid-water/0.1% trifluoroacetic acid 10-90% gradient) afforded 4-(3,4-dihydro-1H-isoquinolin-2-yl)-piperidine-1-carboxylic acid (7-methoxy-thiazolo[5,4-d]pyrimidin-2-yl)-amide trifluoroacetate (18 mg, 21%) as a white solid; LRMS for $C_{21}H_{24}N_6O_2S$ (M+H)$^+$ at m/z=425. The NMR spectrum obtained on the sample is compatible with its structure.

In an analogous manner, the compounds of Examples 60-64 were obtained as follows:

EXAMPLE 60

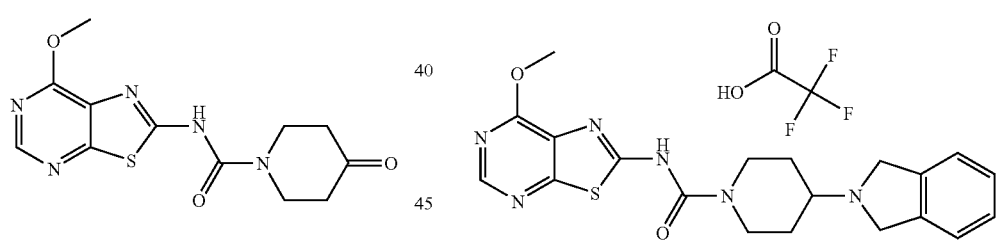

Step 2: A solution of 7-methoxy-thiazolo[5,4-d]pyrimidin-2-ylamine (2.2 g, 12.1 mmol) in tetrahydrofuran (70 mL) at 25° C. was treated with sodium hydride (60% in mineral oil, 1.45 g, 36 mmol). A slight evolution of gas was observed. The resulting purple slurry was warmed to 70° C. for 1 h. At this time, the reaction was cooled to 25° C. and was treated with N,N-diisopropylethylamine (6.5 mL, 37.4 mmol) and a solution of 4-oxo-piperidine-1-carbonyl chloride (3.9 g, 24.2 mmol) in tetrahydrofuran (10 mL). The reaction was stirred at 70° C. overnight. At this time, the reaction was concentrated in vacuo, dissolved in methanol and absorbed onto silica gel (6 g). The silica gel was divided into two equal lots. ISCO chromatography (120 g, Silica, gradient elution 5/95 methanol/methylene chloride) afforded an impure, dark brown solid (1.09 g). Trituration of the solid from ethyl acetate afforded 4-oxo-piperidine-1-carboxylic acid (7-methoxy-thiazolo[5,4-d]pyrimidin-2-yl)-amide (0.88 g, 24%) as a light brown solid; LRMS for $C_{12}H_{13}N_5O_3S$ (M+H)$^+$ at m/z=308. The NMR spectrum obtained on the sample is compatible with its structure.

From 4-oxo-piperidine-1-carboxylic acid (7-methoxy-thiazolo[5,4-d]pyrimidin-2-yl)-amide and 2,3-dihydro-1H-isoindole: 4-(1,3-Dihydro-isoindol-2-yl)-piperidine-1-carboxylic acid (7-methoxy-thiazolo[5,4-d]pyrimidin-2-yl)-amide trifluoroacetate as a light brown solid; LRMS for $C_{20}H_{22}N_6O_2S$ (M+H)$^+$ at m/z=411.

EXAMPLE 61

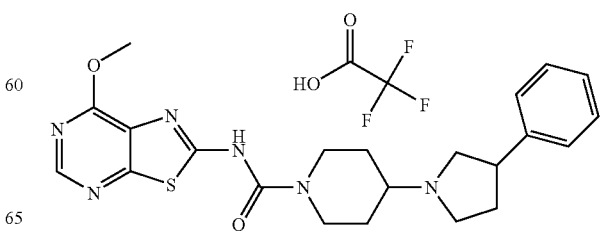

From 4-oxo-piperidine-1-carboxylic acid (7-methoxy-thiazolo[5,4-d]pyrimidin-2-yl)-amide and 3-phenyl-pyrrolidine: 4-(3-Phenyl-pyrrolidin-1-yl)-piperidine-1-carboxylic acid (7-methoxy-thiazolo[5,4-d]pyrimidin-2-yl)-amine trifluoroacetate as a light brown solid; LRMS for $C_{22}H_{26}N_6O_2S$ (M+H)$^+$ at m/z=439.

EXAMPLE 62

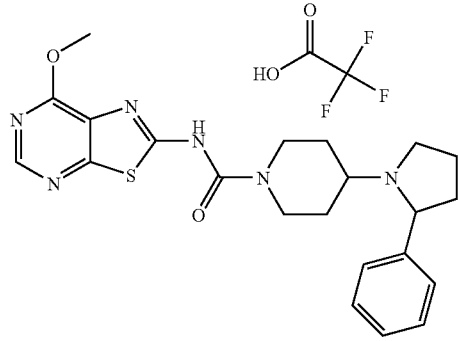

From 4-oxo-piperidine-1-carboxylic acid (7-methoxy-thiazolo[5,4-d]pyrimidin-2-yl)-amide and 2-phenyl-pyrrolidine: 4-(2-Phenyl-pyrrolidin-1-yl)-piperidine-1-carboxylic acid (7-methoxy-thiazolo[5,4-d]pyrimidin-2-yl)-amide trifluoroacetate as a light brown solid; LRMS for $C_{22}H_{26}N_6O_2S$ (M+H)$^+$ at m/z=439.

EXAMPLE 63

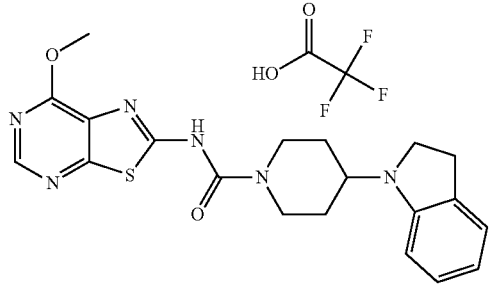

From 4-oxo-piperidine-1-carboxylic acid (7-methoxy-thiazolo[5,4-d]pyrimidin-2-yl)-amide and 2,3-dihydro-1H-indole: 4-(2,3-Dihydro-indol-1-yl)-piperidine-1-carboxylic acid (7-methoxy-thiazolo[5,4-d]pyrimidin-2-yl)-amide trifluoroacetate as a light brown solid; LRMS for $C_{20}H_{22}N_6O_2S$ (M+H)$^+$ at m/z=411.

EXAMPLE 64

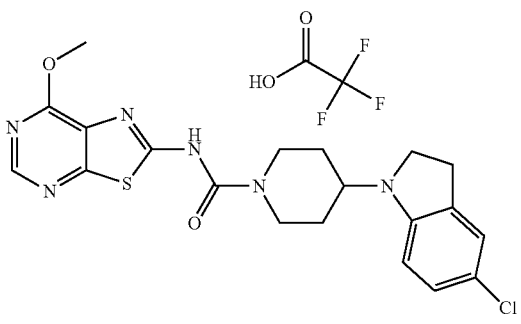

From 4-oxo-piperidine-1-carboxylic acid (7-methoxy-thiazolo[5,4-d]pyrimidin-2-yl)-amide and 5-chloro-2,3-dihydro-1H-indole: 4-(5-Chloro-2,3-dihydro-indol-1-yl)-piperidine-1-carboxylic acid (7-methoxy-thiazolo[5,4-d]pyrimidin-2-yl)-amide trifluoroacetate as a light brown powder; LRMS for $C_{20}H_{21}N_6O_2S$ (M+H)$^+$ at m/z=445.

EXAMPLE 65

Synthesis of 4-Hydroxy-4-(3-trifluoromethyl-phenyl)-piperidine-1-carboxylic acid (7-methoxy-thiazolo[5,4-d]pyrimidin-2-yl)-amide

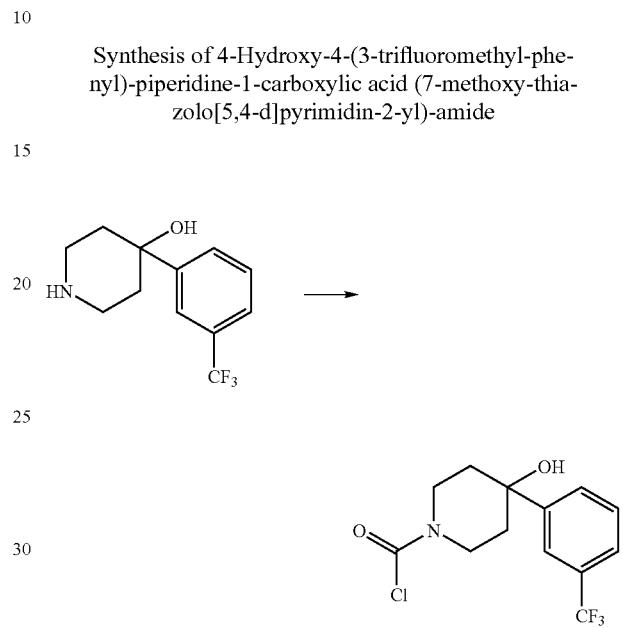

Step 1: A solution of triphosgene (3.26 g, 0.011 mol) and anhydrous tetrahydrofuran (1000 mL) cooled to −20° C. was treated with pyridine (4.45 mL, 0.055 mol). The resulting cloudy suspension was slowly treated with a solution of 4-(3-trifluoromethyl-phenyl)-piperidin-4-ol (9 g, 0.036 mol) in anhydrous tetrahydrofuran (45 mL) while the internal temperature was maintained between −20° C. to −30° C. The resulting mixture was transferred to an ice bath which was allowed to come to 25° C. overnight to give a light brown solution with a small amount of brown precipitates. The reaction mixture was then concentrated in vacuo to give a brown solid. Flash chromatography (Merck Silica gel 60, 230-400 mesh, 75/25 hexanes/ethyl acetate) afforded 4-hydroxy-4-(3-trifluoromethyl-phenyl)-piperidine-1-carbonyl chloride (6.89 g, 61%) as a clear, viscous oil. The NMR spectrum obtained on the sample is compatible with its structure.

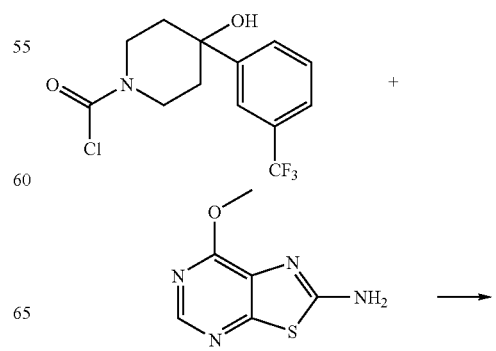

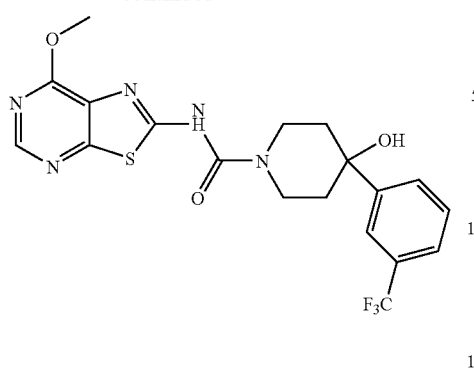

Step 2: A mixture of 7-methoxy-thiazolo[5,4-d]pyrimidin-2-ylamine (2.72 g, 0.015 mol) in tetrahydrofuran (250 mL) at 25° C. was treated with sodium hydride (60% in mineral oil, 1.79 g, 0.045 mol). The slurry was warmed to 50° C. for 1 h and then cooled to 0° C. in an ice bath. The cooled reaction mixture was treated with N,N-diisopropylethylamine (7.8 mL, 0.045 mol) and a solution of 4-hydroxy-4-(3-trifluoromethyl-phenyl)-piperidine-1-carbonyl chloride (6.5 g, 0.021 mol) in tetrahydrofuran (50 mL). The reaction mixture was allowed to come to 25° C. overnight. At this time, the mixture was concentrated in vacuo to give a brown solid which was taken up in ethyl acetate (600 mL). The organics were washed with a 1N aqueous hydrochloric acid solution (2×200 mL), water (1×200 mL) and a saturated aqueous sodium chloride solution (1×200 mL), dried over magnesium sulfate, filtered and concentrated in vacuo. ISCO chromatography (330 g, Silica, gradient elution 8/92 methanol/methylene chloride) afforded a light brown solid (3.81 g). The solid was triturated twice from methylene chloride to afford 4-hydroxy-4-(3-trifluoromethyl-phenyl)-piperidine-1-carboxylic acid (7-methoxy-thiazolo[5,4-d]pyrimidin-2-yl)-amide (3.32 g, 49%) as a white solid; LRMS for $C_{19}H_{18}F_3N_5O_3S$ (M+H)$^+$ at m/z=454. The NMR spectrum obtained on the sample is compatible with its structure.

In an analogous manner, the compounds of Examples 66-78 were obtained as follows:

EXAMPLE 66

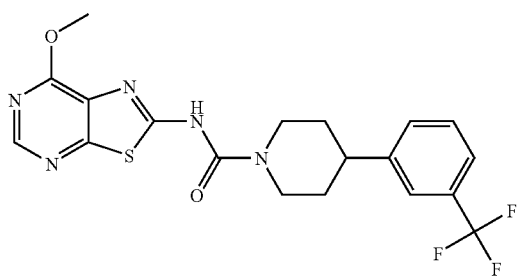

From 7-methoxy-thiazolo[5,4-d]pyrimidin-2-ylamine and 4-(3-trifluoromethyl-phenyl)-piperidine-1-carbonyl chloride: 4-(3-Trifluoromethyl-phenyl)-piperidine-1-carboxylic acid (7-methoxy-thiazolo[5,4-d]pyrimidin-2-yl)-amide as an off-white solid; LRMS for $C_{19}H_{18}F_3N_5O_2S$ (M+H)$^+$ at m/z=438. The NMR spectrum obtained on the sample is compatible with its structure.

EXAMPLE 67

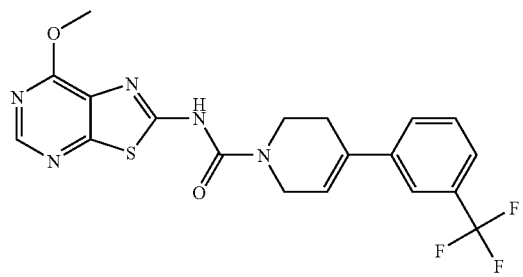

From 7-methoxy-thiazolo[5,4-d]pyrimidin-2-ylamine and 4-(3-trifluoromethyl-phenyl)-3,6-dihydro-2H-pyridine-1-carbonyl chloride: 4-(3-Trifluoromethyl-phenyl)-3,6-dihydro-2H-pyridine-1-carboxylic acid (7-methoxy-thiazolo[5,4-d]pyrimidin-2-yl)-amide as a light brown solid; LRMS for $C_{19}H_{16}F_3N_5O_2S$ (M+H)$^+$ at m/z=436. The NMR spectrum obtained on the sample is compatible with its structure.

EXAMPLE 68

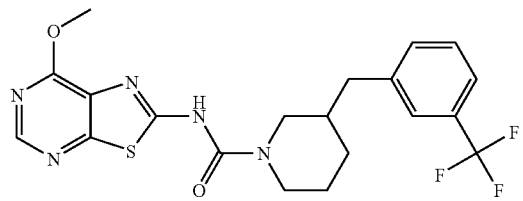

From 7-methoxy-thiazolo[5,4-d]pyrimidin-2-ylamine and 3-(3-trifluoromethyl-benzyl)-piperidine-1-carbonyl chloride: 3-(3-Trifluoromethyl-benzyl)-piperidine-1-carboxylic acid (7-methoxy-thiazolo[5,4-d]pyrimidin-2-yl)-amide as a light brown solid; LRMS for $C_{20}H_{20}F_3N_5O_2S$ (M+H)$^+$ at m/z=452. The NMR spectrum obtained on the sample is compatible with its structure.

EXAMPLE 69

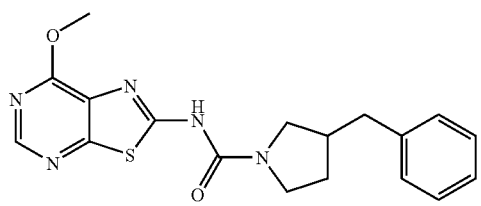

From 7-methoxy-thiazolo[5,4-d]pyrimidin-2-ylamine and 3-benzyl-pyrrolidine-1-carbonyl chloride: 3-Benzyl-pyrrolidine-1-carboxylic acid (7-methoxy-thiazolo[5,4-d]pyrimidin-2-yl)-amide as an off-white solid; LRMS for $C_{18}H_{19}N_5O_2S$ (M+H)+ at m/z=370. The NMR spectrum obtained on the sample is compatible with its structure.

EXAMPLE 70

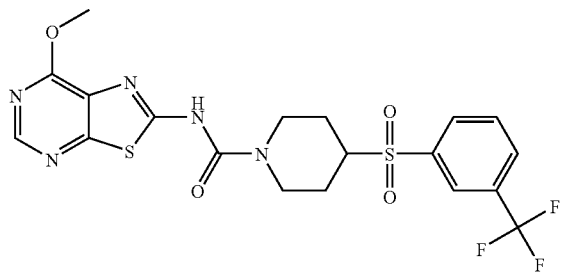

From 7-methoxy-thiazolo[5,4-d]pyrimidin-2-ylamine and 4-(3-trifluoromethyl-benzenesulfonyl)-piperidine-1-carbonyl chloride: 4-(3-Trifluoromethyl-benzenesulfonyl)-piperidine-1-carboxylic acid (7-methoxy-thiazolo[5,4-d]pyrimidin-2-yl)-amide as a brown solid; LRMS for $C_{19}H_{18}F_3N_5O_4S_2$ (M+H)+ at m/z=502. The NMR spectrum obtained on the sample is compatible with its structure.

EXAMPLE 71

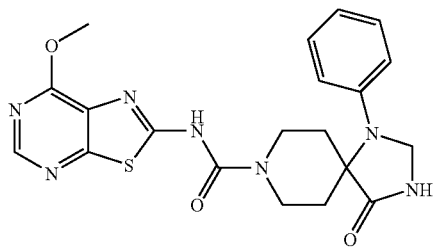

From 7-methoxy-thiazolo[5,4-d]pyrimidin-2-ylamine and 4-oxo-1-phenyl-1,3,8-triaza-spiro[4.5]decane-8-carbonyl chloride: 4-Oxo-1-phenyl-1,3,8-triaza-spiro[4.5]decane-8-carboxylic acid (7-methoxy-thiazolo[5,4-d]pyrimidin-2-yl)-amide as a light brown solid; LRMS for $C_{20}H_{21}N_7O_3S$ (M+H)+ at m/z=440. The NMR spectrum obtained on the sample is compatible with its structure.

EXAMPLE 72

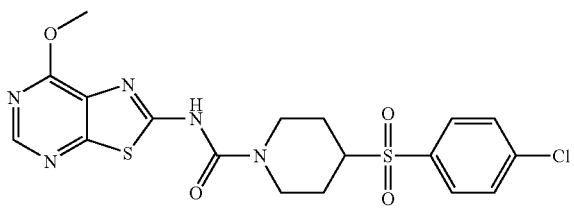

From 7-methoxy-thiazolo[5,4-d]pyrimidin-2-ylamine and 4-(4-chloro-benzenesulfonyl)-piperidine-1-carbonyl chloride: 4-(4-Chloro-benzenesulfonyl)-piperidine-1-carboxylic acid (7-methoxy-thiazolo[5,4-d]pyrimidin-2-yl)-amide as a white solid; LRMS for $C_{18}H_{18}ClN_5O_4S_2$ (M+H)+ at m/z=468. The NMR spectrum obtained on the sample is compatible with its structure.

EXAMPLE 73

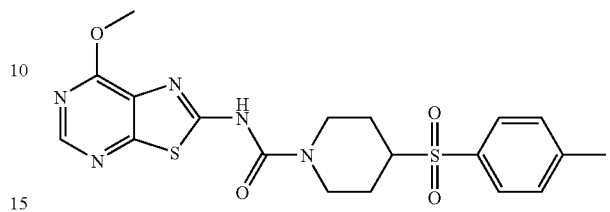

From 7-methoxy-thiazolo[5,4-d]pyrimidin-2-ylamine and 4-(toluene-4-sulfonyl)-piperidine-1-carbonyl chloride: 4-(Toluene-4-sulfonyl)-piperidine-1-carboxylic acid (7-methoxy-thiazolo[5,4-d]pyrimidin-2-yl)-amide as a white solid; LRMS for $C_{19}H_{21}N_5O_4S_2$ (M+H)+ at m/z=448. The NMR spectrum obtained on the sample is compatible with its structure.

EXAMPLE 74

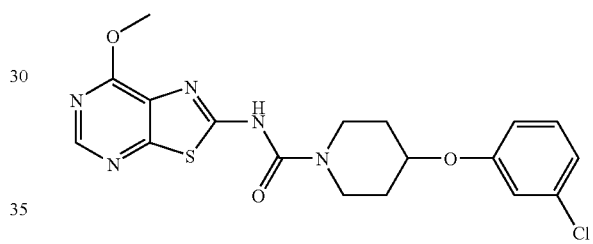

From 7-methoxy-thiazolo[5,4-d]pyrimidin-2-ylamine and 4-(3-chloro-phenoxy)-piperidine-1-carbonyl chloride: 4-(3-Chloro-phenoxy)-piperidine-1-carboxylic acid (7-methoxy-thiazolo[5,4-d]pyrimidin-2-yl)-amide as a off-white solid; LRMS for $C_{18}H_{18}ClN_5O_3S$ (M+H)+ at m/z=420. The NMR spectrum obtained on the sample is compatible with its structure.

EXAMPLE 75

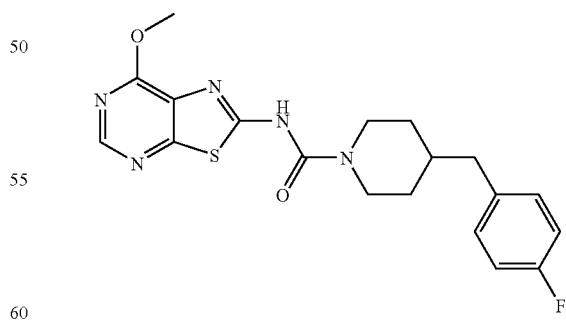

(k) From 7-methoxy-thiazolo[5,4-d]pyrimidin-2-ylamine and 4-(4-fluoro-benzyl)-piperidine-1-carbonyl chloride: 4-(4-Fluoro-benzyl)-piperidine-1-carboxylic acid (7-methoxy-thiazolo[5,4-d]pyrimidin-2-yl)-amide as a light brown solid; LRMS for $C_{19}H_{20}FN_5O_2S$ (M+H)+ at m/z=402. The NMR spectrum obtained on the sample is compatible with its structure.

EXAMPLE 76

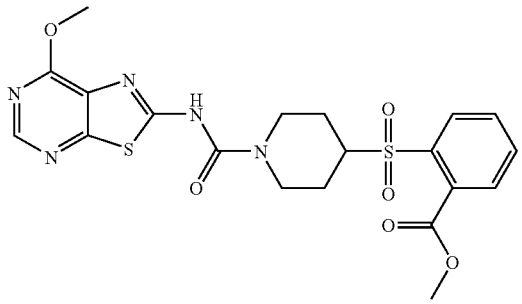

From 7-methoxy-thiazolo[5,4-d]pyrimidin-2-ylamine and 2-(1-chlorocarbonyl-piperidine-4-sulfonyl)-benzoic acid methyl ester: 2-[1-(7-Methoxy-thiazolo[5,4-d]pyrimidin-2-ylcarbamoyl)-piperidine-4-sulfonyl]-benzoic acid methyl ester as a light brown solid; LRMS for $C_{20}H_{21}N_5O_6S_2$ $(M+H)^+$ at m/z=492. The NMR spectrum obtained on the sample is compatible with its structure.

EXAMPLE 77

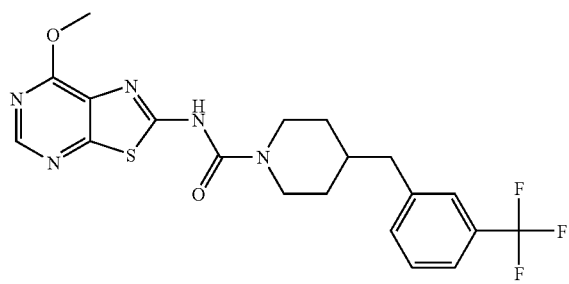

From 7-methoxy-thiazolo[5,4-d]pyrimidin-2-ylamine and 4-(3-trifluoromethyl-benzyl)-piperidine-1-carbonyl chloride: 4-(3-Trifluoromethyl-benzyl)-piperidine-1-carboxylic acid (7-methoxy-thiazolo[5,4-d]pyrimidin-2-yl)-amide as a light brown solid; LRMS for $C_{20}H_{20}F_3N_5O_2S$ $(M+H)^+$ at m/z=452. The NMR spectrum obtained on the sample is compatible with its structure.

EXAMPLE 78

Synthesis of 4-(3-chloro-phenyl)-4-hydroxy-piperidine-1-carboxylic acid (7-methoxy-thiazolo[5,4-d]pyrimidin-2-yl)-amide

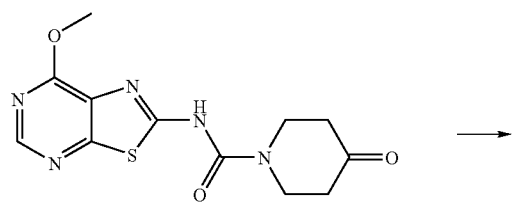

→

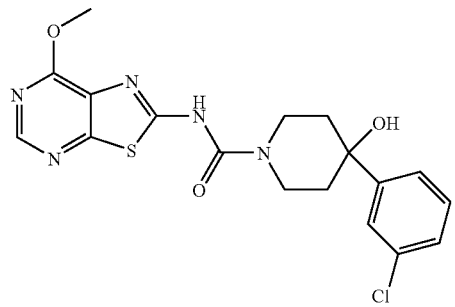

A solution of 4-oxo-piperidine-1-carboxylic acid (7-methoxy-thiazolo[5,4-d]pyrimidin-2-yl)-amide (as prepared in Example 59, 100 mg, 0.33 mmol) in tetrahydrofuran (35 mL) cooled to 0° C. was treated with 3-chlorophenyl magnesium bromide (0.5 M in tetrahydrofuran, 1.6 mL, 0.8 mmol). The resulting mixture was stirred at 25° C. for 3 h. At this time, the reaction mixture was cooled to 0° C. and was treated with an additional amount of 3-chlorophenyl magnesium bromide (0.5 M in tetrahydrofuran, 6 mL, 3.0 mmol). The mixture was then allowed to warm to 25° C. and to stir at 25° C. overnight. At this time, the reaction was quenched with methanol and absorbed onto silica gel (6 g). ISCO chromatography (120 g, Silica, gradient elution 7/93 methanol/methylene chloride) afforded 4-(3-chloro-phenyl)-4-hydroxy-piperidine-1-carboxylic acid (7-methoxy-thiazolo[5,4-d]pyrimidin-2-yl)-amide (61 mg, 44%) as a light brown solid; LRMS for $C_{18}H_{18}ClN_5O_3S$ $(M+H)^+$ at m/z=420. The NMR spectrum obtained on the sample is compatible with its structure.

In an analogous manner, the compound of Example 79 was obtained as follows:

EXAMPLE 79

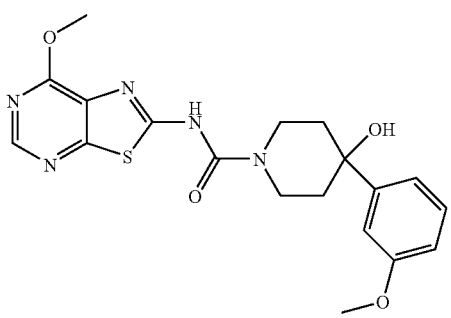

From 4-oxo-piperidine-1-carboxylic acid (7-methoxy-thiazolo[5,4-d]pyrimidin-2-yl)-amide and 3-methoxyphenyl magnesium bromide: 4-Hydroxy-4-(3-methoxy-phenyl)-piperidine-1-carboxylic acid (7-methoxy-thiazolo[5,4-d]pyrimidin-2-yl)-amide as a light brown solid; LRMS for $C_{19}H_{21}N_5O_4S$ $(M+H)^+$ at m/z=416. The NMR spectrum obtained on the sample is compatible with its structure.

EXAMPLE 80

Synthesis of 4'-hydroxy-6-trifluoromethyl-3',4',5',6'-tetrahydro-2'H-[2,4']bipyridinyl-1'-carboxylic acid (7-methoxy-thiazolo[5,4-d]pyrimidin-2-yl)-amide

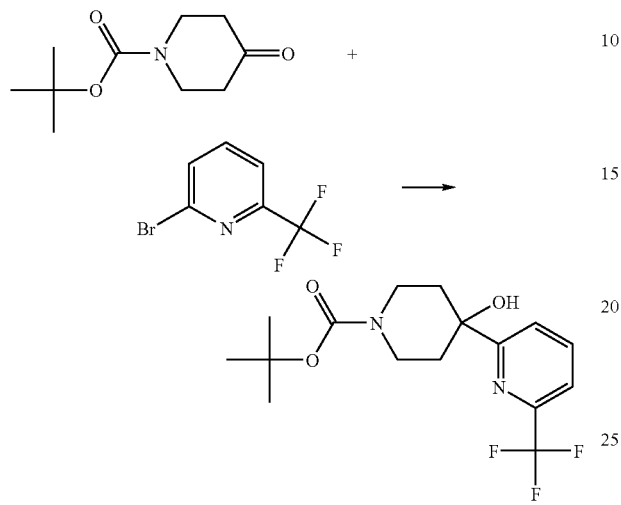

Step 1: A mixture of 2-bromo-6-(trifluoromethyl)pyridine (300 mg, 1.33 mmol) in tetrahydrofuran (10 mL) under a nitrogen atmosphere cooled to −78° C. was treated with n-butyl lithium (2M solution in tetrahydrofuran, 0.83 mL, 1.33 mmol). The mixture was stirred at −78° C. for 15 min. At this time, the reaction was treated with 1-boc-4-piperidone (265 mg, 1.33 mmol). The mixture was then allowed to slowly warm to 25° C. and was stirred at 25° C. for 1 h. At this time, the reaction was poured into water. The aqueous layer was extracted with ethyl acetate. The organics were washed with a saturated aqueous sodium chloride solution, dried over magnesium sulfate, filtered, and concentrated in vacuo to afford 4'-hydroxy-6-trifluoromethyl-3',4',5',6'-tetrahydro-2'H-[2,4']bipyridinyl-1'-carboxylic acid tert-butyl ester (450 mg, 98%) as a yellow oil; LRMS for $C_{16}H_{21}F_3N_2O_3$ (M+H)$^+$ at m/z=346. The NMR spectrum obtained on the sample is compatible with its structure.

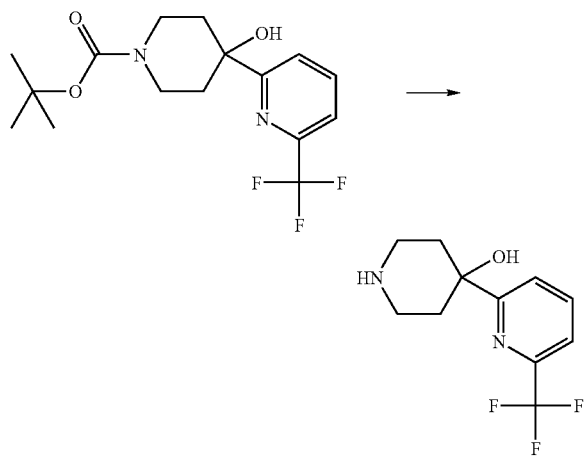

Step 2: A mixture of 4'-hydroxy-6-trifluoromethyl-3',4',5',6'-tetrahydro-2'H-[2,4']bipyridinyl-1'-carboxylic acid tert-butyl ester (450 mg, 1.30 mmol) in methylene chloride (5 mL) was treated with trifluoroacetic acid (5 mL). The reaction was stirred at 25° C. for 30 min. At this time, the reaction was concentrated in vacuo to give yellow oil. The oil was dissolved in methylene chloride, washed with a saturated aqueous sodium bicarbonate solution and a saturated aqueous sodium chloride solution, dried over magnesium sulfate, filtered, and concentrated in vacuo to afford 6-trifluoromethyl-2',3',5',6'-tetrahydro-1'H-[2,4']bipyridinyl-4'-ol (320 mg, 100%) as a yellow oil; LRMS for $C_{11}H_{13}F_3N_2O_3$ (M+H)$^+$ at m/z=246. The NMR spectrum obtained on the sample is compatible with its structure.

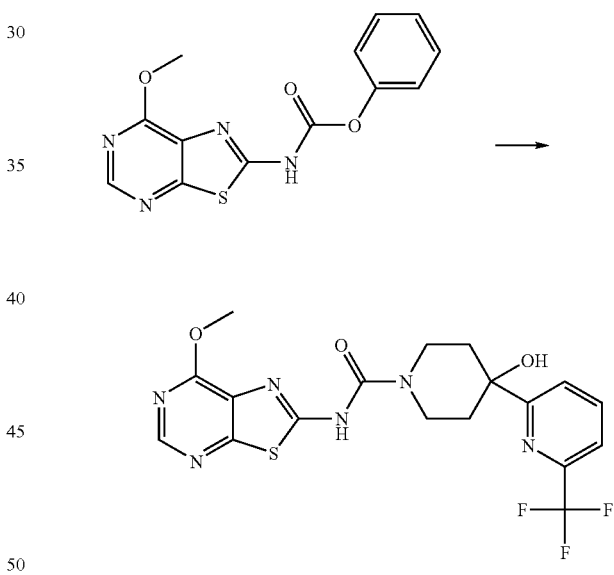

Step 3: A mixture of 6-trifluoromethyl-2',3',5',6'-tetrahydro-1'H-[2,4']bipyridinyl-4'-ol (320 mg, 1.30 mmol) in acetonitrile (15 mL) was treated with (7-methoxy-thiazolo[5,4-d]pyrimidin-2-yl)-carbamic acid phenyl ester (360 mg, 1.18 mmol). The mixture was stirred at reflux for 2 h. At this time, the reaction was poured into a saturated aqueous sodium bicarbonate solution. The aqueous layer was extracted with methylene chloride. The organics were washed with a saturated aqueous sodium chloride solution, dried over magnesium sulfate, filtered, and concentrated in vacuo. Flash chromatography (Merck Silica gel 60, 230-400 mesh, 98/2 methylene chloride/methanol) afforded 4'-hydroxy-6-trifluoromethyl-3',4',5',6'-tetrahydro-2'H-[2,4']bipyridinyl-1'-carboxylic acid (7-methoxy-thiazolo[5,4-d]pyrimidin-2-yl)-amide (94 mg, 17%) as a white solid; LRMS for $C_{18}H_{17}F_3N_6O_3S$ (M+H)$^+$ at m/z=454. The NMR spectrum obtained on the sample is compatible with its structure.

EXAMPLE 81

Synthesis of 4-Acetylamino-4-(3-trifluoromethyl-phenyl)-piperidine-1-carboxylic acid (7-methoxy-thiazolo[5,4-d]pyrimidin-2-yl)-amide

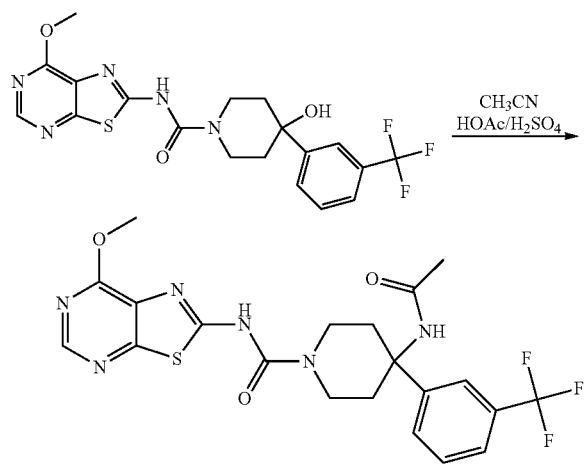

A solution of 4-hydroxy-4-(3-trifluoromethyl-phenyl)-piperidine-1-carboxylic acid (7-methoxy-thiazolo[5,4-d]pyrimidin-2-yl)-amide (prepared in Example 65, 100 mg, 0.22 mmol) in acetonitrile (0.16 mL) and glacial acetic acid (0.21 mL) cooled to 0 C was treated dropwise with concentrated sulfuric acid (0.21 mL). The resulting mixture was then allowed to warm to 25° C. After stirring for 2 h, the reaction mixture was diluted with water, neutralized with a saturated sodium bicarbonate solution and extracted with ethyl acetate. The extracts were dried over sodium sulfate, filtered and concentrated in vacuo. High pressure liquid chromatography (acetonitrile/0.1% trifluoroacetic acid/water gradient) followed by lyophilization of the desired fractions afforded 4-acetylamino-4-(3-trifluoromethyl-phenyl)-piperidine-1-carboxylic acid (7-methoxy-thiazolo[5,4-d]pyrimidin-2-yl)-amide (37 mg, 28%) as a white powder; ES-HRMS m/e calcd. for $C_{21}H_{22}N_6O_3SF_3$ (M+H)$^+$ 495.1421, found 495.1424.

EXAMPLE 82

Synthesis of 4-Amino-4-(3-trifluoromethyl-phenyl)-piperidine-1-carboxylic acid (7-methoxy-thiazolo[5,4-d]pyrimidin-2-yl)-amide hydrochloride salt

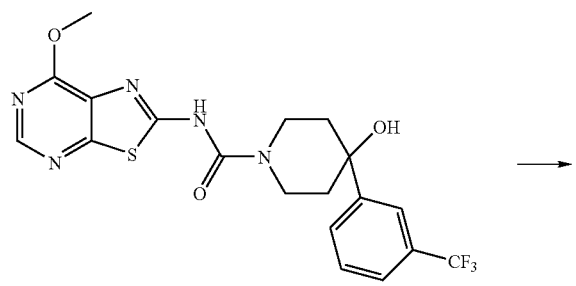

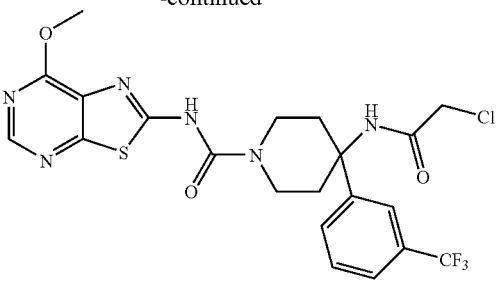

Step 1: A mixture of 4-hydroxy-4-(3-trifluoromethyl-phenyl)-piperidine-1-carboxylic acid (7-methoxy-thiazolo[5,4-d]pyrimidin-2-yl)-amide (prepared as in Example 65, 114 mg, 0.25 mmol) in acetic acid (0.24 mL) was treated with chloroacetonitrile (0.20 mL, 3.10 mmol). The resulting mixture was sonicated in a water bath until all the solid dissolved and then was cooled to 0° C. The reaction was then treated with concentrated sulfuric acid (0.24 mL) at 0° C. Upon complete addition, the reaction was warmed to 25° C. and was stirred at 25° C. for 2 h. At this time, the mixture was diluted with water and was extracted with ethyl acetate. The organics were washed with a saturated aqueous sodium bicarbonate solution and a saturated aqueous sodium chloride solution, dried over sodium sulfate, filtered and concentrated in vacuo. The resulting material was triturated with diethyl ether to afford 4-(2-chloro-acetylamino)-4-(3-trifluoromethyl-phenyl)-piperidine-1-carboxylic acid (7-methoxy-thiazolo[5,4-d]pyrimidin-2-yl)-amide (88 mg, 67%) as an off-white solid. This material was used without further purification.

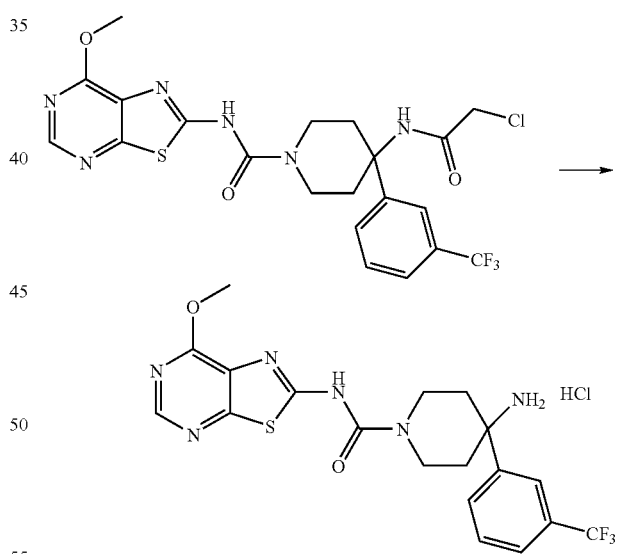

Step 2: A mixture of 4-(2-chloro-acetylamino)-4-(3-trifluoromethyl-phenyl)-piperidine-1-carboxylic acid (7-methoxy-thiazolo[5,4-d]pyrimidin-2-yl)-amide (81 mg, 0.15 mmol) and thiourea (15.4 mg, 0.20 mmol) in ethanol/acetic acid (0.5 mL of a 5:1 ethanol/acetic acid mixture) was heated to 80° C. in a sealed tube for 18 h. At this time, the mixture was allowed to cool to 25° C., diluted with water (5 mL) and filtered. The filtrate was neutralized with a 1N aqueous sodium hydroxide solution and was then extracted with ethyl acetate. The organics were washed with a saturated aqueous sodium chloride solution, dried over sodium sulfate, filtered and concentrated in vacuo to give 35 mg of crude material. This material was dissolved in methanol/methylene chloride and loaded onto 2 silica gel preparative thin layer chromatography plates (0.5 mm thick) which were then eluted with 10% methanol/methylene chloride to give a white powder (26 mg). This material was then dissolved in dioxane and treated with a solution of 4N hydrochloric acid in dioxane (1 mL). The resulting solution was then concentrated and lyophilized to afford the hydrochloride salt of 4-amino-4-(3-trifluoromethyl-phenyl)-piperidine-1-carboxylic acid (7-methoxy-thiazolo[5,4-d]pyrimidin-2-yl)-amide (27 mg, 37%) as a light yellow solid; ES-HRMS m/e calcd. for $C_{19}H_{20}N_6O_2SF_3$(M+H)$^+$ 453.1315, found 453.

EXAMPLE 83

Synthesis of 4-(4-fluoro-3-trifluoromethyl-benzylamino)-piperidine-1-carboxylic acid (7-methoxy-thiazolo[5,4-d]pyrimidin-2-yl)-amide

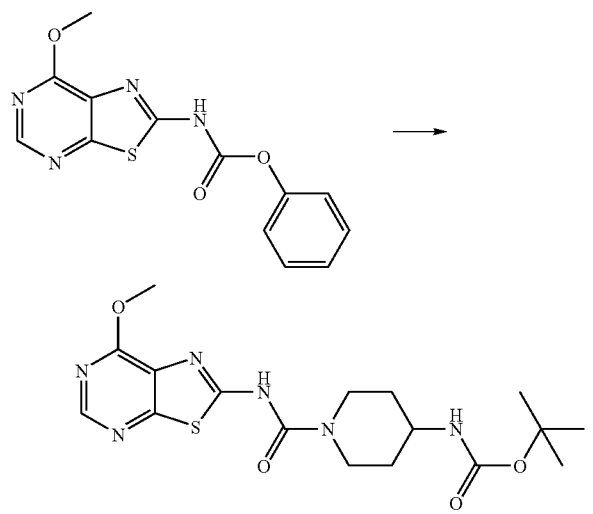

Step 1: A solution of (7-methoxy-thiazolo[5,4-d]pyrimidin-2-yl)-carbamic acid phenyl ester (6 g, 19.8 mmol) and piperidin-4-yl-carbamic acid tert-butyl ester (4.37 g, 21.8 mmol) in acetonitrile (400 mL) was heated to reflux for 1 h and was then stirred at 25° C. overnight. The resulting solid was collected by filtration, rinsed with acetonitrile and dried in vacuo to afford [1-(7-methoxy-thiazolo[5,4-d]pyrimidin-2-ylcarbamoyl)-piperidin-4-yl]-carbamic acid tert-butyl ester (7.3 g, 90%) as a white solid; ES-HRMS m/e calcd for $C_{17}H_{24}N_6O_4S$ (M+H)$^+$ 409.1653, found 409.1653.

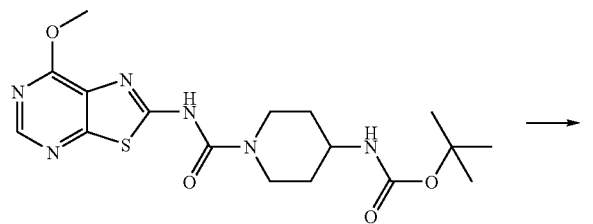

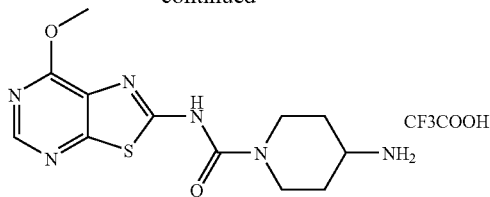

Step 2: A mixture of [1-(7-methoxy-thiazolo[5,4-d]pyrimidin-2-ylcarbamoyl)-piperidin-4-yl]-carbamic acid tert-butyl ester (14.5 g) and trifluoroacetic acid (100 mL) was stirred at 25° C. for 1 h. The reaction was then concentrated in vacuo. The resulting residue was triturated with ether and dried in vacuo to afford the trifluoroacetic acid salt of 4-amino-piperidine-1-carboxylic acid (7-methoxy-thiazolo[5,4-d]pyrimidin-2-yl)-amide (14.4 g, 100%) as a white solid.

Step 3: A suspension of the trifluoroacetic acid salt of 4-amino-piperidine-1-carboxylic acid (7-methoxy-thiazolo[5,4-d]pyrimidin-2-yl)-amide (1.82 g, 4.30 mmol) in methanol was treated with N,N-diisopropylethylamine (1.5 mL, 6.50 mmol), 4-fluoro-3-(trifluoromethyl)benzaldehyde (1.3 mL, 6.50 mmol) and toluene. The resulting mixture was stirred at 25° C. for 1 h and was then concentrated in vacuo. This procedure was repeated until the reaction mixture became homogenous when dissolved in toluene. After the final concentration to remove toluene, the reaction mixture was diluted with dichloroethane (100 mL) and then was treated with acetic acid (0.26 g) and sodium triacetoxyborohydride (2.73 g, 13 mmol). The resulting reaction mixture was allowed to stir at 25° C. overnight. At this time, the reaction mixture was poured into water and extracted into ethyl acetate. The organics were washed with a saturated aqueous sodium bicarbonate solution, dried over sodium sulfate, filtered and concentrated in vacuo. Flash chromatography (Merck Silica gel 60, 230-400 mesh, gradient elution 1:1 ethyl acetate/hexanes) afforded a colorless oil. The oil was dissolved in diethyl ether and then was concentrated in vacuo to afford 4-(4-fluoro-3-trifluoromethyl-benzylamino)-piperidine-1-carboxylic acid (7-methoxy-thiazolo[5,4-d]pyrimidin-2-yl)-amide (530 mg, 25%) as a white, foamy solid; ES-HRMS m/e calcd for $C_{20}H_{20}F_4N_6O_2S$ (M+H)$^+$ 485.1378, found 485.1378.

In an analogous manner, the compound of Example 84 was obtained as follows:

EXAMPLE 84

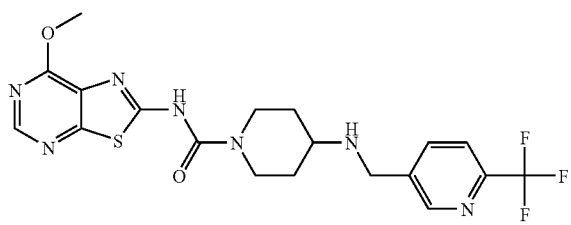

From the trifluoroacetic acid salt of 4-amino-piperidine-1-carboxylic acid (7-methoxy-thiazolo[5,4-d]pyrimidin-2-yl)-amide and 6-trifluoromethyl-pyridine-3-carbaldehyde: 4-[(6-Trifluoromethyl-pyridin-3-ylmethyl)-amino]-piperidine-1-carboxylic acid (7-methoxy-thiazolo[5,4-d]pyrimidin-2-yl)-amide (72 mg, 31.4%) as white solid; ES-HRMS m/e calcd for $C_{19}H_{20}F_3N_7O_2S$ (M+H)$^+$ 468.1424, found 468.1424.

EXAMPLE 85

Synthesis of 4-(4-Fluoro-3-trifluoromethyl-benzoylamino)-piperidine-1-carboxylic acid (7-methoxy-thiazolo[5,4-d]pyrimidin-2-yl)-amide

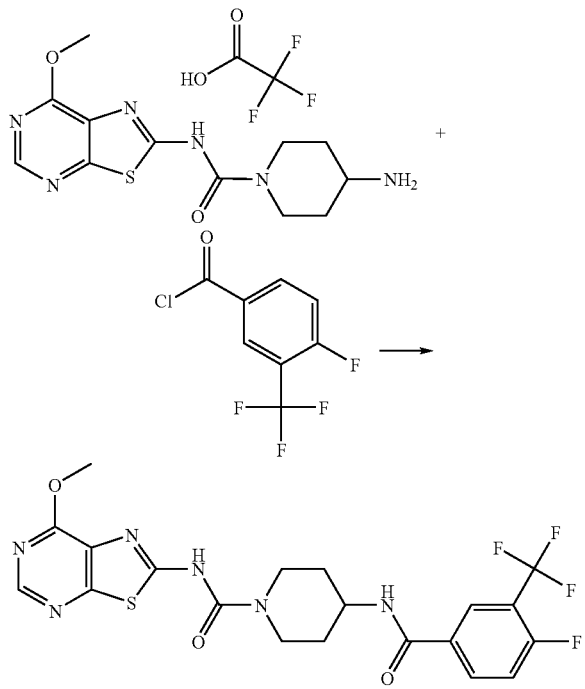

A suspension of the trifluoroacetic acid salt of 4-amino-piperidine-1-carboxylic acid (7-methoxy-thiazolo[5,4-d]pyrimidin-2-yl)-amide (prepared as in Example 83, 580 mg, 1.37 mmol), 4-fluoro-3-trifluoromethyl-benzoyl chloride (261 mL, 1.64 mmol) and triethylamine (573 µL, 4.11 mmol) in methylene chloride (15 mL) was stirred at 25° C. overnight. At this time, the reaction was diluted with water and was extracted with ethyl acetate. The organics were washed with a saturated aqueous sodium chloride solution and a saturated aqueous sodium bicarbonate solution, dried over sodium sulfate, filtered and concentrated in vacuo. Flash chromatography (Merck Silica gel 60, 230-400 mesh, gradient elution 3:7 ethyl acetate/hexanes to 100% ethyl acetate) afforded 4-(4-fluoro-3-trifluoromethyl-benzoylamino)-piperidine-1-carboxylic acid (7-methoxy-thiazolo[5,4-d]pyrimidin-2-yl)-amide (21 mg, 30.6%) as an off-white solid; ES-HRMS m/e calcd for $C_{20}H_{18}F_4N_6O_3S$ (M+H)$^+$ 499.1170, found 499.1170.

EXAMPLE 86

Synthesis of 3-[2-(3-Trifluoromethyl-phenoxy)-ethylamino]-pyrrolidine-1-carboxylic acid (7-methoxy-thiazolo[5,4-d]pyrimidin-2-yl)-amide

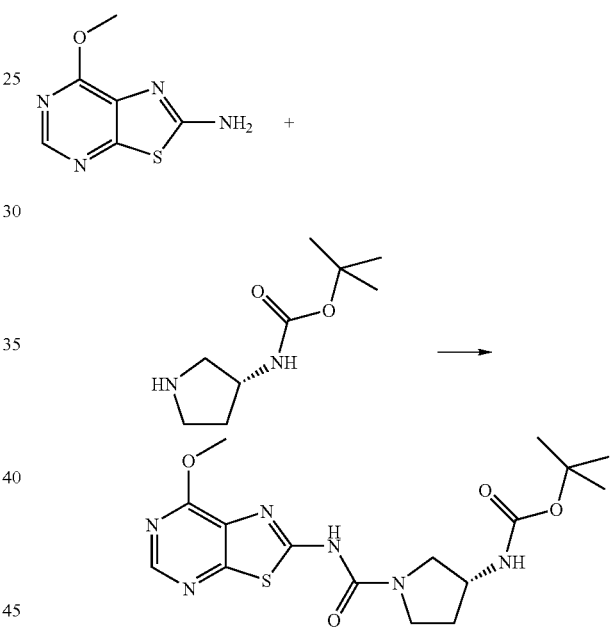

Step 1: A mixture of 7-methoxy-thiazole[5,4-d]pyrimidin-2-ylamine (1.0 g, 5.50 mmol) in tetrahydrofuran (1 L) was treated with pyridine (1.3 g, 16.48 mmol). The reaction was stirred at 25° C. for 30 min. At this time, the reaction was treated slowly with a solution of triphosgene (880 mg, 2.96 mmol) in tetrahydrofuran (5 mL) followed by (3R)-(+)-3-(tert-butoxycarbonyl)amino pyrrolidine (1.74 g, 9.34 mmol). The mixture was allowed to stir at 25° C. overnight. At this time, the reaction was quenched by the addition of a 1N aqueous hydrochloric acid solution. The aqueous layer was extracted with ethyl acetate. The organics were washed with a 2N aqueous hydrochloric acid solution and a saturated aqueous sodium chloride solution, dried over magnesium sulfate, filtered and concentrated in vacuo to afford [1-(7-methoxy-thiazolo[5,4-d]pyrimidin-2-ylcarbamoyl)-pyrrolidin-3-yl]carbamic acid tert-butyl ester (1.75 g, 81%) as a beige solid; LRMS for $C_{16}H_{22}N_6O_4S$ (M+H)$^+$ at m/z=394. The NMR spectrum obtained on the sample is compatible with its structure.

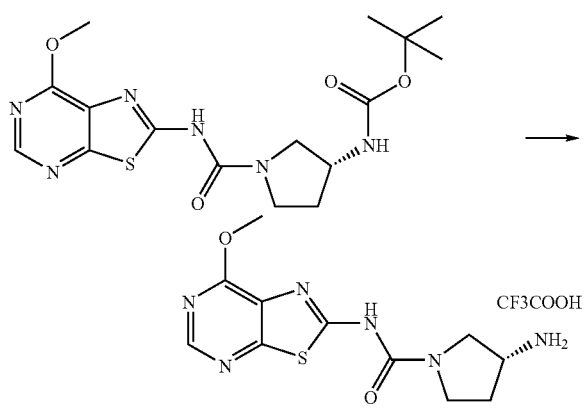

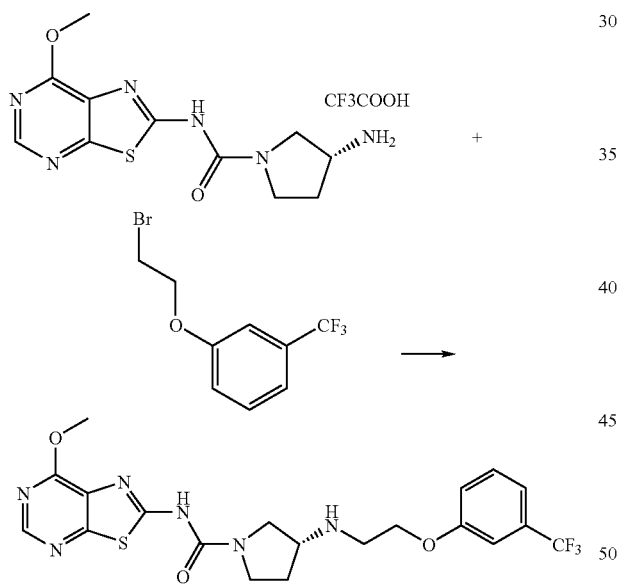

Step 2: A mixture of [1-(7-methoxy-thiazolo[5,4-d]pyrimidin-2-ylcarbamoyl)-pyrrolidin-3-yl]carbamic acid tert-butyl ester (3.4 g, 8.63 mmol) in trifluoroacetic acid (25 mL) was stirred at 25° C. for 1 h. At this time, the reaction was concentrated in vacuo to give a red oil. The oil was triturated with ether to afford the trifluoroacetic acid salt of (S)-3-amino-pyrrolidine-1-carboxylic acid (7-methoxy-thiazolo[5,4-d]pyrimidin-2-yl)-amide (3.5 g, 99%) as a light brown solid.

Step 3: A mixture of (S)-3-amino-pyrrolidine-1-carboxylic acid (7-methoxy-thiazolo[5,4-d]pyrimidin-2-yl)-amide (300 mg, 0.74 mmol) in N,N-dimethylformamide (5 mL) was treated with N,N-diisopropylethylamine (285 mg, 2.20 mmol) and 1-(2-bromoethoxy)-3-(trifluoromethyl) benzene (220 mg, 0.81 mmol). The reaction mixture was allowed to stir at 80° C. for 1 h. At this time, the reaction was poured into water. The aqueous layer was extracted with ethyl acetate. The organics were washed with a saturated aqueous sodium chloride solution, dried over magnesium sulfate, filtered and concentrated in vacuo. Preparative high pressure liquid chromatography afforded 3-[2-(3-trifluoromethyl-phenoxy)-ethylamino]-pyrrolidine-1-carboxylic acid (7-methoxy-thiazolo[5,4-d]pyrimidin-2-yl)-amide (28 mg, 8%) as a light brown solid; LRMS for $C_{20}H_{21}F3N_6O_3S$ (M+H)$^+$ at m/z=482. The NMR spectrum obtained on the sample is compatible with its structure.

EXAMPLE 87

Synthesis of (R)-3-(4-Fluoro-3-trifluoromethyl-benzylamino)-pyrrolidine-1-carboxylic acid (7-methoxy-thiazolo[5,4-d]pyrimidin-2-yl)-amide

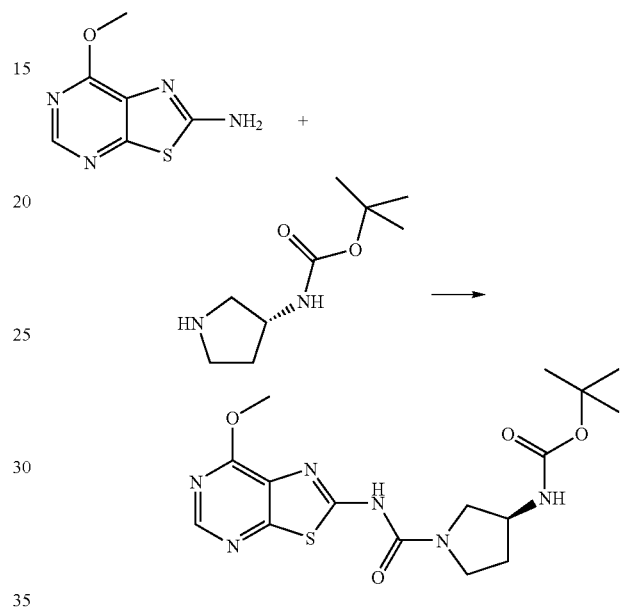

Step 1: A solution of (7-methoxy-thiazolo[5,4-d]pyrimidin-2-yl)-carbamic acid phenyl ester (1.5 g, 0.0049 mol) in acetonitrile (80 mL) at 25° C. was treated with pyrrolidin-3 (R)-yl-carbamic acid tert-butyl ester (0.92 g, 0.049 mol). The reaction mixture was heated at reflux for 1 h. It was then cooled to 25° C. and concentrated in vacuo. The residue was triturated with ether, filtered and dried in vacuo to afford [1-(7-methoxy-thiazolo[5,4-d]pyrimidin-2-ylcarbamoyl)-pyrrolidin-3(R)-yl]-carbamic acid tert-butyl ester (1.99 g, 99%); LRMS for $C_{16}H_{22}N_6O_4S$ (M+H) at m/z 395.

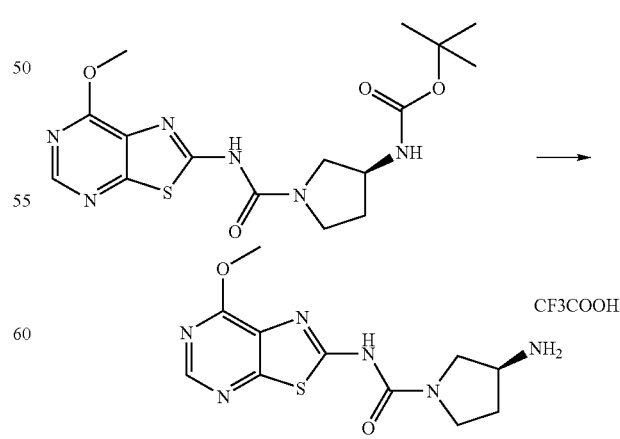

Step 2: A mixture of [1-(7-methoxy-thiazolo[5,4-d]pyrimidin-2-ylcarbamoyl)-pyrrolidin-3(R)-yl]-carbamic acid tert-butyl ester (11.7 g, 0.029 mol) and trifluoroacetic acid (50 mL) was stirred at 25° C. for 2 h. The reaction was concentrated then in vacuo. The resulting residue was triturated with ether and dried in vacuo to afford the trifluoroacetic acid salt of 3-amino-pyrrolidine-1-carboxylic acid (7-methoxy-thiazolo[5,4-d]pyrimidin-2-yl)-amide (14.5 g, 94.1%) as an off-white solid.

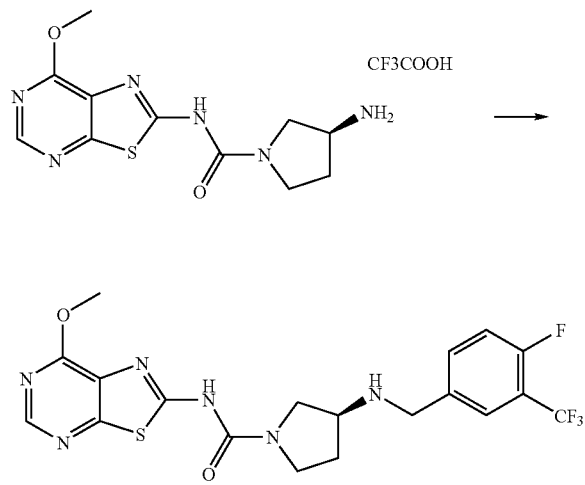

Step 3: A suspension of the trifluoroacetic acid salt of 3-amino-pyrrolidine-1-carboxylic acid (7-methoxy-thiazolo[5,4-d]pyrimidin-2-yl)-amide (2.35 g, 5.8 mmol) in methanol (50 mL) was treated with N,N-diisopropylethylamine (1.5 mL, 8.6 mmol). The resulting mixture was stirred at 25° C. for 30 min. At this time, the reaction was treated with 4-fluoro-3-(trifluoromethyl)benzaldehyde (1.34 g, 6.96 mmol) followed by toluene (50 mL). The resulting mixture was stirred at 60° C. for 1 h and then concentrated in vacuo. Additional toluene (200 mL) was then added. The reaction mixture was stirred for 15 min and then concentrated in vacuo. This procedure was repeated a few times until the reaction mixture became homogenous when dissolved in toluene. After the final concentration to remove toluene, the reaction mixture was diluted with dichloroethane (100 mL) and then treated with acetic acid (351 mg, 5.8 mmol) and sodium triacetoxyborohydride (3.7 g, 17.4 mmol). The resulting reaction mixture was allowed to stir at 25° C. overnight. The reaction mixture was poured into water and extracted with ethyl acetate. The combined organics were washed with water, a saturated aqueous sodium bicarbonate solution and a saturated aqueous sodium chloride solution, dried over sodium sulfate, filtered and concentrated in vacuo. Flash chromatography (Merck Silica gel 60, 230-400 mesh, gradient elution 1:1 ethyl acetate/hexanes to 100% ethyl acetate) afforded (R)-3-(4-fluoro-3-trifluoromethyl-benzylamino)-pyrrolidine-1-carboxylic acid (7-methoxy-thiazolo[5,4-d]pyrimidin-2-yl)-amide (1.44 g, 52.8%) as a foamy solid; ES-HRMS m/e calcd for $C_{19}H_{18}F_4N_6O_2S$ (M+H)$^+$ 471.1221, found 471.1221.

In an analogous manner, the compounds of Examples 88-89 were obtained as follows:

EXAMPLE 88

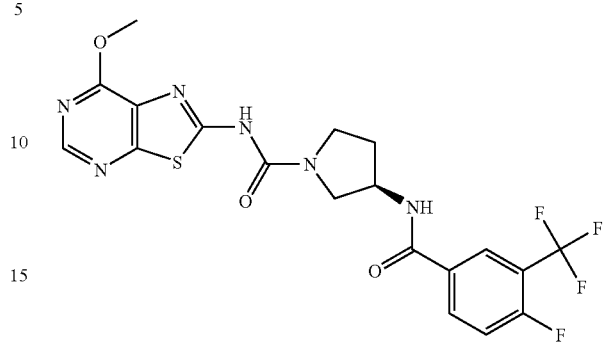

From the trifluoroacetic acid salt of 3-amino-pyrrolidine-1-carboxylic acid (7-methoxy-thiazolo[5,4-d]pyrimidin-2-yl)-amide and (4-fluoro-3-trifluoromethyl-benzoyl chloride: (R)-3-(4-fluoro-3-trifluoromethyl-benzoylamino)-pyrrolidine-1-carboxylic acid (7-methoxy-thiazolo[5,4-d]pyrimidin-2-yl)-amide (72 mg, 31.4%) as white solid (48 mg, 39%); ES-HRMS m/e calcd for $C_{19}H_{16}F_4N_6O_3S$ (M+H)$^+$ 507.0833, found 507.0837.

EXAMPLE 89

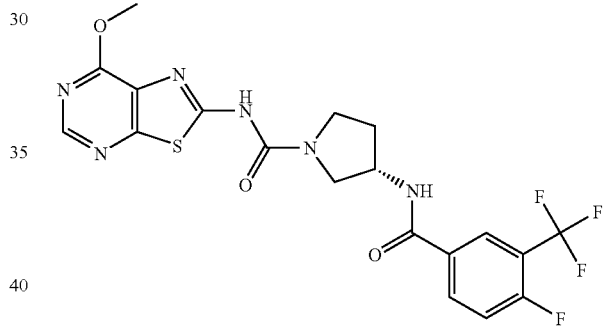

From the trifluoroacetic acid salt of (S)-3-amino-pyrrolidine-1-carboxylic acid (7-methoxy-thiazolo[5,4-d]pyrimidin-2-yl)-amide (as prepared in Example 86) and 4-fluoro-3-trifluoromethyl-benzoyl chloride: (S)-3-(4-fluoro-3-trifluoromethyl-benzoylamino)-pyrrolidine-1-carboxylic acid (7-methoxy-thiazolo[5,4-d]pyrimidin-2-yl)-amide as white solid (18 mg, 10%); ES-HRMS m/e calcd for $C_{19}H_{16}F_4N_6O_3S$ (M+H)$^+$ 485.1014, found 485.1016.

EXAMPLE 90

Synthesis of 4-Fluoro-N-{2-[3-(7-methoxy-thiazolo[5,4-d]pyrimidin-2-yl)-ureido]-ethyl}-3-trifluoromethyl-benzamide

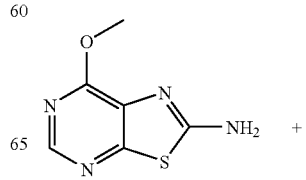

-continued

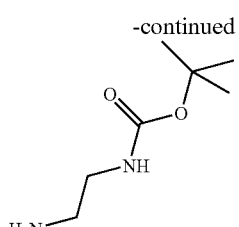

A solution of 7-methoxy-thiazolo[5,4-d]pyrimidin-2-ylamine (233 mg, 1.28 mmol) and pyridine (310 µL, 3.53 mmol) in tetrahydrofuran (6 mL) at 25° C. was treated with a solution of triphosgene (190 mg, 0.64 mmol) in tetrahydrofuran (2 mL) followed by (2-tert-butoxycarbonylamino-ethyl)-carbamic acid (225 mg, 1.40 mmol). The reaction was stirred at 25° C. overnight. At this time, the reaction was treated with a 1N aqueous hydrochloric acid solution and was stirred at 25° C. for an additional 30 min. At this time, the resulting precipitate was collected by filtration and was washed with a 1N aqueous hydrochloric acid solution and diethyl ether to afford {2-[3-(7-methoxy-thiazolo[5,4-d]pyrimidin-2-yl)-ureido]-ethyl}-carbamic acid tert-butyl ester (170 mg, 36.8%) as a pink solid; LRMS for $C_{14}H_{20}N_6O_4S$ (M+H)$^+$ at m/z=369.

A solution of {2-[3-(7-methoxy-thiazolo[5,4-d]pyrimidin-2-yl)-ureido]-ethyl}-carbamic acid tert-butyl ester (170 mg, 0.46 mmol) was treated with trifluoroacetic acid (80 µL, 0.57 mmol). The reaction was stirred at 25° C. for 1 h. The reaction was then concentrated in vacuo, triturated with diethyl ether, collected by filtration and dried in vacuo. A portion of the resulting trifluoroacetic acid salt of 3-amino-pyrrolidine-1-carboxylic acid (7-methoxy-thiazolo[5,4-d]pyrimidin-2-yl)-amide (88 mg, 0.23 mmol) in methylene chloride at 25° C. was treated with 4-fluoro-3-(trifluoromethyl)benzoyl chloride (70 mL, 0.46 mmol). The resulting solution was stirred at 25° C. overnight. Flash chromatography (Merck Silica gel 60, 230-400 mesh, gradient elution 3:1 ethyl acetate/hexanes to 100% ethyl acetate) afforded 4-fluoro-N-{2-[3-(7-methoxy-thiazolo[5,4-d]pyrimidin-2-yl)-ureido]-ethyl}-3-trifluoromethyl-benzamide (25 mg, 11.8%) as a white solid; ES-HRMS m/e calcd for $C_{17}H_{14}F_4N_6O_3S$ (M+H)$^+$ 459.0857, found 459.0862.

EXAMPLE 91

Synthesis of 1-[2-(4-Fluoro-3-trifluoromethyl-benzylamino)-ethyl]-3-(7-methoxy-thiazolo[5,4-d]pyrimidin-2-yl)-urea

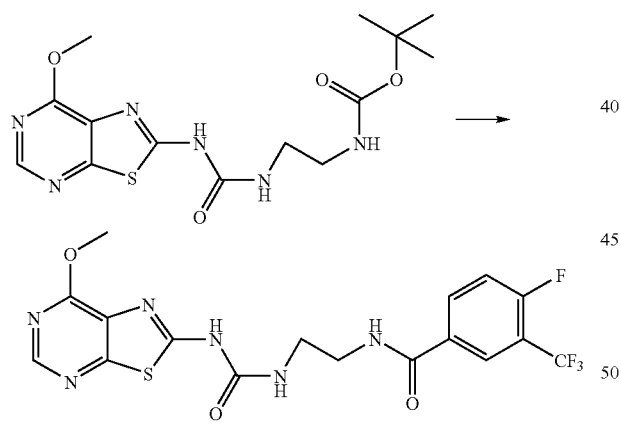

A solution of the trifluoroacetic acid salt of 3-amino-pyrrolidine-1-carboxylic acid (7-methoxy-thiazolo[5,4-d]pyrimidin-2-yl)-amide (176 mg, 0.46 mmol) in methanol (6 ml), 4-fluoro-3-(trifluoromethyl) benzaldehyde (90 mg, 0.46 mmol) and sodium triacetoxyborohydride (293 mg, 1.38 mmol) at 25° C. The resulting solution was stirred at 25° C. overnight. At this time, the reaction mixture was treated with triethylamine (200 mL, 1.44 mmol) and then was stirred for an additional 24 h. At this time, the reaction was concentrated in vacuo. Flash chromatography (Merck Silica gel 60, 230-400 mesh, gradient elution 95/5 methylene chloride/methanol) afforded 1-[2-(4-fluoro-3-trifluoromethyl-benzylamino)-ethyl]-3-(7-methoxy-thiazolo[5,4-d]pyrimidin-2-yl)-urea (37 mg, 18%); ES-HRMS m/e calcd for $C_{17}H_{16}F_4N_6O_2S$ (M+H)$^+$ 445.1065, found 445.1065.

EXAMPLE 92

Synthesis of 3-(7-Methoxy-thiazolo[5,4-d]pyrimidin-2-yl)-1-methyl-1-[2-(3-trifluoromethyl-phenoxy)-ethyl]urea

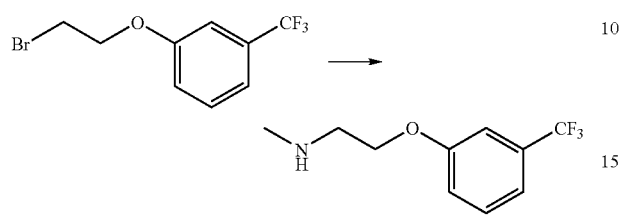

Step 1: A mixture of methylamine hydrochloride salt (380 mg, 5.57 mmol) in tetrahydrofuran (10 mL) was treated with N,N-diisopropylethylamine (1.44 g, 11.15 mmol) and 3-(2-bromoethoxy)benzotrifluoride (300 mg, 1.11 mmol). The reaction mixture was allowed to stir at reflux for 2 d. At this time, the reaction was quenched by the addition of water. The aqueous layer was extracted with ethyl acetate. The organics were washed with a saturated aqueous sodium chloride solution, dried over magnesium sulfate, filtered and concentrated in vacuo. Flash chromatography (Merck Silica gel 60, 230-400 mesh, 95/5 methylene chloride/methanol) afforded methyl-[2-(3-trifluoromethyl-phenoxy)-ethyl]-amine (110 mg, 45%) as yellow solid. The NMR spectrum obtained on the sample is compatible with its structure.

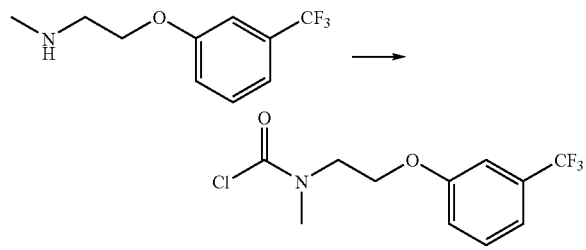

Step 2: A mixture of triphosgene (750 mg, 2.51 mmol) in methylene chloride (10 mL) under a nitrogen atmosphere at 25° C. was slowly treated with pyridine (400 mg, 5.00 mol) followed by the slow addition of a solution of methyl-[2-(3-trifluoromethyl-phenoxy)-ethyl]amine (110 mg, 0.50 mmol.) in methylene chloride (2 mL) via addition funnel. The reaction mixture was stirred at 25° C. overnight. At this time, the reaction was washed with a 1N aqueous hydrochloric acid solution and a saturated aqueous sodium chloride solution, dried over magnesium sulfate, filtered, and concentrated in vacuo to afford methyl-[2-(3-trifluoromethyl-phenoxy)-ethyl]amine-1-carbonyl chloride (0.90 g, 64%) as a golden yellow oil.

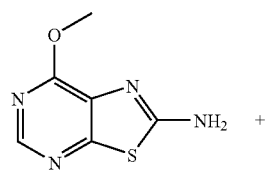

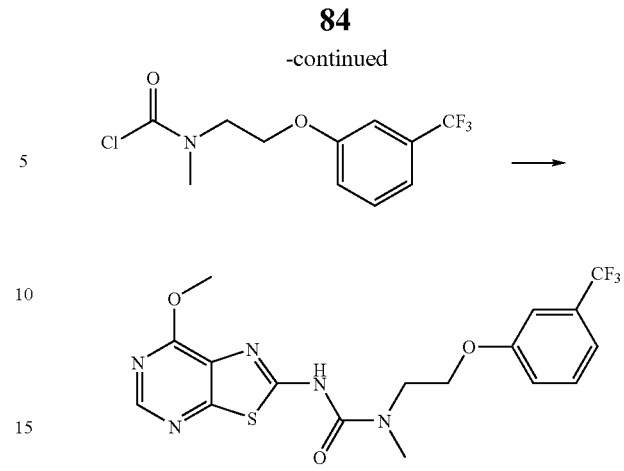

Step 3: A mixture of 7-methoxy-thiazole[5,4-d]pyrimidin-2-ylamine (60 mg, 0.30 mmol) in tetrahydrofuran (6 mL) under a nitrogen atmosphere at 25° C. was treated with sodium hydride (20 mg, 0.40 mmol). The reaction mixture was stirred at 65° C. for 30 min. At this time, the reaction was treated with N,N-diisopropylethylamine (130 mg, 1.00 mmol) and methyl-[2-(3-trifluoromethyl-phenoxy)-ethyl]amine-1-carbonyl chloride (90 mg, 0.32 mmol). The mixture was stirred at 65° C. overnight. At this time, the reaction was concentrated in vacuo, diluted with water and extracted with ethyl acetate. The organics were washed with a 2N aqueous hydrochloric acid solution and a saturated aqueous sodium chloride solution, dried over magnesium sulfate, filtered, and concentrated in vacuo. Flash chromatography (Merck Silica gel 60, 230-400 mesh, 95/5 methylene chloride/methanol) afforded 3-(7-methoxy-thiazolo[5,4-d]pyrimidin-2-yl)-1-methyl-1-[2-(3-trifluoromethyl-phenoxy)-ethyl]urea (40 mg, 28%) as a light brown solid; LRMS for $C_{17}H_{16}F_3N_5O_3S$ $(M+H)^+$ at m/z=427. The NMR spectrum obtained on the sample is compatible with its structure.

EXAMPLE 93

Synthesis of 4-Hydroxy-4-[3-(trifluoromethy)phenyl]piperidine-1-carboxylic acid (7-methoxy-thiazolo[5,4-b]pyridine-2-yl)-amide

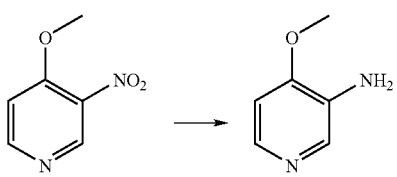

Step 1: To a mixture of 4-Methoxy-3-nitropyridine (5.0 g, 32.44 mmole) in ethanol (100 mL) was added 10% palladium on carbon catalyst (200 mg). The resulting mixture was allowed to shake under a hydrogen atmosphere (50 psi) for 6 h. at room temperature. TLC (50% ethyl acetate/hexane) indicated complete consumption of starting material. Filtration through celite to remove the catalyst and concentration gave 3-Amino-4 methoxypyridine (4.0 g, 32.44 mmol, 100% yield) as dark red oil.

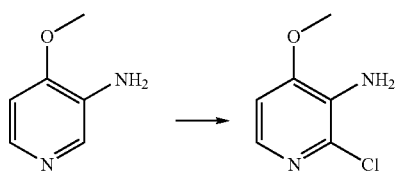

Step 2: To a magnetically stirred mixture of 3-Amino-4-methoxypyridine (4.45 g, 35.89 mmole) in 12N HCl (25 mL) cooled in an ice bath was added hydrogen peroxide (5.3 g, 46.65 mmol, 30% solution). The reaction was allowed to slowly warm to room temperature and stirred for 1 h. TLC (50% ethyl acetate/hexane) indicated complete consumption of starting material. The reaction mixture was slowly poured into saturated sodium bicarbonate solution (400 mL) to neutralize the reaction and extracted with ethyl acetate. The resulting organic layers were washed with saturated sodium chloride solution and dried over magnesium sulfate. Filtration and concentration gave 3-Amino-2-chloro-4 methoxypyridine (4.56 g, 28.77 mmol, 80% yield) as an orange solid.

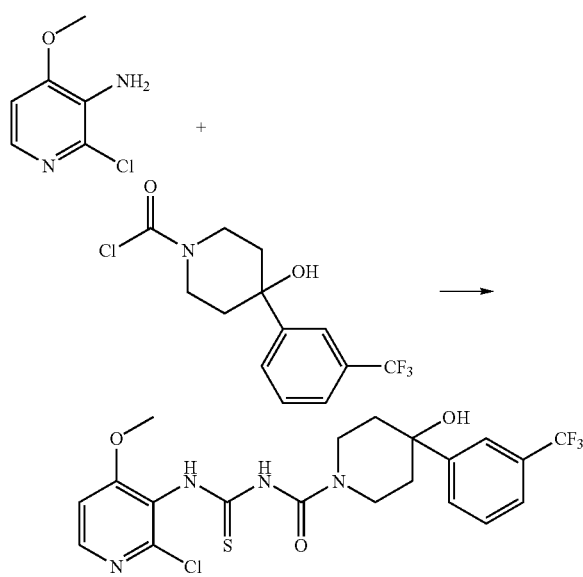

Step 3: To a magnetically stirred mixture of 4-Hydroxy-4-[3-(trifluoromethyl)phenyl]piperidine-1-carbonyl chloride (465 mg, 1.51 mmol) in acetone (15 mL) was added ammonium thiocyanate (105 mg, 1.39 mmole). The reaction is stirred at reflux for 30 min. 3-Amino-2-chloro-4 methoxypyridine (200 mg, 1.26 mmole) was added and the reaction was allowed to continue to stir at reflux overnight. TLC (50% ethyl acetate/hexane) indicated complete consumption of starting material. The reaction was poured into water and the aqueous layer was extracted with ethyl acetate. The resulting organic layers were washed with 2N HCl (2×) and saturated sodium chloride solution and then dried over magnesium sulfate. Purification by flash chromatography gave 1-(2-Chloro-4-methoxy-pyridin-3-yl)-3-[4-hydroxy-4-(3-trifluoromethylphenyl)-piperidine-1-carbonyl]-thiourea (100 mg, 0.20 mmole, 16% yield) as a light yellow solid. (LRMS for $C_{20}H_{20}ClF_3N_4O_3S$ (M+H)$^+$ at m/z=488. The NMR spectrum obtained on the sample is compatible with its structure.

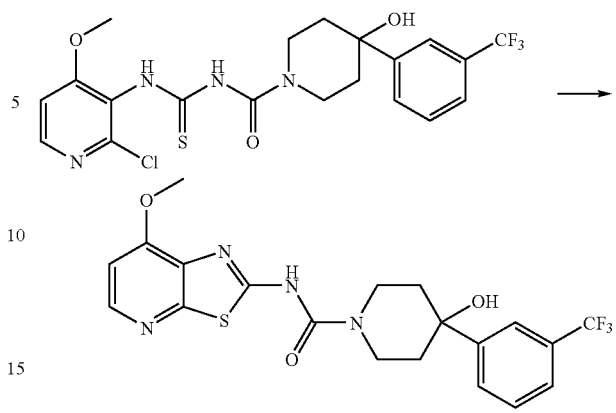

Step 4: To a magnetically stirred mixture of 1-(2-Chloro-4-methoxy-pyridin-3-yl)-3-[4-hydroxy-4-(3-trifluoromethylphenyl)-piperidine-1-carbonyl]-thiourea (100 mg, 0.20 mmol) in THF (10 mL) was added sodium hydride (10 mg, 0.25 mmole, 60% dispersion in mineral oil). The reaction is stirred at reflux overnight. TLC (80% ethyl acetate/hexane) indicated complete consumption of starting material. The reaction was poured into water and the aqueous layer was extracted with ethyl acetate. The resulting organic layers were washed with 2N HCl (2×) and saturated sodium chloride solution and then dried over magnesium sulfate. Purification by flash chromatography gave 4-Hydroxy-4-[3-(trifluoromethy)phenyl]piperidine-1-carboxylic acid (7-methoxy-thiazolo[5,4-b]pyridine-2-yl)-amide (20 mg, 0.04 mmole, 22% yield) as a light yellow solid. (LRMS for $C_{20}H_{19}F_3N_4O_3S$ (M+H)$^+$ at m/z=452.

EXAMPLE 94

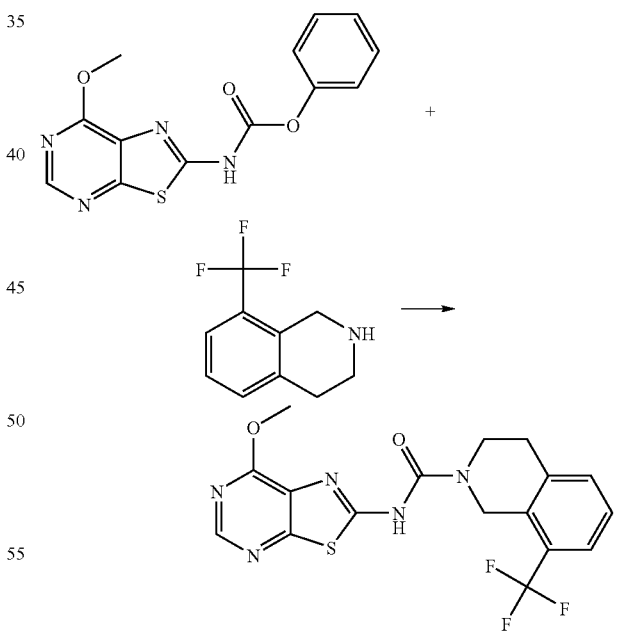

A mixture of 8-Trifluoro-1,2,3,4-tetrahydro-isoquinoline (30 mg, 0.15 mmol, RO4993861-000) in acetonitrile (5 mL) was treated with (7-methoxy-thiazolo[5,4-d]pyrimidin-2-yl)-carbamic acid phenyl ester (45 mg, 0.15 mmol). The mixture was stirred at reflux for 2 h. At this time, the reaction was poured into a saturated aqueous sodium bicarbonate solution. The aqueous layer was extracted with ethyl acetate. The organics were washed with a saturated aqueous sodium chloride solution, dried over magnesium sulfate, filtered, and concentrated in vacuo. Flash chromatography (Merck Silica gel 60, 230-400 mesh, 98/2 methylene chloride/ methanol) afforded 8-Trifluoromethyl-3,4-dihydro-1H-isoquinoline-2-carboxylic acid (7-methoxy-thiazolo[5,4-d]pyrimidin-2-yl)-amide (23 mg, 38%) as a light brown solid. LRMS for $C_{17}H_{14}F_3N_5O_2S$ (M+H)$^+$ at m/z=409. The NMR spectrum obtained on the sample is compatible with its structure.

EXAMPLE 95

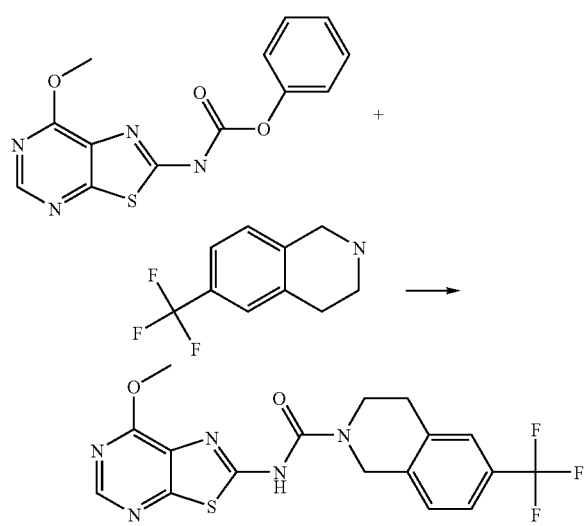

A mixture of 6-Trifluoro-1,2,3,4-tetrahydro-isoquinoline (50 mg, 0.25 mmol) in acetonitrile (10 mL) was treated with (7-methoxy-thiazolo[5,4-d]pyrimidin-2-yl)-carbamic acid phenyl ester 745 mg, 0.25 mmol). The mixture was stirred at reflux for 2 h. At this time, the reaction was poured into a saturated aqueous sodium bicarbonate solution. The aqueous layer was extracted with ethyl acetate. The organics were washed with a saturated aqueous sodium chloride solution, dried over magnesium sulfate, filtered, and concentrated in vacuo. Flash chromatography (Merck Silica gel 60, 230-400 mesh, 98/2 methylene chloride/methanol) afforded 6-Trifluoromethyl-3,4-dihydro-1H-isoquinoline-2-carboxylic acid (7-methoxy-thiazolo[5,4-d]pyrimidin-2-yl)-amide (15 mg, 15%) as a white solid. LRMS for $C_{17}H_{14}F_3N_5O_2S$ (M+H)$^+$ at m/z=409. The NMR spectrum obtained on the sample is compatible with its structure.

EXAMPLE 96

Synthesis of (3-Chloro-phenyl)-[4-(7-methoxy-thiazolo[5,4-d]pyrimidin-2-ylcarbamoyl)-piperazin-1-yl]-acetic acid methyl ester

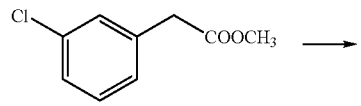

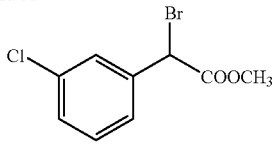

Step 1: A mixture of (3-Chloro-phenyl)-acetic acid methyl ester (2.0 g, 10.8 mmol), N-bromosuccinimide (1.95 g, 11.0 mmol) and 3 drops of hydrobromic acid (48% solution) in chloroform (100 mL) was heated under reflux for three days. Additional amounts of N-bromosuccinimide and hydrobromic acid were added to drive the reaction to completion. The reaction mixture was concentrated to dryness, taken up in methylene chloride and loaded onto a column of silica gel. Elution with 10% ethyl acetate/hexanes gave Bromo-(3-chloro-phenyl)-acetic acid methyl ester (1.95 g, 69% yield) as a colorless oil. The NMR spectrum obtained on the sample is compatible with its structure.

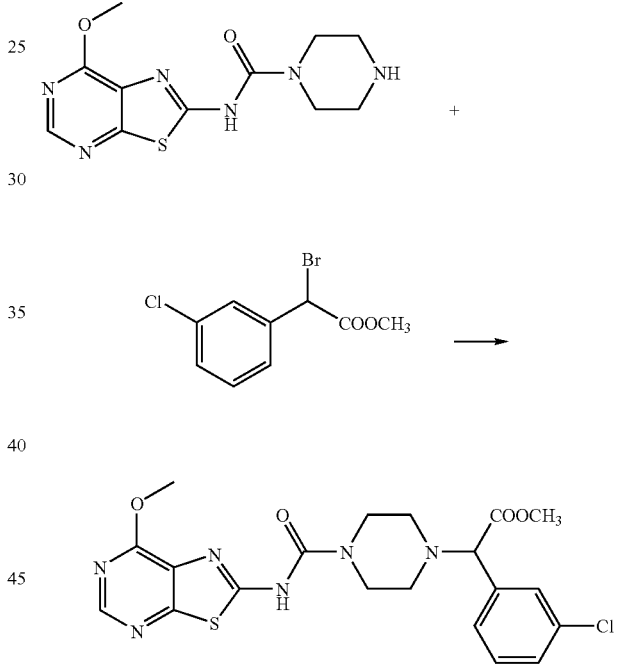

Step 2: A mixture of Piperazine-1-carboxylic acid (7-methoxy-thiazolo[5,4-d]pyrimidin-2-yl)-amide trifluoroacetate salt (1.56 g, 3.82 mmol), diisopropylethylamine (2.7 mL, 15.5 mmol) in N,N-dimethylformamide (15 mL) was stirred at room temperature for 30 minutes. To the mixture was added potassium carbonate (0.8 g, 5.8 mmole) and Bromo-(3-chloro-phenyl)-acetic acid methyl ester (1.0 g, 3.8 mmol) and the resulting mixture was stirred at room temperature overnight. Filtration and concentration gave a solid which was dissolved in methanol and absorbed onto 2 g of silica gel. The silica gel was loaded onto an Isco 120 g column and eluted using 0→5% Methanol/methylene chloride to yield (3-Chloro-phenyl)-[4-(7-methoxy-thiazolo[5,4-d]pyrimidin-2-ylcarbamoyl)-piperazin-1-yl]-acetic acid methyl ester as a white powder; LRMS for $C_{20}H_{21}ClN_6O_4S$ (M+H)$^+$ at m/z=477. The NMR spectrum obtained on the sample is compatible with its structure.

EXAMPLE 97

4-[1-(3-Chloro-phenyl)-2-hydroxy-ethyl]-piperazine-1-carboxylic acid (7-methoxy-thiazolo[5,4-d]pyrimidin-2-yl)-amide

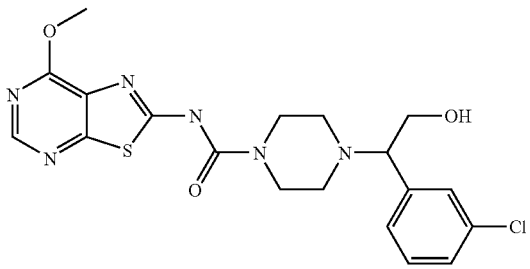

A mixture of (3-Chloro-phenyl)-[4-(7-methoxy-thiazolo[5,4-d]pyrimidin-2-ylcarbamoyl)-piperazin-1-yl]-acetic acid methyl ester (100 mg, 0.21 mmol) in tetrahydrofuran (3 mL) at 0° C. was added lithium aluminum hydride (25 mg, 0.66 mmol). The mixture was warmed up to room temperature and stirred for two hours. LCMS analysis indicated a mixture of starting material and product. The reaction was worked up using Feiser's conditions and the crude obtained was then purified using reversed phase HPLC to give 4-[1-(3-Chloro-phenyl)-2-hydroxy-ethyl]-piperazine-1-carboxylic acid (7-methoxy-thiazolo[5,4-d]pyrimidin-2-yl)-amide as a white powder; LRMS for $C_{19}H_{21}ClN_6O_3S$ (M+H)$^+$ at m/z=449. The NMR spectrum obtained on the sample is compatible with its structure.

EXAMPLE 98

4-[2-Methoxy-1-(3-trifluoromethyl-phenyl)-ethyl]-piperazine-1-carboxylic acid (7-methoxy-thiazolo[5,4-d]pyrimidin-2-yl)-amide

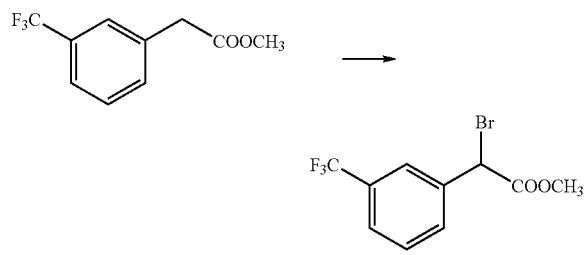

Step 1: A mixture of (3-trifluoromethyl-phenyl)-acetic acid methyl ester (6.0 g, 25.9 mmol) and N-bromosuccinimide (9.2 g, 51.7 mmol) and a few drops of hydrobromic acid (48% solution) in chloroform (250 mL) was heated under reflux for two days. The reaction mixture was concentrated to dryness, taken up in methylene chloride and loaded onto a column of silica gel. Elution with 5% ethyl acetate/hexanes gave Bromo-(3-trifluoromethyl-phenyl)-acetic acid methyl ester (3.0 g, 39% yield) as colorless oil. The NMR spectrum obtained on the sample is compatible with its structure.

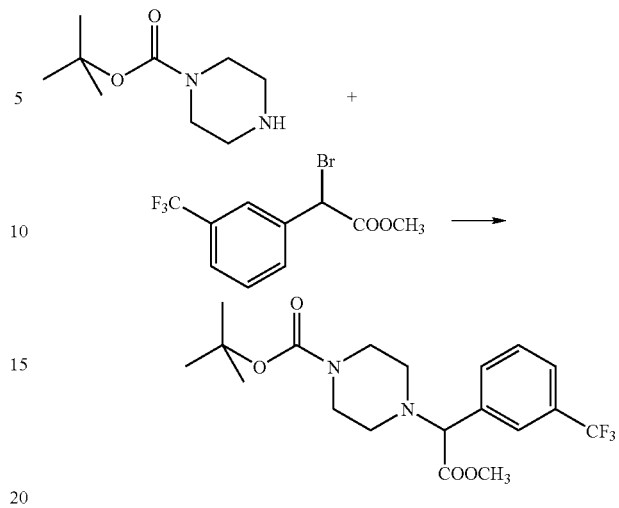

Step 2: A mixture of Piperazine-1-carboxylic acid tert-butyl ester (1.80 g, 9.68 mmol), potassium carbonate (2.0 g, 14.5 mmole) and Bromo-(3-trifluoromethyl-phenyl)-acetic acid methyl ester (3.0 g, 9.65 mmol) in N,N-dimethylformamide (40 mL) was stirred at room temperature overnight. Concentration gave a crude material which was partitioned between methylene chloride and water. The organic layer was dried over magnesium sulfate and concentrated to give an oil. The crude oil was loaded onto an Isco 120 g column and eluted using 20% ethyl acetate/hexanes to yield 4-[Ethoxycarbonyl-(3-trifluoromethyl-phenyl)-methyl]-piperazine-1-carboxylic acid tert-butyl ester (3.0 g, 74% yield) as a colorless oil. The NMR spectrum obtained on the sample is compatible with its structure.

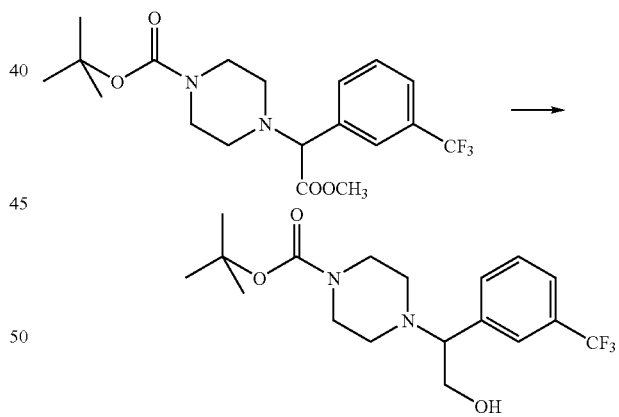

Step 3: A solution of 4-[Ethoxycarbonyl-(3-trifluoromethyl-phenyl)-methyl]-piperazine-1-carboxylic acid tert-butyl ester (2.10 g, 5.05 mmol) in tetrahydrofuran (30 mL) at 0° C. was added lithium aluminum hydride (1M in tetrahydrofuran, 7.57 mL, 7.57 mmol) dropwise. The mixture was stirred at 0° C. for two hours. The excess LAH was quenched with ethyl acetate and the mixture was stirred with sodium sulfate decahydrate for 10 minutes. The slurry was filtered and the filtrate partitioned between ethyl acetate and water. The organic layer was dried with magnesium sulfate. Filtration, concentration gave a crude which was loaded onto a column of silica gel. Elution with 40% ethyl acetate/hexanes gave 4-[2-Hydroxy-1-(3-trifluoromethyl-phenyl)-ethyl]-piperazine-1-carboxylic acid tert-butyl ester (1.4 g, 74% yield) as a colorless oil. The NMR spectrum obtained on the sample is compatible with its structure.

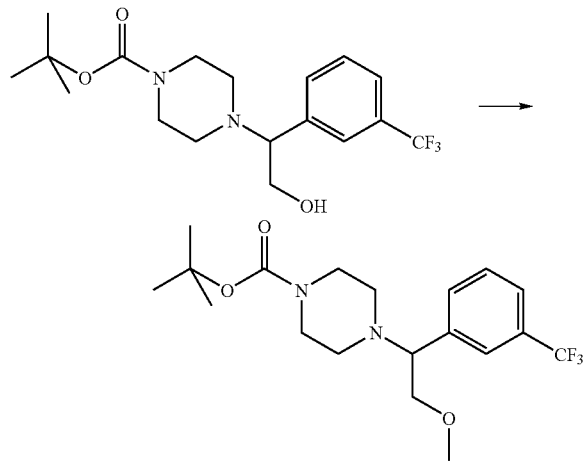

Step 4: A mixture of 4-[2-Hydroxy-1-(3-trifluoromethyl-phenyl)-ethyl]-piperazine-1-carboxylic acid tert-butyl ester (200 mg, 0.53 mmol) in tetrahydrofuran (5 mL) and N,N-dimethylformamide (5 mL) at 0° C. was added sodium hydride (60% in mineral oil, 70 mg, 1.75 mmol) followed by iodomethane (230 mg, 1.62 mmole). The mixture was stirred at 0° C. for three hours. The reaction was quenched with saturated aqueous ammonium chloride solution and partitioned between ethyl acetate and water. The organic layer was dried with magnesium sulfate. Filtration, concentration gave a crude oil which was loaded onto a column of silica gel. Elution with 50% ethyl acetate/hexanes gave 4-[2-Methoxy-1-(3-trifluoromethyl-phenyl)-ethyl]-piperazine-1-carboxylic acid tert-butyl ester (190 mg, 92% yield) as a colorless oil. The NMR spectrum obtained on the sample is compatible with its structure.

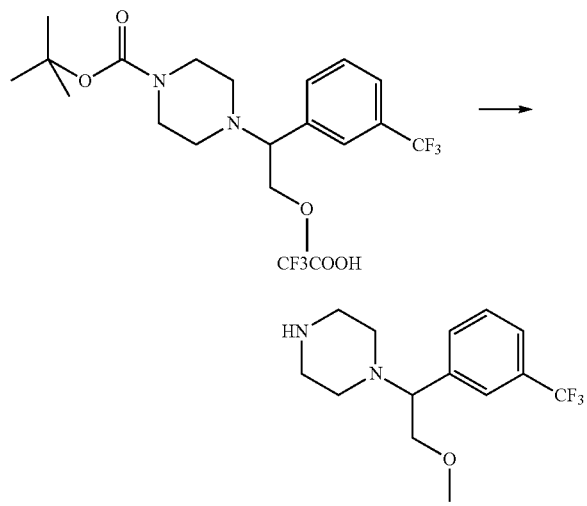

Step 5: A mixture of 4-[2-Methoxy-1-(3-trifluoromethyl-phenyl)-ethyl]-piperazine-1-carboxylic acid tert-butyl ester (150 mg, 0.387 mmoles) in neat trifluoroacetic acid (3 mL) was stirred at room temperature for one hour. The mixture was concentrated to dryness and pumped on high vacuum to give 1-[2-Methoxy-1-(3-trifluoromethyl-phenyl)-ethyl]-piperazine trifluoroacetate as an oil. The material was used in the next step without further purification.

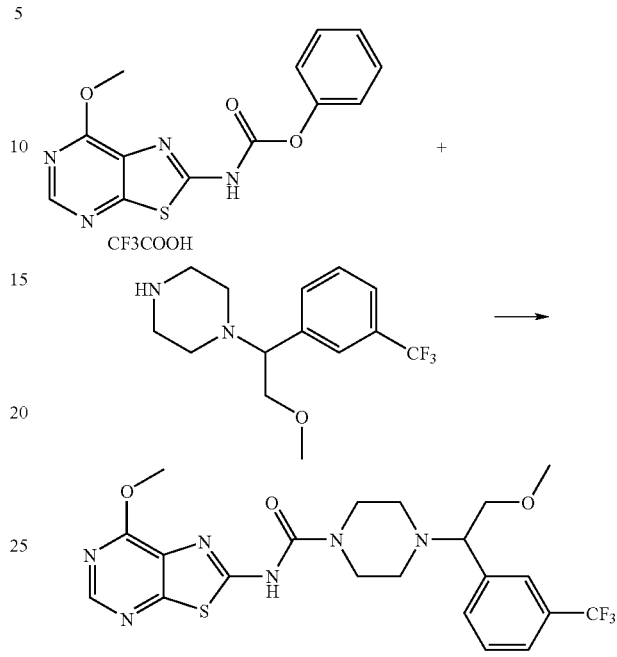

Step 6: A mixture of 1-[2-Methoxy-1-(3-trifluoromethyl-phenyl)-ethyl]-piperazine trifluoroacetate (160 mg, 0.40 mmol) and diisopropylethylamine (0.35 mL, 2.0 mmole) in acetonitrile (10 mL) was heated at 70° C. for ten minutes. After cooling to room temperature, (7-methoxy-thiazolo[5,4-d]pyrimidin-2-yl)-carbamic acid phenyl ester (120 mg, 0.40 mmol) was added to the above solution. The mixture was stirred at reflux for three hours. LCMS analysis indicated complete consumption of starting material. The reaction was concentrated and the crude was purified using reversed phase HPLC to give 4-[2-Methoxy-1-(3-trifluoromethyl-phenyl)-ethyl]-piperazine-1-carboxylic acid (7-methoxy-thiazolo[5,4-d]pyrimidin-2-yl)-amide (81 mg, 41% yield) as a white powder. LRMS for $C_{21}H_{23}F_3N_6O_3S$ $(M+H)^+$ at m/z=497. The NMR spectrum obtained on the sample is compatible with its structure.

EXAMPLE 99

4-hydroxy-4-[3-(trifluoromethy)phenyl]piperidine-1-carboxylic acid (7-methoxy-5-methylsulfanyl-thiazolo[5,4-d]pyrimidin-2-yl)-amide

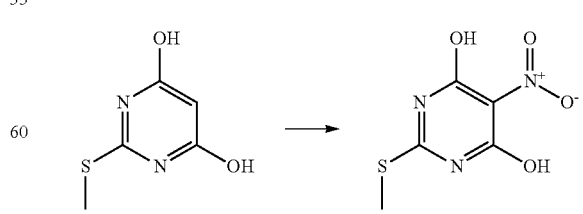

Step1: 4,6-Dihydroxy-2-methylthiopyrimidine (10.0 g, 63.22 mmol) was added over 1 hr to fuming nitric acid (30 mL) at 0° C. The red solution was stirred an additional 1 hr at 0° C. and then poured onto ice to give a light brown solid which was filtered off and washed with water and diethyl ether. The solid was dried under vacuo to give 4,6-Dihydroxy-2-methylthio-5-nitropyrimidine (9.30 g, 72%) as a light brown solid. LRMS for $C_5H_5N_3O_4S$ (M+H)$^+$ at m/z=203. The NMR spectrum obtained on the sample is compatible with its structure.

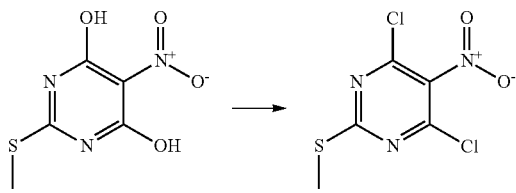

Step 2: A mixture 4,6-Dihydroxy-2-methylthio-5-nitropyrimidine (9.30 g, 45.81 mmol), phosphorus oxychloride (40 mL) and diethylaniline (12 mL) were refluxed for 1 hr. After partial evaporation the liquid was poured onto ice to give a brown solid which was filtered and washed with water. The solid was dried under vacuo to give 4,6-Dichloro-2-methylthio-5-nitropyrimidine (10.5 g, 95%) as a brown solid. LRMS for $C_5H_3Cl_2N_3O_2S$ (M+H)$^+$ at m/z=240. The NMR spectrum obtained on the sample is compatible with its structure.

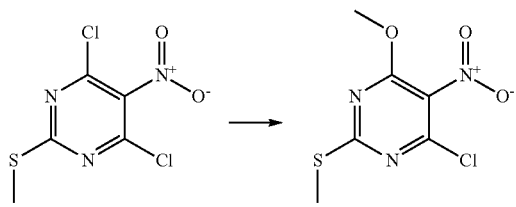

Step 3: A mixture of 4,6-Dichloro-2-methylthio-5-nitropyrimidine (5.25 g, 21.88 mmol) in methanol (40 mL) was treated with sodium methoxide (1.3 g, 24.06 mmol). The mixture was stirred at room temperature for 3 h. At this point the reaction was poured onto ice to give a brown solid which was filtered and washed with water. The solid was dried under vacuo to give 4-Chloro-6-methoxy-2-methylthio-5-nitropyrimidine (4.40 g, 85%) as a brown solid. LRMS for $C_6H_6Cl_1N_3O_3S$ (M+H)$^+$ at m/z=235. The NMR spectrum obtained on the sample is compatible with its structure.

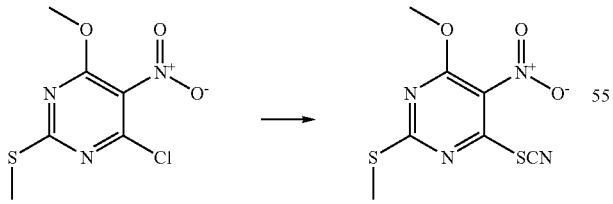

Step 4: A mixture of 4-Chloro-6-methoxy-2-methylthio-5-nitropyrimidine (4.40 g, 18.68 mmol) in acetic acid (30 mL) was treated with ammonium thiocyanate (2.84 g, 37.37 mmol). The mixture was stirred at 85° C. for 6 h. After partial evaporation the liquid was poured onto ice to give a brown solid which was filtered and washed with water. The solid was dried under vacuo to give 4-Methoxy-2-methylthio-5-nitro-6-thicyanato-pyrimidine (2.20 g, 46%) as a brown solid. LRMS for $C_7H_6N_4O_3S_2$ (M+H)$^+$ at m/z=258. The NMR spectrum obtained on the sample is compatible with its structure.

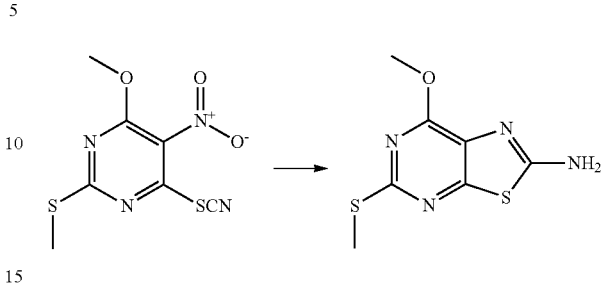

Step 5: A mixture of 4-Methoxy-2-methylthio-5-nitro-6-thicyanato-pyrimidine (2.20 g, 8.53 mmol) in acetic acid (30 mL) was cooled in an ice water bath and iron powder (1.43 g, 25.58 mmol) was added portionwise. After complete addition the mixture was stirred at 60° C. for 4 h. The reaction was then cooled to room temperature, filtered and poured on ice to give a light brown solid which was filtered and washed with water and diethyl ether. The solid was dried under vacuo to give 7-Methoxy-5-methylsulfanyl-thiazolo[5,4-d]pyrimidin-2-ylamine (1.60 g, 82%) as a light brown solid. LRMS for $C_7H_8N_4OS_2$ (M+H)$^+$ at m/z=228. The NMR spectrum obtained on the sample is compatible with its structure.

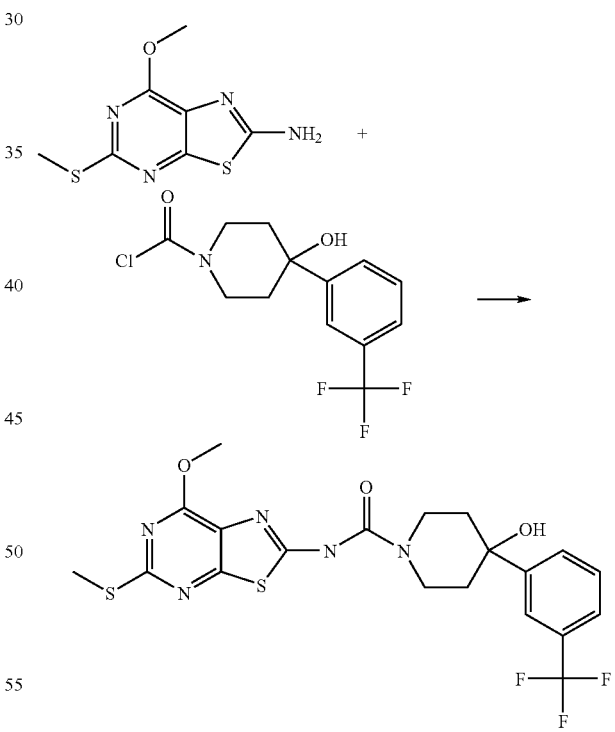

Step 6: A magnetically stirred mixture of 7-Methoxy-5-methylsulfanyl-thiazolo[5,4-d]pyrimidin-2-ylamine (500 mg, 2.19 mmol) in tetrahydrofuran (20 mL) under a nitrogen atmosphere at 25° C. was treated with sodium hydride (60% suspension in mineral oil, 265 mg, 6.58 mmol). The reaction mixture was stirred at 50° C. for 1 h. At this time, the reaction was cooled to room temperature and was treated with N,N-diisopropylethylamine (850 mg, 6.58 mmol) and 4-hydroxy-4-[3-(trifluoromethyl)phenyl]piperidine-1-carbonyl chloride (810 mg, 2.63 mmol). The reaction mixture was stirred at room temperature for 3 d. At this time, the reaction was concentrated in vacuo, poured into water and extracted with ethyl acetate. The organics were washed with a 2N aqueous hydrochloric acid solution and a saturated aqueous sodium chloride solution, dried over magnesium sulfate, filtered and concentrated in vacuo. Flash chromatography (Merck Silica gel 60, 230-400 mesh, 98:2 methylene chloride/methanol) afforded 4-hydroxy-4-[3-(trifluoromethy)phenyl]piperidine-1-carboxylic acid (7-methoxy-5-methylsulfanyl-thiazolo[5,4-d]pyrimidin-2-yl)-amide (375 mg, 34%) as a red solid. LRMS for $C_{20}H_{20}F_3N_5O_3S_2$ (M+H)$^+$ at m/z=499. The NMR spectrum obtained on the sample is compatible with its structure.

EXAMPLE 100

4-hydroxy-4-[3-(trifluoromethy)phenyl]piperidine-1-carboxylic acid (5-hydroxy-7-methoxy-thiazolo[5,4-d]pyrimidin-2-yl)-amide

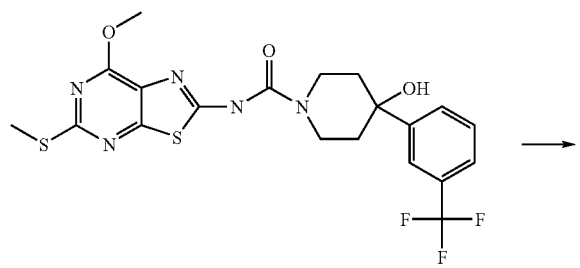

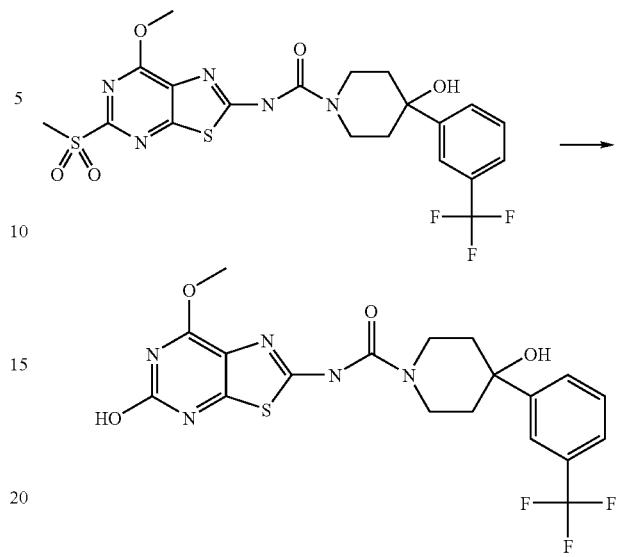

Step 1: A magnetically stirred mixture of 4-hydroxy-4-[3-(trifluoromethy)phenyl]piperidine-1-carboxylic acid (7-methoxy-5-methylsulfanyl-thiazolo[5,4-d]pyrimidin-2-yl)-amide (375 mg, 0.75 mmol) in methanol (20 mL) was cooled in an ice water bath and treated with sodium tungstate dihyrate (135 mg, 0.04 mmol) followed by hydrogen peroxide (30% solution, 10 mL) The reaction mixture was warmed to room temperature and stirred for 2 h. The reaction was then poured into water and extracted with methylene chloride. The organics were washed with saturated aqueous sodium chloride solution, dried over magnesium sulfate, filtered and concentrated in vacuo to afford 4-hydroxy-4-[3-(trifluoromethy)phenyl]piperidine-1-carboxylic acid (5-methanesulfonyl-7-methoxy-thiazolo[5,4-d]pyrimidin-2-yl)-amide (251 mg, 63%) as a red solid. LRMS for $C_{20}H_{20}F_3N_5O_5S_2$ (M+H)$^+$ at m/z=499. The NMR spectrum obtained on the sample is compatible with its structure.

Step 2: A magnetically stirred mixture of 4-hydroxy-4-[3-(trifluoromethy)phenyl]piperidine-1-carboxylic acid (5-methanesulfonyl-7-methoxy-thiazolo[5,4-d]pyrimidin-2-yl)-amide (250 mg, 0.47 mmol) in THF (10 mL) and water (5 mL) was treated with a 2N aqueous KOH solution (0.5 mL, 0.94 mmol). The reaction mixture was stirred at 75° C. for 4 h. The reaction was then cooled to room temperature and poured into water and extracted with methylene chloride. The organics were washed with saturated aqueous sodium chloride solution, dried over magnesium sulfate, filtered and concentrated in vacuo to afford 4-hydroxy-4-[3-(trifluoromethy) phenyl]piperidine-1-carboxylic acid (5-hydroxy-7-methoxy-thiazolo[5,4-d]pyrimidin-2-yl)-amide (32 mg, 15%) as a white solid. LRMS for $C_{19}H_{18}F_3N_5O_4S_2$ (M+H)$^+$ at m/z=469. The NMR spectrum obtained on the sample is compatible with its structure.

EXAMPLE 101

3-(4-Fluoro-3-trifluoromethyl-benzylamino)-pyrrolidine-1-carboxylic acid (7-methoxy-thiazolo[5,4-b]pyridin-2-yl)-amide

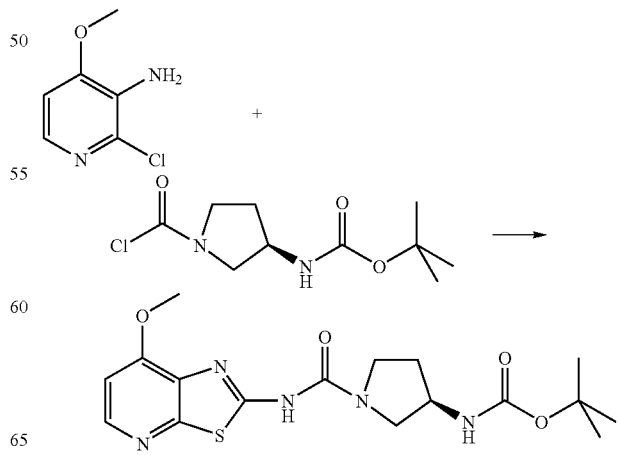

Step 1: A magnetically stirred mixture of (1-Chlorocarbonyl-pyrrolidin-3-yl)carbamic acid tert-butyl ester (820 mg, 3.30 mmol) in acetone (15 mL) under a nitrogen atmosphere at 25 C was treated with ammonium thiocyanate (240 mg, 3.15 mmol). The reaction mixture was stirred at reflux for 30 min. At this time, the reaction was treated with 3-amino-2-chloro-4 methoxypyridine (440 mg, 2.78 mmol). The reaction mixture was refluxed overnight. At this time, the reaction was concentrated in vacuo, poured into water and extracted with ethyl acetate. The organics were washed with a 2N aqueous hydrochloric acid solution and a saturated aqueous sodium chloride solution, dried over magnesium sulfate, filtered and concentrated in vacuo. Flash chromatography (Merck Silica gel 60, 230-400 mesh, 98:2 methylene chloride/methanol) afforded [1-(7-Methoxy-thiazolo[5,4-b]pyridin-2-ylcarbamoyl)-pyrrolidin-3-yl]-carbamic acid tert-butyl ester (160 mg, 15%) as a light yellow solid. LRMS for $C_{17}H_{23}N_5O_4S$ $(M+H)^+$ at m/z=393. The NMR spectrum obtained on the sample is compatible with its structure.

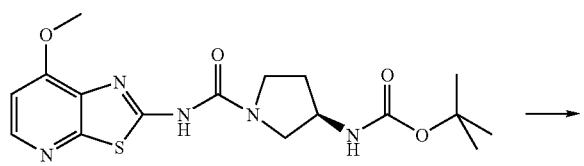

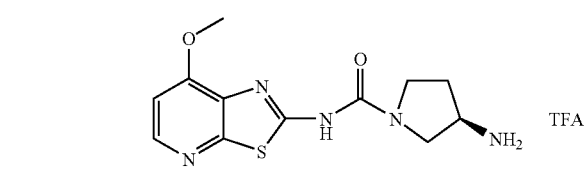

Step 2: A mixture of [1-(7-Methoxy-thiazolo[5,4-b]pyridin-2-ylcarbamoyl)-pyrrolidin-3-yl]-carbamic acid tert-butyl ester (160 mg, 0.41 mmol) in trifluoroacetic acid (6 mL) and methylene chloride (6 mL) was stirred at 25° C. for 30 min. At this time, the reaction was concentrated in vacuo to give red oil. The oil was triturated with ether to afford the trifluoroacetic acid salt of 3-Amino-pyrrolidine-1-carboxylic acid (7-methoxy-thiazolo[5,4-b]pyridine-2-yl)-amide (160 mg, 99%) as a light brown solid.

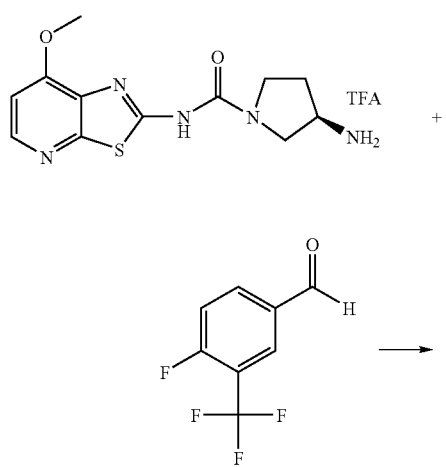

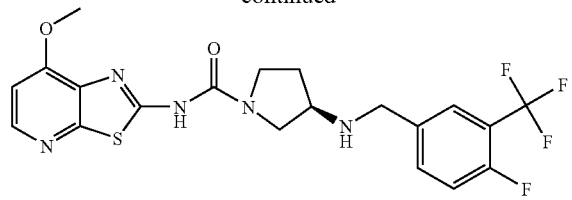

Step 3: A suspension of the trifluoroacetic acid salt of 3-Amino-pyrrolidine-1-carboxylic acid (7-methoxy-thiazolo[5,4-b]pyridine-2-yl)-amide (160 mg, 0.39 mmol) in methanol was treated with N,N-diisopropylethylamine (0.28 mL, 1.57 mmol). Stir the reaction at 25° C. for 30 min. The methanol is then removed in vacuo. 4-fluoro-3-(trifluoromethyl)benzaldehyde (0.08 mL, 0.59 mmol) and toluene are then added to the flask and the resulting mixture was stirred at 60° C. for 1 h and was then concentrated in vacuo. This procedure was repeated until the reaction mixture became homogenous when dissolved in toluene. After the final concentration to remove toluene, the reaction mixture was diluted with dichloroethane (15 mL) and then was treated with acetic acid (94 mg) and sodium triacetoxyborohydride (250 mg, 1.18 mmol). The resulting reaction mixture was allowed to stir at 25° C. overnight. At this time, the reaction mixture was poured into 1N NaOH and extracted into methylene chloride. The organics were washed with a saturated aqueous sodium bicarbonate solution, dried over sodium sulfate, filtered and concentrated in vacuo. Flash chromatography (Merck Silica gel 60, 230-400 mesh, 98:2 methylene chloride/methanol) afforded a colorless oil. The oil was dissolved in diethyl ether and then was concentrated in vacuo to afford 3-(4-Fluoro-3-trifluoromethyl-benzylamino)-pyrrolidine-1-carboxylic acid (7-methoxy-thiazolo[5,4-b]pyridin-2-yl)-amide (19 mg, 25%) as a white solid. LRMS for $C_{20}H_{19}F_4N_5O_2S$ $(M+H)^{30}$ at m/z=469. The NMR spectrum obtained on the sample is compatible with its structure.

EXAMPLE 102

4-(3-Trifluoromethyl-benzyl)-piperazine-1-carboxylic acid (7-methoxy-thiazolo[5,4-b]pyridin-2-yl)-amide

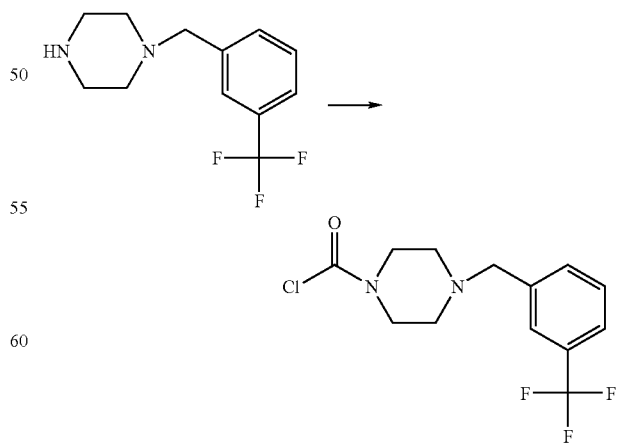

Step 1: A magnetically stirred mixture of triphosgene (365 mg, 1.23 mmol) in tetrahydrofuran (20 mL) under a nitrogen atmosphere was treated slowly with pyridine (485 mg, 6.15 mmol) via syringe. The resulting white suspension was then treated with a solution of 1-(3-Trifluoromethyl-benzyl) piperazine (1.0 g, 4.10 mmol) in tetrahydrofuran (10 mL) via addition funnel over 10 min. The reaction mixture was stirred at 25° C. overnight. At this time, the reaction was filtered to remove solids. The filtrate was then concentrated in vacuo. Flash chromatography (Merck Silica gel 60, 230-400 mesh, 60:40 hexanes/ethyl acetate afforded 4-(3-Trifluoromethyl-benzyl)-piperazine-1-carbonyl chloride (350 mg, 28%) as a clear oil. The NMR spectrum obtained on the sample is compatible with its structure.

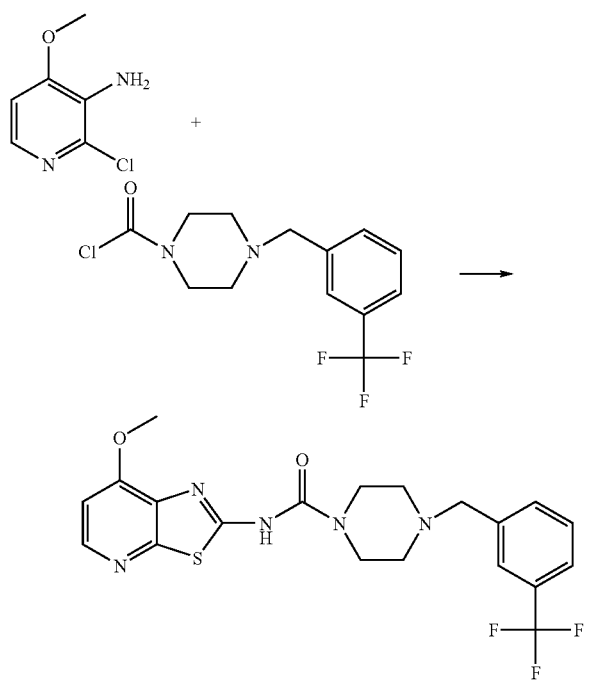

Step 2: A magnetically stirred mixture of 4-(3-Trifluoromethyl-benzyl)-piperazine-1-carbonyl chloride (500 mg, 1.630 mmol) in acetone (20 mL) under a nitrogen atmosphere at 25° C. was treated with ammonium thiocyanate (115 mg, 1.49 mmol). The reaction mixture was stirred at reflux for 30 min. At this time, the reaction was treated with 3-amino-2-chloro-4 methoxypyridine (215 mg, 1.34 mmol). The reaction mixture was refluxed overnight. At this time, the reaction was concentrated in vacuo, poured into water and extracted with ethyl acetate. The organics were washed with a saturated aqueous sodium chloride solution, dried over magnesium sulfate, filtered and concentrated in vacuo. Flash chromatography (Merck Silica gel 60, 230-400 mesh, 75:25 hexanes/ethyl acetate) afforded 4-(3-Trifluoromethyl-benzyl)-piperazine-1-carboxylic acid (7-methoxy-thiazolo[5,4-b]pyridin-2-yl)-amide (35 mg, 15%) as white solid. LRMS for $C_{20}H_{20}F_3N_5O_2S$ $(M+H)^+$ at m/z=451. The NMR spectrum obtained on the sample is compatible with its structure.

EXAMPLE 103

Inhibitory Activity on NECA-Induced Cyclic AMP Production in CHO.K1 Cells Expressing Human Adenosine A2B Receptor.

A Chinese hamster ovary (CHO.K1) cell stably transfected with human adenosine A2B receptor cDNA 4b was used in this assay. Cells were cultured under 5%CO2/95% O2 atmosphere at 37° C. in DMEM and D-MEM/F-12 (1:1 mixture) medium (Invitrogen, Grand Island, N.Y.) with 10% fetal calf serum (Invitrogen, Grand Island, N.Y.), 100 U/mL penicillin (Invitrogen, Grand Island, N.Y.), 100 U/mL streptomycin (Invitrogen, Grand Island, N.Y.), 1 mg/mL G418 (Invitrogen, Grand Island N.Y.) and 0.2 mg/mL Hygromycin B (Invitrogen, Carlsbad, Calif.). Experimental cultures were grown overnight as a monolayer in 384-well tissue culture plates (0.06 ml/well-7500 cells/well). Each well was washed once with 0.1 mL of Krebs buffer. To each well was added 50 uL of Krebs buffer containing 100 uM of the phosphodiesterase inhibitor 4-(3-butoxy-4-methoxybenzyl)-2-imidazolidinone, 100 nM NECA (Sigma-Aldrich, St. Louis, Mo.), 0.02% BSA Fraction V (Roche Biochemicals), the test compound (appropriate concentration). The final concentration of DMSO was 1.1%. After incubation for 30-45 min, the wells were emptied and blotted on paper towel to remove residual solution. The HitHunter™ cAMP Assay Kit from DiscoverX for adherent cells (Fremont, Calif.) was used for lysing the cells and measuring cAMP concentrations. The compounds of Examples 1-102 exhibit $IC_{50}$ values within the range of approximately 1 nanomolar to 1 micromolar. Specific representative examples are set forth in Table I below.

TABLE I

TABLE I

| Example | IC50 (μM) |
| --- | --- |
| 1 | 0.005 |
| 10 | 0.030 |
| 16 | 0.197 |
| 27 | 1.560 |
| 31 | 0.009 |
| 48 | 0.009 |
| 54 | 1.462 |
| 57 | 0.052 |
| 62 | 0.218 |
| 67 | 0.051 |
| 76 | 0.073 |
| 87 | 0.002 |
| 89 | 0.004 |
| 95 | 0.115 |

The invention claimed is:
1. A compound of the formula

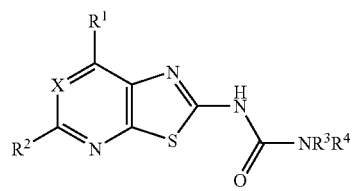

wherein
X is N,
$R^1$ is $C_{1-4}$ alkoxy,
$R^2$ is hydrogen, hydroxy, $C_{1-2}$ alkoxy or $C_{1-2}$ alkylthio,
$R^3$ is hydrogen or $C_{1-3}$ alkyl,
$R^4$ is $C_{1-4}$ alkyl substituted with aryl, aroyl, aryloxy, arylsulfonyl, aralkylamino, or aroylamino, or
R³ and R⁴ together with the urea nitrogen to which they are attached form a 5 to 6 membered heterocyclic ring of the formula

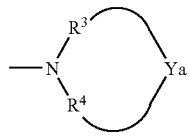

wherein R³ and R⁴ are both CH₂ or one is CH₂ and the other is a methylene mono-substituted with lower alkyl,
Ya is a saturated or partially unsaturated alkyl segment of 2 to 3 ring carbons which is substituted with an aromatic substituent selected from the group consisting of aryl, aralkyl, aralkyloxy, aroyl, aryloxy, arylsulfonyl, aralkylamino, aryloxyalkyl, aryloxyalkylamino and aroylamino, and Ya may additionally have 0, 1 or 2 non-aromatic substituents selected from hydroxy, amino, lower alkylamino, lower alkanoylamino, oxo, cyano, carboxy, hydroxyalkylamino, carbamoyl and lower alkylcarbamoyl,
or
R³ and R⁴ together with the urea nitrogen to which they are attached form a 5 to 6 membered heterocyclic ring of the formula

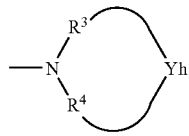

wherein R³ and R⁴ are both CH₂ or one is CH₂ and the other is a methylene mono-substituted with lower alkyl,
Yh is a saturated heteroalkyl segment of 2 to 3 ring atoms one of which is a heteroatom, and Yh is substituted with one aromatic group which in the case of a carbon ring atom is selected from the group consisting of aryl, aralkyl, aroyl, aryloxy, arylsulfonyl, aralkylamino, aryloxyalkyl, aryloxyalkylamino and aroylamino or, in the case of nitrogen, is selected from the group consisting of aryl, aralkyl, aroyl, arylhydroxymethylalkyl, arylcarboxymethylalkyl, arylalkoxymethylalkyl, arylsulfonyl, aryloxyalkyl, arylaminoalkyl and aroylaminoalkyl,
or
R³ and R⁴ together with the urea nitrogen to which they are attached form a piperidinyl or pyrrolidinyl which is benz-fused to unsubstituted or mono- di- or tri-substituted phenyl,
or
R³ and R⁴ together with the urea nitrogen to which they are attached form a piperidinyl which is spiro-fused to a 5 to 6 membered saturated heterocyclic ring containing from 1 or 2 heteroatoms which heterocyclic ring is bound or benz-fused to an unsubstituted or mono- di- or tri-substituted phenyl, and said heterocyclic ring may additionally have 0, 1 or 2 non-aromatic substituents selected from lower alkyl, oxo, acyl and lower alkylsulfonyl,
or
R³ and R⁴ together with the urea nitrogen to which they are attached form a 5-substituted 2,5-diaza-[2.2.1]-bicycloheptane or 5-substituted 2,5-diaza-[3.3.0]-bicyclooctane wherein the 5-substituent is selected from the group consisting of aryl, aralkyl, aryloxy, aralkylamino, aryloxyalkylamino, aroylamino, aroyl, arylsulfonyl, aryloxyalkyl, and arylhydroxymethylalkyl, arylcarboxymethylalkyl, arylalkoxymethylalkyl,
or the pharmaceutically acceptable salts or esters thereof.

2. The compound of claim 1 wherein
R² is hydrogen or hydroxy,
R³ is hydrogen or C₁₋₃ alkyl, and
R⁴ is C₁₋₄ alkyl substituted with aryl, aralkyl, aroyl, aryloxy, arylsulfonyl, aralkylamino or aroylamino.

3. The compound of claim 1 wherein
R³ and R⁴ together with the urea nitrogen to which they are attached form a 5 to 6 membered heterocyclic ring of the formula

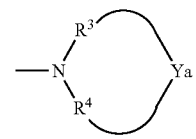

wherein R³ and R⁴ are both CH₂ or one is CH₂ and the other is a methylene mono-substituted with lower alkyl,
Ya is a saturated or partially unsaturated alkyl segment of 2 to 3 ring carbons which is substituted with an aromatic substituent selected from the group consisting of aryl, aralkyl, aralkyloxy, aroyl, aryloxy, arylsulfonyl, aralkylamino, aryloxyalkyl, aryloxyalkylamino and aroylamino, and Ya may additionally have 0, 1 or 2 non-aromatic substituents selected from hydroxy, amino, lower alkylamino, lower alkanoylamino, oxo, cyano, carboxy, hydroxyalkylamino, carbamoyl and lower alkylcarbamoyl,
or
R³ and R⁴ together with the urea nitrogen to which they are attached form a 5 to 6 membered heterocyclic ring of the formula

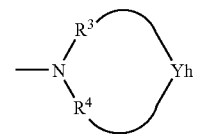

wherein R³ and R⁴ are both CH₂ or one is CH₂ and the other is a methylene mono-substituted with lower alkyl,
Yh is a saturated heteroalkyl segment of 2 to 3 ring atoms one of which is a heteroatom, and Yh is substituted with one aromatic group which in the case of a carbon ring atom is selected from the group consisting of aryl, aralkyl, aroyl, aryloxy, arylsulfonyl, aralkylamino, aryloxyalkyl, aryloxyalkylamino and aroylamino or, in the case of nitrogen, is selected from the group consisting of aryl, aralkyl, aroyl, arylhydroxymethylalkyl, arylcarboxymethylalkyl, arylalkoxymethylalkyl, arylsulfonyl, aryloxyalkyl, arylaminoalkyl and aroylaminoalkyl.

4. The compound of claim 3 wherein R¹ is methoxy and R² is hydrogen or hydroxy.

5. The compound of claim 1 wherein R³ and R⁴ together with the urea nitrogen to which they are attached form a piperidinyl or pyrrolidinyl ring which is benz-fused to unsubstituted or mono-, di- or tri-substituted phenyl.

6. The compound of claim 5 wherein $R^1$ is methoxy and $R^2$ is hydrogen or hydroxy.

7. The compound of claim 1 wherein $R^3$ and $R^4$ together with the urea nitrogen to which they are attached form a piperidinyl or pyrrolidinyl which is spiro-fused to a 5 to 6 membered saturated heterocyclic ring containing from 1 or 2 heteroatoms which heterocyclic ring is bound or benz-fused to an unsubstituted or mono- di- or tri-substituted phenyl, and said heterocyclic ring may additionally have 0, 1 or 2 non-aromatic ring substituents selected from lower alkyl, acyl and lower alkylsulfonyl.

8. The compound of claim 7 wherein $R^1$ is methoxy and $R^2$ is hydrogen or hydroxy.

9. The compound of claim 3 wherein the heterocyclic ring formed with $R^3$ and $R^4$ is pyrrolidinyl, piperidinyl or piperazinyl.

10. The compounds of claim 9 having the formula:

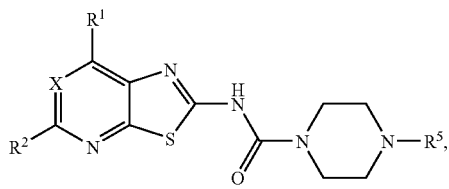

wherein
$R^5$ is aryl, aralkyl, aroyl, aryloxyalkyl, arylsulfonyl, arylaminoalkyl, arylhydroxymethylalkyl, arylalkoxymethylalkyl, arylcarboxymethylalkyl or aroylaminoalkyl.

11. The compound of claim 10 wherein $R^1$ is methoxy and $R^2$ is hydrogen or hydroxy.

12. The compound of claim 1 having the formula

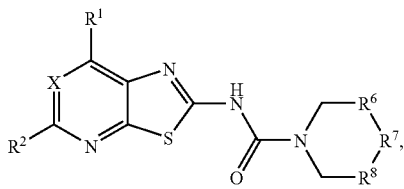

wherein one of $R^6$, $R^7$ and $R^8$ is $CH_2$, one of $R^6$, $R^7$ and $R^8$ is $CH_2$ or CH(OH) and one of $R^6$, $R^7$ and $R^8$ is methylene mono-substituted with an aromatic substituent selected from aryl, aralkyl, aralkyloxy, aroyl, aryloxy, arylsulfonyl, aralkylamino, aryloxyalkyl, aryloxyalkylamino and aroylamino, or is di-substituted methylene wherein one subsituent is an aromatic substituent selected from aryl, aralkyl, aralkyloxy, aroyl, aryloxy, arylsulfonyl, aralkylamino, aryloxyalkyl, aryloxyalkylamino and aroylamino, and the other substituent is non-aromatic substituent selected from hydroxy, cyano, amino, lower alkylamino, lower alkanoylamino, carboxy, hydroxyalkylamino, carbamoyl and lower alkylcarbamoyl.

13. The compound of claim 12 wherein $R^1$ is methoxy and $R^2$ is hydrogen or hydroxy.

14. The compound of claim 12 wherein the aryl ring of the aromatic substituent is substituted with one or two substituents independently selected from the group consisting of halo, hydroxy, lower alkoxy, haloalkyl and haloalkoxy.

15. The compound of claim 14 wherein the one or two substituents are independently selected from the group consisting of chloro, fluoro, methoxy, perfluoroalkyl and perfluoromethoxy.

16. The compound of claim 9 having the formula

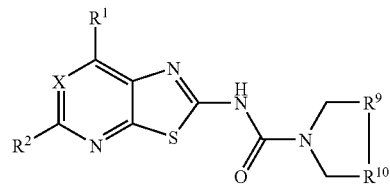

wherein one of $R^9$ and $R^{10}$ is $CH_2$ and the other is a methylene substituted with one aromatic substituent or disubstituted with one aromatic substituent and one non-aromatic substituent, wherein said aromatic substituent is selected from aryl, aralkyl, aralkyloxy, aroyl, aryloxy, arylsulfonyl, aralkylamino, aryloxyalkyl, aryloxyalkylamino and aroylamino, and said non-aromatic substituent is selected from hydroxy, cyano, amino, alkylamino, carboxy, hydroxyalkylamino, carbamoyl and lower alkylcarbamoyl.

17. The compound of claim 16 wherein $R^1$ is methoxy and $R^2$ is hydrogen or hydroxy.

18. The compound of claim 16 wherein the aryl ring of the aromatic substituent is substituted with one or two substituents selected from the group consisting of halo, hydroxy, lower alkoxy, haloalkyl and haloalkoxy.

19. The compound of claim 18 wherein the one or two substituents are independently selected from the group consisting of chloro, fluoro, methoxy, perfluoroalkyl and perfluoromethoxy.

20. A compound having the formula

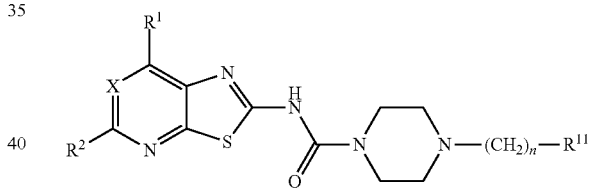

wherein
$R^1$ is $C_{1-4}$ alkoxy,
$R^2$ is hydrogen, hydroxy, $C_{1-2}$ alkoxy or $C_{1-2}$ alkylthio, and
$R^{11}$ is aryl, aroyl, aryloxy or arylsulfonyl and n is 1-4.

21. The compound of claim 7 of the formula

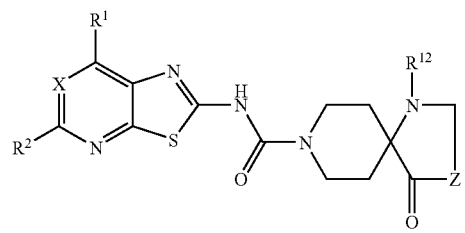

wherein
Z is carbon or nitrogen, and
$R^{12}$ is unsubstituted or mono-, di- or tri-substituted phenyl.

22. The compound of claim 21 wherein $R^1$ is methoxy and $R^2$ is hydrogen or hydroxy.

23. The compound according to claim 7 having the formula

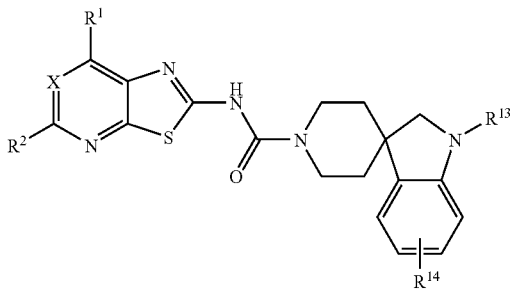

wherein $R^{13}$ is hydrogen, lower alkyl or lower alkylsulfonyl, and $R^{14}$ is hydrogen, halo, lower alkyl or lower alkylsulfonyl.

24. The compound of claim 23 wherein $R^1$ is methoxy and $R^2$ is hydrogen or hydroxy.

25. The compound of claim 1 having the formula

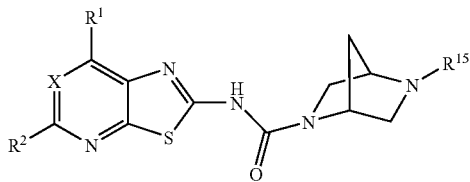

wherein $R^{15}$ is selected from the group consisting of aryl, aralkyl, aroyl, aryloxy, arylsulfonyl, aralkylamino, aryloxyalkyl, aryloxyalkylamino, aroylamino, arylhydroxymethylalkyl, arylcarboxymethylalkyl, and arylalkoxymethylalkyl.

26. The compound of claim 25 wherein $R^1$ is methoxy and $R^2$ is hydrogen or hydroxy.

27. The compound according to claim 1 of the formula

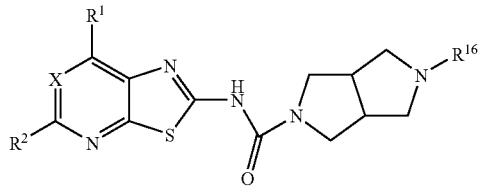

wherein $R^{16}$ is selected from the group consisting of aryl, aralkyl, aroyl, aryloxy, arylsulfonyl, aralkylamino, aryloxyalkyl, aryloxyalkylamino, aroylamino, arylhydroxymethylalkyl, arylcarboxymethylalkyl, and arylalkoxymethylalkyl.

28. The compound of claim 27 wherein $R^1$ is methoxy and $R^2$ is hydrogen or hydroxy.

29. The compound according to claim 1 selected from the group consisting of:
- 4-(3-trifluoromethyl-benzyl)-piperazine-1-carboxylic acid (7-methoxy-thiazolo[5,4-d]pyrimidin-2-yl)-amide,
- 4-(3-Chloro-benzyl)-piperazine-1-carboxylic acid (7-methoxy-thiazolo[5,4-d]pyrimidin-2-yl)-amide,
- 4-(4-Chloro-benzyl)-piperazine-1-carboxylic acid (7-methoxy-thiazolo[5,4-d]pyrimidin-2-yl)-amide,
- 4-(3-Cyano-benzyl)-piperazine-1-carboxylic acid (7-methoxy-thiazolo[5,4-d]pyrimidin-2-yl)-amide,
- 4-(2-Chloro-benzyl)-piperazine-1-carboxylic acid (7-methoxy-thiazolo[5,4-d]pyrimidin-2-yl)-amide,
- 4-(3-Methoxy-benzyl)-piperazine-1-carboxylic acid (7-methoxy-thiazolo[5,4-d]pyrimidin-2-yl)-amide,
- 4-(3,4-Difluoro-benzyl)-piperazine-1-carboxylic acid (7-methoxy-thiazolo[5,4-d]pyrimidin-2-yl)-amide,
- 4-(3-Chloro-4-methoxy-benzyl)-piperazine-1-carboxylic acid (7-methoxy-thiazolo[5,4-d]pyrimidin-2-yl)-amide,
- 4-(3-Nitro-benzyl)-piperazine-1-carboxylic acid (7-methoxy-thiazolo[5,4-d]pyrimidin-2-yl)-amide, and
- 3-[4-(7-Methoxy-thiazolo[5,4-d]pyrimidin-2-ylcarbamoyl)-piperazin-1-ylmethyl]-benzoic acid methyl ester.

30. The compound selected from the group consisting of:
- 4-(3,5-Dimethoxy-benzyl)piperazine-1-carboxylic acid (7-methoxy-thiazolo[5,4-d]pyrimidin-2-yl)-amide,
- 4-(3-Trifluoromethoxy-benzyl)-piperazine-1-carboxylic acid (7-methoxy-thiazolo[5,4-d]pyrimidin-2-yl)-amide,
- 4-(3-Difluoromethoxy-benzyl)-piperazine-1-carboxylic acid (7-methoxy-thiazolo[5,4-d]pyrimidin-2-yl)-amide,
- 4-(3,5-Dichloro-benzyl)-piperazine-1-carboxylic acid (7-methoxy-thiazolo[5,4-d]pyrimidin-2-yl)-amide,
- 4-(3-Hydroxy-benzyl)-piperazine-1-carboxylic acid (7-methoxy-thiazolo[5,4-d]pyrimidin-2-yl)-amide,
- 4-[3-(2-Hydroxy-ethoxy)-benzyl]-piperazine-1-carboxylic acid (7-methoxy-thiazolo[5,4-d]pyrimidin-2-yl)-amide,
- 4-[1-(3-Chloro-phenyl)-ethyl]-piperazine-1-carboxylic acid (7-methoxy-thiazolo[5,4-d]pyrimidin-2-yl)-amide,
- 4-Phenethyl-piperazine-1-carboxylic acid (7-methoxy-thiazolo[5,4-d]pyrimidin-2-yl)-amide,
- 4-(4-Fluoro-3-trifluoromethyl-benzyl)-piperazine-1-carboxylic acid (7-methoxy-thiazolo[5,4-d]pyrimidin-2-yl)-amide, and
- 4-(6-Trifluoromethyl-pyridin-3-ylmethyl)-piperazine-1-carboxylic acid (7-methoxy-thiazolo[5,4-d]pyrimidin-2-yl)-amide.

31. The compound selected from the group consisting of:
- 4-(5-Chloro-2-hydroxy-benzyl)-piperazine-1-carboxylic acid (7-methoxy-thiazolo[5,4-d]pyrimidin-2-yl)-amide,
- {3-[4-(7-Methoxy-thiazolo[5,4-d]pyrimidin-2-ylcarbamoyl)-piperazin-1-ylmethyl]-phenoxy}-acetic acid,
- 4-(3,5-Dichloro-2-hydroxy-benzyl)-piperazine-1-carboxylic acid (7-methoxythiazolo[5,4-d]pyrimidin-2-yl)-amide,
- 4-(3-Fluoro-2-hydroxy-benzyl)-piperazine-1-carboxylic acid (7-methoxy-thiazolo[5,4-d]pyrimidin-2-yl)-amide,
- 4-(5-Fluoro-2-hydroxy-benzyl)-piperazine-1-carboxylic acid (7-methoxy-thiazolo[5,4-d]pyrimidin-2-yl)-amide,
- 4-(2-Hydroxy-3-methyl-benzyl)-piperazine-1-carboxylic acid (7-methoxy-thiazolo[5,4-d]pyrimidin-2-yl)-amide,
- 2-Hydroxy-3-[4-(7-methoxy-thiazolo[5,4-d]pyrimidin-2-ylcarbamoyl)-piperazin-1-ylmethyl]-benzoic acid,
- 4-(6-Morpholin-4-yl-pyridin-3-yl methyl)-piperazine-1-carboxylic acid (7-methoxy-thiazolo[5,4-d]pyrimidin-2-yl)-amide,
- 4-pyridin-2-ylmethyl-piperazine-1-carboxylic acid (7-methoxy-thiazolo[5,4-d]pyrimidin-2-yl)-amide, and
- 4-Benzyl-piperazine-1-carboxylic acid (7-methoxy-thiazolo[5,4-d]pyrimidin-2-yl)-amide.

32. The compound selected from the group consisting of:
- 4-(4-chloro-2-methanesulfonyl-benzyl)-piperazine-1-carboxylic acid (7-methoxy-thiazolo[5,4-d]pyrimidin-2-yl)-amide,
- 4-(3,4-Dichloro-benzyl)-piperazine-1-carboxylic acid (7-methoxy-thiazolo[5,4-d]pyrimidin-2-yl)-amide,
- 4-(4-Methoxy-3-trifluoromethyl-benzyl)-piperazine-1-carboxylic acid (7-methoxy-thiazolo[5,4-d]pyrimidin-2-yl)-amide,
- 4-(3-Cyano-4-methoxy-benzyl)-piperazine-1-carboxylic acid (7-methoxy-thiazolo[5,4-d]pyrimidin-2-yl)-amide,
- 4-(3,5-Bis-trifluoromethyl-benzyl)-piperazine-1-carboxylic acid (7-methoxy-thiazolo[5,4-d]pyrimidin-2-yl)-amide,
- 4-[2-(3-Trifluoromethyl-phenoxy)-ethyl]-piperazine-1-carboxylic acid (7-methoxy-thiazolo[5,4-d]pyrimidin-2-yl)-amide,
- 4-(4-fluoro-3-trifluoromethyl-benzoyl)-piperazine-1-carboxylic acid (7-methoxy-thiazolo[5,4-d]pyrimidin-2-yl)-amide,
- 4-(6-Trifluoromethyl-pyridine-3-carbonyl)-piperazine-1-carboxylic acid (7-methoxy-thiazolo[5,4-d]pyrimidin-2-yl)-amide,
- 4-(3-Chloro-benzoyl)-piperazine-1-carboxylic acid (7-methoxy-thiazolo[5,4-d]pyrimidin-2-yl)-amide,
- 4-(3-Chloro-benzenesulfonyl)-piperazine-1-carboxylic acid (7-methoxy-thiazolo[5,4-d]pyrimidin-2-yl)-amide, and
- 4-[3-(trifluoromethy)phenyl]piperazine-1-carboxylic acid (7-methoxy-thiazolo[5,4-d]pyrimidin-2-yl)-amide.

33. The compound selected from the group consisting of:
- 2-(4-Trifluoromethyl-phenyl)-morpholine-4-carboxylic acid (7-methoxy-thiazolo[5,4-d]pyrimidin-2-yl)-amide,
- Piperidine-1,3-dicarboxylic acid 1-[(7-methoxy-thiazolo[5,4-d]pyrimidin-2-yl)-amide]3-thiazol-2-ylamide,
- 4-(5-Methyl-2-oxo-2,3-dihydro-benzoimidazol-1-yl)-piperidine-1-carboxylic acid (7-methoxy-thiazolo[5,4-d]pyrimidin-2-yl)-amide,
- 1-(7-Methoxy-thiazolo[5,4-d]pyrimidin-2-ylcarbamoyl)-3-(4-trifluoromethoxy-benzyl)-piperidine-3-carboxylic acid ethyl ester,
- 4'-Hydroxy-3',4',5',6'-tetrahydro-2H-[2,4']bipyridinyl-1'-carboxylic acid (7-methoxy-thiazolo[5,4-d]pyrimidin-2-yl)-amide,
- 3,4-Dihydroxy-4-(3-trifluoromethyl-phenyl)-piperidine-1-carboxylic acid (7-methoxy-thiazolo[5,4-d]pyrimidin-2-yl)-amide,
- 4-(2-Oxo-2,3-dihydro-benzoimidazol-1-yl)-piperidine-1-carboxylic acid (7-methoxy-thiazolo[5,4-d]pyrimidin-2-yl)-amide, and
- 4-(1,3-Dihydro-isoindol-2-yl)-piperidine-1-carboxylic acid (7-methoxy-thiazolo[5,4-d]pyrimidin-2-yl)-amide trifluoroacetate.

34. The compound according to claim 1 selected from the group consisting of:
- 5-Chloro-1,2-dihydro-N-(7-methoxythiazole[5,4-d]pyrimidin-2-yl)-1-(methylsulfonyl)spiro[3H-indole-3,4'-piperidine]-1'-carboxamide,
- 1,2-Dihydro-5-methoxy-N-(7-methoxythiazole[5,4-d]pyrimidin-2-yl)-1-methylspiro[3H-indole-3,4'-piperidine]-1'-carboxamide,
- 1-(Cyclopropylmethyl)-1,2-dihydro-N-(7-methoxythiazole[5,4-d]pyrimidin-2-yl)spiro[3H-indole-3,4'-piperidine]-1'-carboxamide,
- 1-(Cyclopropylmethyl)-1,2-dihydro-5-chloro-N-(7-methoxythiazole[5,4-d]pyrimidin-2-yl)spiro[3H-indole-3,4'-piperidine]-1'-carboxamide,
- 4-(4-Fluoro-phenyl)-1-oxo-2,8-diaza-spiro[4.5]decane-8-carboxylic acid (7-methoxy-thiazolo[5,4-d]pyrimidin-2-yl)-amide, and
- 4-Oxo-1-phenyl-1,3,8-triaza-spiro[4.5]decane-8-carboxylic acid (7-methoxy-thiazolo[5,4-d]pyrimidin-2-yl)-amide.

35. The compound selected from the group consisting of:
- 4-(3-Phenyl-pyrrolidin-1-yl)-piperidine-1-carboxylic acid (7-methoxy-thiazolo[5,4-d]pyrimidin-2-yl)-amide,
- 4-(2-Phenyl-pyrrolidin-1-yl)-piperidine-1-carboxylic acid (7-methoxy-thiazolo[5,4-d]pyrimidin-2-yl)-amide,
- 4-(2,3-Dihydro-indol-1-yl)-piperidine-1-carboxylic acid (7-methoxy-thiazolo[5,4-d]pyrimidin-2-yl)-amide,
- 4-(5-Chloro-2,3-dihydro-indol-1-yl)-piperidine-1-carboxylic acid (7-methoxy-thiazolo[5,4-d]pyrimidin-2-yl)-amide,
- 4-hydroxy-4-(3-trifluoromethyl-phenyl)-piperidine-1-carboxylic acid (7-methoxy-thiazolo[5,4-d]pyrimidin-2-yl)-amide,
- 4-(3-Trifluoromethyl-phenyl)-piperidine-1-carboxylic acid (7-methoxy-thiazolo[5,4-d]pyrimidin-2-yl)-amide,
- 4-(3-Trifluoromethyl-phenyl)-3,6-dihydro-2H-pyridine-1-carboxylic acid (7-methoxy-thiazolo[5,4-d]pyrimidin-2-yl)-amide,
- 3-(3-Trifluoromethyl-benzyl)-piperidine-1-carboxylic acid (7-methoxy-thiazolo[5,4-d]pyrimidin-2-yl)-amide,
- 3-Benzyl-pyrrolidine-1-carboxylic acid (7-methoxy-thiazolo[5,4-d]pyrimidin-2-yl)-amide, and
- 4-(2-Oxo-2,3-dihydro-benzoimidazol-1-yl)-piperidine-1-carboxylic acid (7-methoxy-thiazolo[5,4-d]pyrimidin-2-yl)-amide.

36. The compound according to claim 1 selected from the group consisting of:
- 4-(3-Trifluoromethyl-benzenesulfonyl)-piperidine-1-carboxylic acid (7-methoxy-thiazolo[5,4-d]pyrimidin-2-yl)-amide,
- 4-(4-Chloro-benzenesulfonyl)-piperidine-1-carboxylic acid (7-methoxy-thiazolo[5,4-d]pyrimidin-2-yl)-amide,
- 4-(Toluene-4-sulfonyl)-piperidine-1-carboxylic acid (7-methoxy-thiazolo[5,4-d]pyrimidin-2-yl)-amide,
- 4-(3-Chloro-phenoxy)-piperidine-1-carboxylic acid (7-methoxy-thiazolo[5,4-d]pyrimidin-2-yl)-amide,
- 4-(4-Fluoro-benzyl)-piperidine-1-carboxylic acid (7-methoxy-thiazolo[5,4-d]pyrimidin-2-yl)-amide,
- 2-[1-(7-Methoxy-thiazolo[5,4-d]pyrimidin-2-ylcarbamoyl)-piperidine-4-sulfonyl]-benzoic acid methyl ester, and
- 4-(3-Trifluoromethyl-benzyl)-piperidine-1-carboxylic acid (7-methoxy-thiazolo[5,4-d]pyrimidin-2-yl)-amide.

37. The compound according to claim 1 selected from the group consisting of:
- 4-(3-chloro-phenyl)-4-hydroxy-piperidine-1-carboxylic acid (7-methoxy-thiazolo[5,4-d]pyrimidin-2-yl)-amide,
- 4-Hydroxy-4-(3-methoxy-phenyl)-piperidine-1-carboxylic acid (7-methoxy-thiazolo[5,4-d]pyrimidin-2-yl)-amide,
- 4'-hydroxy-6-trifluoromethyl-3',4',5',6'-tetrahydro-2'H-[2,4']bipyridinyl-1'-carboxylic acid(7-methoxy-thiazolo[5,4-d]pyrimidin-2-yl)-amide, 4-acetylamino-4-(3-trifluoromethyl-phenyl)-piperidine-1-carboxylic acid (7-methoxy-thiazolo[5,4-d]pyrimidin-2-yl)-amide, 4-amino-4-(3-trifluoromethyl-phenyl)-piperidine-1-carboxylic acid (7-methoxy-thiazolo[5,4-d]pyrimidin-2-yl)-amide, 4-(4-fluoro-3-trifluoromethyl-benzylamino)-piperidine-1-carboxylic acid (7-methoxy-thiazolo[5,4-d]pyrimidin-2-yl)-amide, 4-[(6-Trifluoromethyl-pyridin-3-ylmethyl)-amino]-piperidine-1-carboxylic acid (7-methoxy-thiazolo[5,4-d]pyrimidin-2-yl)-amide, and 4-(4-fluoro-3-trifluoromethyl-benzoylamino)-piperidine-1-carboxylic acid (7-methoxy-thiazolo[5,4-d]pyrimidin-2-yl)-amide.

38. The compound according to claim 1 selected from the group consisting of:

3-(4-Chloro-benzyl)-pyrrolidine-1-carboxylic acid (7-methoxy-thiazolo[5,4-d]pyrimidin-2-yl)-amide, 3-(4-Trifluoromethyl-benzyl)-pyrrolidine-1-carboxylic acid (7-methoxy-thiazolo[5,4-d]pyrimidin-2-yl)-amide, 3-(Toluene-4-sulfonyl)-pyrrolidine-1-carboxylic acid (7-methoxy-thiazolo[5,4-d]pyrimidin-2-yl)-amid, 3-[2-(3-trifluoromethyl-phenoxy)-ethylamino]-pyrrolidine-1-carboxylic acid (7-methoxy-thiazolo[5,4-d]pyrimidin-2-yl)-amide, (R)-3-(4-fluoro-3-trifluoromethyl-benzylamino)-pyrrolidine-1-carboxylic acid (7-methoxy-thiazolo[5,4-d]pyrimidin-2-yl)-amide, (R)-3-(4-fluoro-3-trifluoromethyl-benzoylamino)-pyrrolidine-1-carboxylic acid (7-methoxy-thiazolo[5,4-d]pyrimidin-2-yl)-amide, and (S)-3-(4-fluoro-3-trifluoromethyl-benzoylamino)-pyrrolidine-1-carboxylic acid (7-methoxy-thiazolo[5,4-d]pyrimidin-2-yl)-amide.

39. The compound according to claim 1 selected from the group consisting of:

8-Trifluoromethyl-3,4-dihydro-1 H-isoquinoline-2-carboxylic acid (7-methoxy-thiazolo[5,4-d]pyrimidin-2-yl)-amide, and 6-Trifluoromethyl-3,4-dihydro-1 H-isoquinoline-2-carboxylic acid (7-methoxy-thiazolo[5,4-d]pyrimidin-2-yl)-amide.

40. The compound selected from the group consisting of:

4-Fluoro-N-{2-[3-(7-methoxy-thiazolo[5,4-d]pyrimidin-2-yl)-ureido]-ethyl}-3-trifluoromethyl-benzamide, 1-[2-(4-Fluoro-3-trifluoromethyl-benzylamino)-ethyl]-3-(7-methoxy-thiazolo[5,4-d]pyrimidin-2-yl)-urea, 3-(7-Methoxy-thiazolo[5,4-d]pyrimidin-2-yl)-1-methyl-1-[2-(3-trifluoromethyl-phenoxy)-ethyl]urea 4-[1-(3-Chloro-phenyl)-2-hydroxy-ethyl]-piperazine-1-carboxylic acid (7-methoxy-thiazolo[5,4-d]pyrimidin-2-yl)-amide, (3-Chloro-phenyl)-[4-(7-methoxy-thiazolo[5,4-d]pyrimidin-2-ylcarbamoyl)-piperazin-1-yl]-acetic acid methyl ester, 4-[2-Methoxy-1-(3-trifluoromethyl-phenyl)-ethyl]-piperazine-1-carboxylic acid (7-methoxy-thiazolo[5,4-d]pyrimidin-2-yl)-amide, 4-hydroxy-4-[3-(trifluoromethy)phenyl]piperidine-1-carboxylic acid (5-methanesulfonyl-7-methoxy-thiazolo[5,4-d]pyrimidin-2-yl)-amide, and 4-hydroxy-4-[3-(trifluoromethy)phenyl]piperidine-1-carboxylic acid (5-hydroxy-7-methoxy-thiazolo[5,4-d]pyrimidin-2-yl)-amide.

41. A pharmaceutical composition comprising a pharmacologically effective amount of a compound according to claim 1 and a pharmaceutically acceptable carrier material and/or adjuvant.

* * * * *